US008900807B2

(12) United States Patent
Owen et al.

(10) Patent No.: US 8,900,807 B2
(45) Date of Patent: Dec. 2, 2014

(54) COMPOSITION AND METHODS FOR RAPID DETECTION OF HIV BY LOOP-MEDIATED ISOTHERMAL AMPLIFICATION (LAMP)

(75) Inventors: S. Michele Owen, Douglasville, GA (US); Kelly Curtis, Atlanta, GA (US); Donna Rudolph, Lilburn, GA (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 923 days.

(21) Appl. No.: 12/918,536

(22) PCT Filed: Feb. 25, 2009

(86) PCT No.: PCT/US2009/035130
§ 371 (c)(1),
(2), (4) Date: Aug. 20, 2010

(87) PCT Pub. No.: WO2009/108693
PCT Pub. Date: Sep. 3, 2009

(65) Prior Publication Data
US 2012/0088244 A1    Apr. 12, 2012

Related U.S. Application Data

(60) Provisional application No. 61/031,128, filed on Feb. 25, 2008.

(51) Int. Cl.
*C12Q 1/70* (2006.01)
*C12P 19/34* (2006.01)

(52) U.S. Cl.
CPC .......... *C12Q 1/703* (2013.01); *C12Q 2531/119* (2013.01)
USPC .............................. 435/5; 435/6.12; 435/91.2

(58) Field of Classification Search
USPC ............... 435/6.12, 91.2, 5; 536/24.32, 24.33
See application file for complete search history.

(56) References Cited

U.S. PATENT DOCUMENTS

| | | | |
|---|---|---|---|
| 6,951,722 | B2 | 10/2005 | Mukai et al. |
| 7,056,671 | B2 | 6/2006 | Enoki et al. |
| 2003/0073081 | A1 | 4/2003 | Mukai et al. |
| 2004/0115643 | A1 | 6/2004 | Lizardi et al. |
| 2004/0185455 | A1 | 9/2004 | Shimada et al. |
| 2005/0059000 | A1 | 3/2005 | Sagawa et al. |
| 2005/0059003 | A1 | 3/2005 | Enoki et al. |
| 2005/0123950 | A1 | 6/2005 | Mukai et al. |
| 2005/0239100 | A1 | 10/2005 | Mukai et al. |
| 2006/0204997 | A1 | 9/2006 | Macioszek et al. |
| 2006/0210433 | A1 | 9/2006 | Lair et al. |
| 2006/0211130 | A1 | 9/2006 | Macioszek et al. |
| 2006/0234263 | A1 | 10/2006 | Light |
| 2006/0240462 | A1 | 10/2006 | Todd et al. |
| 2006/0276972 | A1 | 12/2006 | Light et al. |
| 2007/0004028 | A1 | 1/2007 | Lair et al. |
| 2007/0196902 | A1 | 8/2007 | Mellors et al. |
| 2007/0243600 | A1 | 10/2007 | Lair et al. |
| 2007/0281317 | A1 | 12/2007 | Becker et al. |
| 2012/0202190 | A1* | 8/2012 | Ching et al. ...................... 435/5 |

FOREIGN PATENT DOCUMENTS

| | | | |
|---|---|---|---|
| CN | 1687454 | * | 10/2005 |
| EP | 1876246 | | 1/2008 |

OTHER PUBLICATIONS

Poon et al., Clinical Chemistry 52(2), 303-306 (2006).*
Thai, H. et al., Development and Evaluation of a Novel Loop-Mediated isothermal Amplification Method for Rapid Detection of Severe Acute Respiratory Syndrome Coronavirus, *Journal of Clinical Microbiology*, 42(5): 1956-61, May 2004.
Lee, S. et al., Efficient, specific, compact hepatitis B diagnostic device: Optical detection of the hepatitis B virus by isothermal amplification, *Sensors and Actuators B: Chemical*, 127(2): 598-605, Nov. 15, 2007; May 2004.
Curtis, K. et al., Rapid detection of HIV-1 by reverse-transcription, loop-mediated isothermal amplification (RT-LAMP), *Journal of Virological Methods*, 151(2): 264-70, Aug. 2008.
Hosaka, K. et al., Rapid detection of human immunodeficiency virus type 1 group M by a reverse transcription-loop-mediated isothermal amplification assay, *Journal of Virological Methods*, 157(2): 195-99, May 2009.
Tomita, N, et al., Loop-mediated isothermal amplification (LAMP) of gene sequences and simple visual detection of products, *Nature Protocols*, 3(5): 877-882, 2008.
Notomi, T. et al., Loop-mediated isothermal amplification of DNA, *Nucleic Acids Research*, 28(12): e-63 i-vii, 2000.
Nagamine, K. et al., Accelerated reaction by loop-mediated isothermal amplification using loop primers, Molecular and Cellular Probes, 16: 223-229, 2002.
Mori, Y. et al. Sequence specific visual detection of Lamp reactions by addition of cationic polymers, *BMC Biotechnology*, 6(3): 1-10, 2006.
Kurosaki, Y. et al., Rapid and simple detection of Ebola virus by reverse transcription-loop-mediated isothermal amplification, *Journal of Virological Methods*, 141: 78-83, 2007.
Tani, H. et al., Technique for Quantitative Detection of Specific DNA Sequences Using Alternately Binding Quenching Probe Competitive Assay Combined with Loop-Mediated Isothermal Amplification, *Anal Chem*, 79: 5608-13, 2007.

(Continued)

*Primary Examiner* — Kenneth Horlick
(74) *Attorney, Agent, or Firm* — Gifford, Krass, Sprinkle, Anderson & Citkowski, P.C.

(57) ABSTRACT

Methods and compositions for detection of HIV nucleic acids in a sample, such as a biological sample obtained from a human subject, are provided according to embodiments of the present invention which include providing a reaction mixture including at least one LAMP, accelerated LAMP, RT-LAMP or RT-accelerated LAMP assay primer set specific for HIV-I or HIV-2 nucleic acids and the biological sample to be tested for presence of HIV-I and/or HIV-2 nucleic acids; incubating the reaction mixture under conditions suitable to produce a LAMP assay reaction product; and detecting the reaction product. Primers and primer sets for use in LAMP assays of HIV-I or HIV-2 nucleic acids are provided.

20 Claims, 5 Drawing Sheets

(56) References Cited

OTHER PUBLICATIONS

Fiscus, S. et al., Rapid, Real-Time Detection of Acute HIV Infection in Patients in Africa, *Journal of Infectious Diseases*, 195: 416-24, 2007.

Boehme, C. et al., Operational Feasibility of Using Loop-Mediated Isothermal Amplification for Diagnosis of Pulmonary Tuberculosis in Microscopy Centers of Developing Countries, *Journal of Clinical Microbiology*, 45(6): 1936-40, Jun. 2007.

Hecht, F. et al., Use of laboratory tests and clinical symptoms for identification of primary HIV infection, *AIDS*, 16(8): 1119-1129, 2002.

Translation of CN 1687454, published Oct. 26, 2005, Shanghai City Blood CT.

* cited by examiner

Figure 4C
BBI HIV-1 RNA Linearity Panel
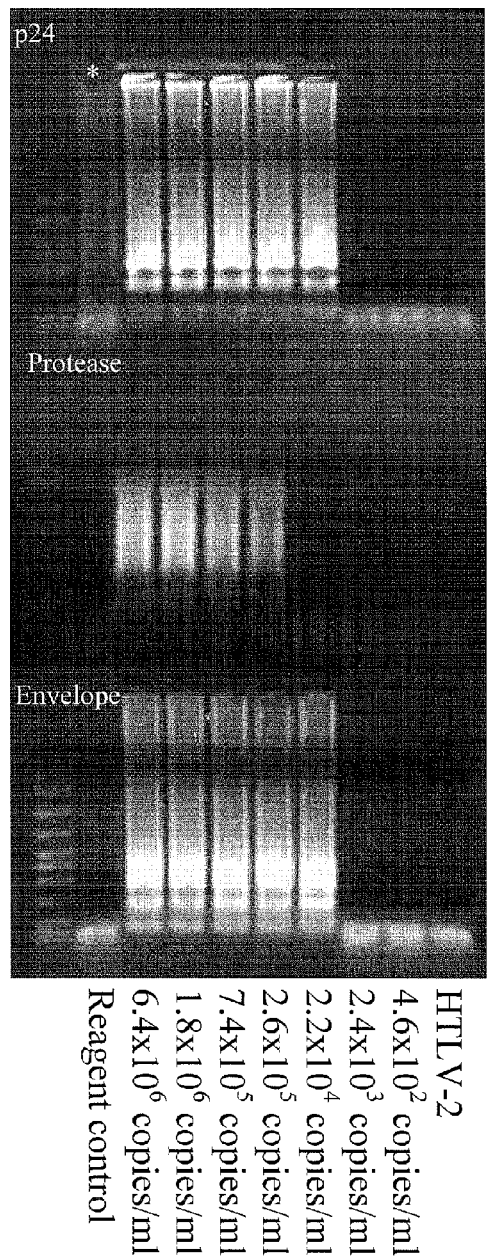
Note: Non-specific amplification (indicated by *) was visible by agarose gel electrophoresis, but did not incorporate the fluorescent probe
Figure 4A
Reaction tubes under UV light
p24 probe (top row)
Protease probe (bottom row)
Figure 4B
Envelope probe

SEQUENCE LISTING

<160> NUMBER OF SEQ ID NOS: 414

<210> SEQ ID NO 1
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 1
attatcagaa ggagccacc                                                         19

<210> SEQ ID NO 2
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 2
catcctattt gttcctgaag g                                                      21

<210> SEQ ID NO 3
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 3
cagcttcctc attgatggtt tctaacacca tgctaaacac agt                              43

<210> SEQ ID NO 4
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 4
tgttgcacca ggccagataa gtactggtag ttcctgctat g                                41

<210> SEQ ID NO 5
<211> LENGTH: 25
<212> TYPE: DNA
<213> ORGANISM: Artificial Sequence
<220> FEATURE:
<223> OTHER INFORMATION: Human immunodeficiency virus P24 loop F primer

<400> SEQUENCE: 5
tttaacattt gcatggctgc ttgat                                                  25

<210> SEQ ID NO 6
<211> LENGTH: 19
<212> TYPE: DNA
<213> ORGANISM: Artificial Sequence
<220> FEATURE:
<223> OTHER INFORMATION: Human immunodeficiency virus P24 loop B primer

<400> SEQUENCE: 6
gagatccaag gggaagtga                                                         19

<210> SEQ ID NO 7
<211> LENGTH: 18
<212> TYPE: DNA

```
<213> ORGANISM: Artificial Sequence
<220> FEATURE:
<223> OTHER INFORMATION: Human immunodeficiency virus protease F3 primer

<400> SEQUENCE: 7
aaagataggg gggcaact                                                    18

<210> SEQ ID NO 8
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 8
gttgacaggt gtaggtccta                                                  20

<210> SEQ ID NO 9
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 9
ggtttccatc ttcctggcaa attctctatt agatacagga gcaga                      45

<210> SEQ ID NO 10
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 23 and
      24.

<400> SEQUENCE: 10
tgataggggg aattggaggt ttcctatagc tttatgtcca caga                       44

<210> SEQ ID NO 11
<211> LENGTH: 22
<212> TYPE: DNA
<213> ORGANISM: Artificial Sequence
<220> FEATURE:
<223> OTHER INFORMATION: Human immunodeficiency virus protease loop F
      primer

<400> SEQUENCE: 11
tatttcttct aatactgtat ca                                               22

<210> SEQ ID NO 12
<211> LENGTH: 18
<212> TYPE: DNA
<213> ORGANISM: Artificial Sequence
<220> FEATURE:
<223> OTHER INFORMATION: Human immunodeficiency virus protease loop B
      primer

<400> SEQUENCE: 12
```
tatcaaagta agacagta                                                    18

<210> SEQ ID NO 13
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 13
aaattgtggg tcacagtct                                                   19

<210> SEQ ID NO 14
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 14
ccacatgtta aattttctg tcac                                              24

<210> SEQ ID NO 15
<211> LENGTH: 42
<212> TYPE: DNA
<213> ORGANISM: Artificial Sequence
<220> FEATURE:
<223> OTHER INFORMATION: Human immunodeficiency virus envelope FIP
      primer
<220> FEATURE:
<221> NAME/KEY: misc_feature
<222> LOCATION: (25)..(25)
<223> OTHER INFORMATION: A linker is present between nucleotides 24 and
      25.

<400> SEQUENCE: 15
tcatatgctt tagcatctga tgcagggtac ctgtgtggaa ag                          42

<210> SEQ ID NO 16
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 16
cagaggtaca taatgtttgg gccactactt cttgtgggtt gg                          42

<210> SEQ ID NO 17
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 17
caaaatagag tggtggttgc t                                                21

<210> SEQ ID NO 18
<211> LENGTH: 18

```
<212> TYPE: DNA
<213> ORGANISM: Artificial Sequence
<220> FEATURE:
<223> OTHER INFORMATION: Human immunodeficiency virus envelope loop B
      primer

<400> SEQUENCE: 18
acacatgcct gtgtaccc                                                    18

<210> SEQ ID NO 19
<211> LENGTH: 19
<212> TYPE: DNA
<213> ORGANISM: Artificial Sequence
<220> FEATURE:
<223> OTHER INFORMATION: Human immunodeficiency virus P24 degenerate F3
      primer

<400> SEQUENCE: 19
attakcagar ggagccayy                                                   19

<210> SEQ ID NO 20
<211> LENGTH: 21
<212> TYPE: DNA
<213> ORGANISM: Artificial Sequence
<220> FEATURE:
<223> OTHER INFORMATION: Human immunodeficiency virus P24 degenerate B3
      primer

<400> SEQUENCE: 20
catsctattt gytcctgarg r                                                21

<210> SEQ ID NO 21
<211> LENGTH: 43
<212> TYPE: DNA
<213> ORGANISM: Artificial Sequence
<220> FEATURE:
<223> OTHER INFORMATION: Human immunodeficiency virus P24 degenerate FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 21
cagcytcctc attgatggtt tctaacacca tgytaaayay agt                         43

<210> SEQ ID NO 22
<211> LENGTH: 41
<212> TYPE: DNA
<213> ORGANISM: Artificial Sequence
<220> FEATURE:
<223> OTHER INFORMATION: Human immunodeficiency virus P24 degenerate BIP
      primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 22
trttgcacca ggccagatra gtactwgtag ttcctgctat r                           41

<210> SEQ ID NO 23
<211> LENGTH: 24
<212> TYPE: DNA
<213> ORGANISM: Artificial Sequence
<220> FEATURE:
<223> OTHER INFORMATION: Human immunodeficiency virus P24 degenerate
```

-continued loop F primer

<400> SEQUENCE: 23
tttaacatyt gcatrgctgc ytgr                                          24

<210> SEQ ID NO 24
<211> LENGTH: 19
<212> TYPE: DNA
<213> ORGANISM: Artificial Sequence
<220> FEATURE:
<223> OTHER INFORMATION: Human immunodeficiency virus P24 degenerate
      loop B primer

<400> SEQUENCE: 24
grgamccaag gggaagtga                                                19

<210> SEQ ID NO 25
<211> LENGTH: 18
<212> TYPE: DNA
<213> ORGANISM: Artificial Sequence
<220> FEATURE:
<223> OTHER INFORMATION: Human immunodeficiency virus integrase F3
      primer

<400> SEQUENCE: 25
ttggagagca atggctag                                                 18

<210> SEQ ID NO 26
<211> LENGTH: 19
<212> TYPE: DNA
<213> ORGANISM: Artificial Sequence
<220> FEATURE:
<223> OTHER INFORMATION: Human immunodeficiency virus integrase B3
      primer

<400> SEQUENCE: 26
ccactggcta catgaactg                                                19

<210> SEQ ID NO 27
<211> LENGTH: 41
<212> TYPE: DNA
<213> ORGANISM: Artificial Sequence
<220> FEATURE:
<223> OTHER INFORMATION: Human immunodeficiency virus integrase FIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 27
gctgacattt atcacagctg gctgatttta acctgccacc t                       41

<210> SEQ ID NO 28
<211> LENGTH: 45
<212> TYPE: DNA
<213> ORGANISM: Artificial Sequence
<220> FEATURE:
<223> OTHER INFORMATION: Human immunodeficiency virus integrase BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 28

```
gccatgcatg gacaagtaga ctctaccagg ataattttc cttct                45
```

<210> SEQ ID NO 29
<211> LENGTH: 20
<212> TYPE: DNA
<213> ORGANISM: Artificial Sequence
<220> FEATURE:
<223> OTHER INFORMATION: Human immunodeficiency virus integrase loop F
      primer

<400> SEQUENCE: 29

```
actatttctt ttgctaccac                                            20
```

<210> SEQ ID NO 30
<211> LENGTH: 18
<212> TYPE: DNA
<213> ORGANISM: Artificial Sequence
<220> FEATURE:
<223> OTHER INFORMATION: Human immunodeficiency virus integrase loop B
      primer

<400> SEQUENCE: 30

```
ccaggaatat ggcaacta                                              18
```

<210> SEQ ID NO 31
<211> LENGTH: 23
<212> TYPE: DNA
<213> ORGANISM: Artificial Sequence
<220> FEATURE:
<223> OTHER INFORMATION: Human immunodeficiency virus P24 FIP primer
      portion

<400> SEQUENCE: 31

```
cagcttcctc attgatggtt tct                                        23
```

<210> SEQ ID NO 32
<211> LENGTH: 20
<212> TYPE: DNA
<213> ORGANISM: Artificial Sequence
<220> FEATURE:
<223> OTHER INFORMATION: Human immunodeficiency virus P24 FIP primer
      portion

<400> SEQUENCE: 32

```
aacaccatgc taaacacagt                                            20
```

<210> SEQ ID NO 33
<211> LENGTH: 20
<212> TYPE: DNA
<213> ORGANISM: Artificial Sequence
<220> FEATURE:
<223> OTHER INFORMATION: Human immunodeficiency virus P24 BIP primer
      portion

<400> SEQUENCE: 33

```
tgttgcacca ggccagataa                                            20
```

<210> SEQ ID NO 34
<211> LENGTH: 21
<212> TYPE: DNA
<213> ORGANISM: Artificial Sequence
<220> FEATURE:
<223> OTHER INFORMATION: Human immunodeficiency virus P24 BIP primer
      portion

<400> SEQUENCE: 34

```
gtactggtag ttcctgctat g                                          21
```

<210> SEQ ID NO 35
<211> LENGTH: 23
<212> TYPE: DNA
<213> ORGANISM: Artificial Sequence
<220> FEATURE:
<223> OTHER INFORMATION: Human immunodeficiency virus protease FIP
      primer portion

<400> SEQUENCE: 35
ggtttccatc ttcctggcaa att                                           23

<210> SEQ ID NO 36
<211> LENGTH: 22
<212> TYPE: DNA
<213> ORGANISM: Artificial Sequence
<220> FEATURE:
<223> OTHER INFORMATION: Human immunodeficiency virus protease FI
      P primer portion

<400> SEQUENCE: 36
ctctattaga tacaggagca ga                                            22

<210> SEQ ID NO 37
<211> LENGTH: 22
<212> TYPE: DNA
<213> ORGANISM: Artificial Sequence
<220> FEATURE:
<223> OTHER INFORMATION: Human immunodeficiency virus protease BIP
      primer portion

<400> SEQUENCE: 37
tgataggggg aattggaggt tt                                            22

<210> SEQ ID NO 38
<211> LENGTH: 22
<212> TYPE: DNA
<213> ORGANISM: Artificial Sequence
<220> FEATURE:
<223> OTHER INFORMATION: Human immunodeficiency virus protease BIP
      primer portion

<400> SEQUENCE: 38
cctatagctt tatgtccaca ga                                            22

<210> SEQ ID NO 39
<211> LENGTH: 24
<212> TYPE: DNA
<213> ORGANISM: Artificial Sequence
<220> FEATURE:
<223> OTHER INFORMATION: Human immunodeficiency virus envelope FIP
      primer portion

<400> SEQUENCE: 39
tcatatgctt tagcatctga tgca                                          24

<210> SEQ ID NO 40
<211> LENGTH: 18
<212> TYPE: DNA
<213> ORGANISM: Artificial Sequence
<220> FEATURE:
<223> OTHER INFORMATION: Human immunodeficiency virus envelope FIP
      primer portion

<400> SEQUENCE: 40
gggtacctgt gtggaaag                                                 18

```
<210> SEQ ID NO 41
<211> LENGTH: 23
<212> TYPE: DNA
<213> ORGANISM: Artificial Sequence
<220> FEATURE:
<223> OTHER INFORMATION: Human immunodeficiency virus envelope BIP
      primer portion

<400> SEQUENCE: 41
cagaggtaca taatgtttgg gcc                                           23

<210> SEQ ID NO 42
<211> LENGTH: 19
<212> TYPE: DNA
<213> ORGANISM: Artificial Sequence
<220> FEATURE:
<223> OTHER INFORMATION: Human immunodeficiency virus envelope BIP
      primer portion

<400> SEQUENCE: 42
actacttctt gtgggttgg                                                19

<210> SEQ ID NO 43
<211> LENGTH: 22
<212> TYPE: DNA
<213> ORGANISM: Artificial Sequence
<220> FEATURE:
<223> OTHER INFORMATION: Human immunodeficiency virus integrase FIP
      primer portion

<400> SEQUENCE: 43
gctgacattt atcacagctg gc                                            22

<210> SEQ ID NO 44
<211> LENGTH: 19
<212> TYPE: DNA
<213> ORGANISM: Artificial Sequence
<220> FEATURE:
<223> OTHER INFORMATION: Human immunodeficiency virus integrase FIP
      primer portion

<400> SEQUENCE: 44
tgattttaac ctgccacct                                                19

<210> SEQ ID NO 45
<211> LENGTH: 22
<212> TYPE: DNA
<213> ORGANISM: Artificial Sequence
<220> FEATURE:
<223> OTHER INFORMATION: Human immunodeficiency virus integrase BIP
      primer portion

<400> SEQUENCE: 45
gccatgcatg gacaagtaga ct                                            22

<210> SEQ ID NO 46
<211> LENGTH: 23
<212> TYPE: DNA
<213> ORGANISM: Artificial Sequence
<220> FEATURE:
<223> OTHER INFORMATION: Human immunodeficiency virus integrase BIP
      primer portion

<400> SEQUENCE: 46
ctaccaggat aatttttcct tct                                           23
```

```
<210> SEQ ID NO 47
<211> LENGTH: 18
<212> TYPE: DNA
<213> ORGANISM: Artificial Sequence
<220> FEATURE:
<223> OTHER INFORMATION: Human immunodeficiency virus protease
      degenerate F3 primer

<400> SEQUENCE: 47
aarrataggg ggrcarct                                                  18

<210> SEQ ID NO 48
<211> LENGTH: 20
<212> TYPE: DNA
<213> ORGANISM: Artificial Sequence
<220> FEATURE:
<223> OTHER INFORMATION: Human immunodeficiency virus protease
      degenerate B3 primer

<400> SEQUENCE: 48
gttgacrggk gtaggtccda                                                20

<210> SEQ ID NO 49
<211> LENGTH: 45
<212> TYPE: DNA
<213> ORGANISM: Artificial Sequence
<220> FEATURE:
<223> OTHER INFORMATION: Human immunodeficiency virus protease
      degenerate FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 49
ggtttccaty tycctggcaa attckctatt agayacagga gcaga                    45

<210> SEQ ID NO 50
<211> LENGTH: 44
<212> TYPE: DNA
<213> ORGANISM: Artificial Sequence
<220> FEATURE:
<223> OTHER INFORMATION: Human immunodeficiency virus protease
      degenerate BIP primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 50
tgataggrgg aattggaggt ttcctatagc yttwtktcca cara                     44

<210> SEQ ID NO 51
<211> LENGTH: 22
<212> TYPE: DNA
<213> ORGANISM: Artificial Sequence
<220> FEATURE:
<223> OTHER INFORMATION: Human immunodeficiency virus protease
      degenerate loop F primer

<400> SEQUENCE: 51
yatktcttct aatactgtat ca                                             22

<210> SEQ ID NO 52
<211> LENGTH: 18
<212> TYPE: DNA
<213> ORGANISM: Artificial Sequence
```

```
<220> FEATURE:
<223> OTHER INFORMATION: Human immunodeficiency virus protease
      degenerate loop B primer

<400> SEQUENCE: 52 tatca

<221> NAME/KEY: misc_feature
<222> LOCATION: (15)..(15)
<223> OTHER INFORMATION: N is a,g,c or t

<400> SEQUENCE: 57
caaaatagrg tggtnkttgc d                                              21

<210> SEQ ID NO 58
<211> LENGTH: 18
<212> TYPE: DNA
<213> ORGANISM: Artificial Sequence
<220> FEATURE:
<223> OTHER INFORMATION: Human immunodeficiency virus envelope
      degenerate loop B primer

<400> SEQUENCE: 58
acacaygcct gtgtaccm                                                  18

<210> SEQ ID NO 59
<211> LENGTH: 225
<212> TYPE: DNA
<213> ORGANISM: Artificial Sequence
<220> FEATURE:
<223> OTHER INFORMATION: genome location 1311 - 1535 within HXB2
      reference strain

<400> SEQUENCE: 59
attatcagaa ggagccaccc cacaagattt aaacaccatg ctaaacacag tggggggaca     60
tcaagcagcc atgcaaatgt taaagaaaac catcaatgag gaagctgcag aatgggatag    120
attgcatccc gtgcaggcag ggcctgttgc accaggccag ataagagatc caaggggaag    180
tgacatagca ggaactacca gtacccttca ggaacaaata ggatg                    225

<210> SEQ ID NO 60
<211> LENGTH: 211
<212> TYPE: DNA
<213> ORGANISM: Artificial Sequence
<220> FEATURE:
<223> OTHER INFORMATION: genome location 2291 - 2501 within HXB2
      reference strain

<400> SEQUENCE: 60
aaagataggg gggcaactaa aggaagctct attagataca ggagcagatg atacagtatt     60
agaagaaata aatttgccag gaagatggaa accaaaaatg ataggggaa ttggaggttt     120 tatcaaagta agacagtatg atcagatact catagaaatc tgtggacata aagctatagg    180
tacagtatta ataggaccta cacctgtcaa c                                   211

<210> SEQ ID NO 61
<211> LENGTH: 192
<212> TYPE: DNA
<213> ORGANISM: Artificial Sequence
<220> FEATURE:
<223> OTHER INFORMATION: genome location 6321 - 6512 within HXB2
      reference strain

<400> SEQUENCE: 61
aaattgtggg tcacagtcta ttatggggta cctgtgtgga aagaagcaac caccactcta     60
ttttgtgcat cagatgctaa agcatatgat acagaggtac ataatgtttg ggccacacat    120
gcctgtgtac ccacagaccc caacccacaa gaagtagtat tggaaaatgt gacagaaaat    180
tttaacatgt gg                                                        192

```
<210> SEQ ID NO 62
<211> LENGTH: 191
<212> TYPE: DNA
<213> ORGANISM: Artificial Sequence
<220> FEATURE:
<223> OTHER INFORMATION: genome location 4283 - 4474 within HXB2
      reference strain

<400> SEQUENCE: 62
ttggagagca atggctagtg attttaacct gcacctgtgg tagcaaaaga aatagtagcc    60
agctgtgata aatgtcagct aaaaggagaa gccatgcatg gacaagtaga ctgtagtcca   120
ggaatatggc aactagattg tacacattta gaaggaaaaa ttatcctggt agcagttcat   180
gtagccagtg g                                                        191

<210> SEQ ID NO 63
<211> LENGTH: 198
<212> TYPE: DNA
<213> ORGANISM: Artificial Sequence
<220> FEATURE:
<223> OTHER INFORMATION: genome location 3488 - 3685 within MAC239
      reference strain

<400> SEQUENCE: 63
ggattttcta ccccagatga aagttccaa aaggaccctc ataccactg gatgggctat     60 gaactgtggc caactaagtg gaagctgcag aagatacagt tgccccaaaa agatgtatgg  120
acagtaaatg acatccaaaa gttagtgggt gtcttaaact gggcagcaca aatctaccca  180
gggataaaaa ccagacac                                                 198

<210> SEQ ID NO 64
<211> LENGTH: 10
<212> TYPE: DNA
<213> ORGANISM: Artificial Sequence
<220> FEATURE:
<223> OTHER INFORMATION: linker
<220> FEATURE:
<221> NAME/KEY: misc_feature
<222> LOCATION: (1)..(3)
<223> OTHER INFORMATION: Primer sequence
<220> FEATURE:
<221> NAME/KEY: misc_feature
<222> LOCATION: (8)..(10)
<223> OTHER INFORMATION: Primer sequence

<400> SEQUENCE: 64 nnnttttnnn                                                          10

<210> SEQ ID NO 65
<211> LENGTH: 23
<212> TYPE: DNA
<213> ORGANISM: Artificial Sequence
<220> FEATURE:
<223> OTHER INFORMATION: Human immunodeficiency virus P24 degenerate
      FIP primer portion

<400> SEQUENCE: 65
cagcytcctc attgatggtt tct                                           23

<210> SEQ ID NO 66
<211> LENGTH: 20
<212> TYPE: DNA
<213> ORGANISM: Artificial Sequence
<220> FEATURE:
<223> OTHER INFORMATION: Human immunodeficiency virus P24 degenerate
      FIP primer portion
```

<400> SEQUENCE: 66
aacaccatgy taaayayagt                                         20

<210> SEQ ID NO 67
<211> LENGTH: 20
<212> TYPE: DNA
<213> ORGANISM: Artificial Sequence
<220> FEATURE:
<223> OTHER INFORMATION: Human immunodeficiency virus P24 degenerate
      BIP primer portion

<400> SEQUENCE: 67
trttgcacca ggccagatra                                         20

<210> SEQ ID NO 68
<211> LENGTH: 21
<212> TYPE: DNA
<213> ORGANISM: Artificial Sequence
<220> FEATURE:
<223> OTHER INFORMATION: Human immunodeficiency virus P24 degenerate
      BIP primer portion

<400> SEQUENCE: 68
gtactwgtag ttcctgctat r                                       21

<210> SEQ ID NO 69
<211> LENGTH: 23
<212> TYPE: DNA
<213> ORGANISM: Artificial Sequence
<220> FEATURE:
<223> OTHER INFORMATION: Human immunodeficiency virus protease
      degenerate FIP primer portion

<400> SEQUENCE: 69
ggtttccaty tycctggcaa att                                     23

<210> SEQ ID NO 70
<211> LENGTH: 22
<212> TYPE: DNA
<213> ORGANISM: Artificial Sequence
<220> FEATURE:
<223> OTHER INFORMATION: Human immunodeficiency virus protease
      degenerate FIP primer portion

<400> SEQUENCE: 70
ckctattaga yacaggagca ga                                      22

<210> SEQ ID NO 71
<211> LENGTH: 22
<212> TYPE: DNA
<213> ORGANISM: Artificial Sequence
<220> FEATURE:
<223> OTHER INFORMATION: Human immunodeficiency virus protease
      degenerate BIP primer portion

<400> SEQUENCE: 71
tgataggggg aattggaggt tt                                      22

<210> SEQ ID NO 72
<211> LENGTH: 22
<212> TYPE: DNA
<213> ORGANISM: Artificial Sequence
<220> FEATURE:
<223> OTHER INFORMATION: Human immunodeficiency virus protease
      degenerate BIP primer portion

<400> SEQUENCE: 72

```
cctatagcyt twtktccaca ra                                          22

<210> SEQ ID NO 73
<211> LENGTH: 24
<212> TYPE: DNA
<213> ORGANISM: Artificial Sequence
<220> FEATURE:
<223> OTHER INFORMATION: Human immunodeficiency virus envelope
      degenerate FIP primer portion

<400> SEQUENCE: 73
tyatatgctt tagcatctga tgca                                        24

<210> SEQ ID NO 74
<211> LENGTH: 18
<212> TYPE: DNA
<213> ORGANISM: Artificial Sequence
<220> FEATURE:
<223> OTHER INFORMATION: Human immunodeficiency virus envelope
      degenerate FIP primer portion

<400> SEQUENCE: 74
gggtacctgt gtggarag                                               18

<210> SEQ ID NO 75
<211> LENGTH: 23
<212> TYPE: DNA
<213> ORGANISM: Artificial Sequence
<220> FEATURE:
<223> OTHER INFORMATION: Human immunodeficiency virus envelope
      degenerate BIP primer portion

<400> SEQUENCE: 75
cagargtrca taatgtytgg gcy                                         23

<210> SEQ ID NO 76
<211> LENGTH: 19
<212> TYPE: DNA
<213> ORGANISM: Artificial Sequence
<220> FEATURE:
<223> OTHER INFORMATION: Human immunodeficiency virus envelope
      degenerate BIP primer portion

<400> SEQUENCE: 76
wctayttctt gtgggttgg                                              19

<210> SEQ ID NO 77
<211> LENGTH: 41
<212> TYPE: DNA
<213> ORGANISM: Artificial Sequence
<220> FEATURE:
<223> OTHER INFORMATION: Human immunodeficiency virus P24 BIP primer
      optimized for clades FGE
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 77
tatcccacca ggccagataa gtactagtag ttcctgctat a                     41

<210> SEQ ID NO 78
<211> LENGTH: 19
<212> TYPE: DNA
<213> ORGANISM: Artificial Sequence
<220> FEATURE:
```

<223> OTHER INFORMATION: Human immunodeficiency virus P24 loop B primer
      optimized for clades FGE

<400> SEQUENCE: 78
gagaaccaag gggaagtga                                                    19

<210> SEQ ID NO 79
<211> LENGTH: 20
<212> TYPE: DNA
<213> ORGANISM: Artificial Sequence
<220> FEATURE:
<223> OTHER INFORMATION: Human immunodeficiency virus polymerase F3
      primer

<400> SEQUENCE: 79
ggattctcta ccccagatga                                                   20

<210> SEQ ID NO 80
<211> LENGTH: 20
<212> TYPE: DNA
<213> ORGANISM: Artificial Sequence
<220> FEATURE:
<223> OTHER INFORMATION: Human immunodeficiency virus polymerase B3
      primer

<400> SEQUENCE: 80
gtgtttggtc tttatccctg                                                   20

<210> SEQ ID NO 81
<211> LENGTH: 42
<212> TYPE: DNA
<213> ORGANISM: Artificial Sequence
<220> FEATURE:
<223> OTHER INFORMATION: Human immunodeficiency virus polymerase FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 81
ttccatttag ttggccatag ttcgaagttc caaaaagacc ct                          42

<210> SEQ ID NO 82
<211> LENGTH: 44
<212> TYPE: DNA
<213> ORGANISM: Artificial Sequence
<220> FEATURE:
<223> OTHER INFORMATION: Human immunodeficiency virus polymerase BIP
      primer
<220> FEATURE:
<221> NAME/KEY: misc_feature
<222> LOCATION: (25)..(25)
<223> OTHER INFORMATION: A linker is present between nucleotides 24 and
      25.

<400> SEQUENCE: 82
gaagatacag ttgccccaaa aagaccaatt taggacaccc acta                        44

<210> SEQ ID NO 83
<211> LENGTH: 19
<212> TYPE: DNA
<213> ORGANISM: Artificial Sequence
<220> FEATURE:
<223> OTHER INFORMATION: Human immunodeficiency virus polymerase loop F
      primer

<400> SEQUENCE: 83
agcccatcca gtggtatgg                                                    19

<210> SEQ ID NO 84
<211> LENGTH: 25
<212> TYPE: DNA
<213> ORGANISM: Artificial Sequence
<220> FEATURE:
<223> OTHER INFORMATION: Human immunodeficiency virus polymerase loop B
      primer

<400> SEQUENCE: 84
tgtatggaca gtaaatgaca tccaa                                             25

<210> SEQ ID NO 85
<211> LENGTH: 20
<212> TYPE: DNA
<213> ORGANISM: Artificial Sequence
<220> FEATURE:
<223> OTHER INFORMATION: Human immunodeficiency virus P24 BIP primer
      portion optimized for clades FGE

<400> SEQUENCE: 85
tatcccacca ggccagataa                                                   20

<210> SEQ ID NO 86
<211> LENGTH: 21
<212> TYPE: DNA
<213> ORGANISM: Artificial Sequence
<220> FEATURE:
<223> OTHER INFORMATION: Human immunodeficiency virus P24 BIP primer
      portion optimized for clades FGE

<400> SEQUENCE: 86
gtactagtag ttcctgctat a                                                 21

<210> SEQ ID NO 87
<211> LENGTH: 23
<212> TYPE: DNA
<213> ORGANISM: Artificial Sequence
<220> FEATURE:
<223> OTHER INFORMATION: Human immunodeficiency virus polymerase FIP
      primer portion

<400> SEQUENCE: 87
ttccatttag ttggccatag ttc                                               23

<210> SEQ ID NO 88
<211> LENGTH: 19
<212> TYPE: DNA
<213> ORGANISM: Artificial Sequence
<220> FEATURE:
<223> OTHER INFORMATION: Human immunodeficiency virus polymerase FIP
      primer portion

<400> SEQUENCE: 88
gaagttccaa aaagaccct                                                    19

<210> SEQ ID NO 89
<211> LENGTH: 24
<212> TYPE: DNA
<213> ORGANISM: Artificial Sequence
<220> FEATURE:
<223> OTHER INFORMATION: Human immunodeficiency virus polymerase BIP
      primer portion

<400> SEQUENCE: 89
gaagatacag ttgccccaaa aaga                                          24

<210> SEQ ID NO 90
<211> LENGTH: 20
<212> TYPE: DNA
<213> ORGANISM: Artificial Sequence
<220> FEATURE:
<223> OTHER INFORMATION: Human immunodeficiency virus polymerase BIP
      primer portion

<400> SEQUENCE: 90
ccaatttagg acacccacta                                               20

<210> SEQ ID NO 91
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 91
attagcagaa ggagccacc                                                19

<210> SEQ ID NO 92
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 92
attagcagaa ggagccact                                                19

<210> SEQ ID NO 93
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 93
attagcagaa ggagccatc                                                19

<210> SEQ ID NO 94
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 94
attagcagaa ggagccatt                                                19

<210> SEQ ID NO 95
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 95
attagcagag ggagccacc                                                19

<210> SEQ ID NO 96
<211> LENGTH: 19
<212> TYPE: DNA

```
<213> ORGANISM: Artificial Sequence
<220> FEATURE:
<223> OTHER INFORMATION: Human immunodeficiency virus P24 F3 primer

<400> SEQUENCE: 96
attagcagag ggagccact                                                 19

<210> SEQ ID NO 97
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 97
attagcagag ggagccatc                                                 19

<210> SEQ ID NO 98
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 98
attagcagag ggagccatt                                                 19

<210> SEQ ID NO 99
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 99
attatcagaa ggagccacc                                                 19

<210> SEQ ID NO 100
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 100
attatcagaa ggagccact                                                 19

<210> SEQ ID NO 101
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 101
attatcagaa ggagccatc                                                 19

<210> SEQ ID NO 102
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 102
attatcagaa ggagccatt                                                 19
```

<210> SEQ ID NO 103
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 103
attatcagag ggagccacc                                                  19

<210> SEQ ID NO 104
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 104
attatcagag ggagccact                                                  19

<210> SEQ ID NO 105
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 105
attatcagag ggagccatc                                                  19

<210> SEQ ID NO 106
<211> LENGTH: 19
<212> TYPE: DNA
<213> ORGANISM: Artificial Sequence
<220> FEATURE:
<223> OTHER INFORMATION: Human immunodeficiency virus P24 F3 primer

<400> SEQUENCE: 106
attatcagag ggagccatt                                                  19

<210> SEQ ID NO 107
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 107
catcctattt gctcctgaag a                                               21

<210> SEQ ID NO 108
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 108
catcctattt gctcctgaag g                                               21

<210> SEQ ID NO 109
<211> LENGTH: 21
<212> TYPE: DNA
<213> ORGANISM: Artificial Sequence
<220> FEATURE:

-continued

<223> OTHER INFORMATION: Human immunodeficiency virus P24 B3 primer

<400> SEQUENCE: 109
catcctattt gctcctgagg a                                              21

<210> SEQ ID NO 110
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 110
catcctattt gctcctgagg g                                              21

<210> SEQ ID NO 111
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 111
catcctattt gttcctgaag a                                              21

<210> SEQ ID NO 112
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 112
catcctattt gttcctgaag g                                              21

<210> SEQ ID NO 113
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 113
catcctattt gttcctgagg a                                              21

<210> SEQ ID NO 114
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 114
catcctattt gttcctgagg g                                              21

<210> SEQ ID NO 115
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 115
catgctattt gctcctgaag a                                              21

```
<210> SEQ ID NO 116
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 116
catgctattt gctcctgaag g                                              21

<210> SEQ ID NO 117
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 117
catgctattt gctcctgagg a                                              21

<210> SEQ ID NO 118
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 118
catgctattt gctcctgagg g                                              21

<210> SEQ ID NO 119
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 119
catgctattt gttcctgaag a                                              21

<210> SEQ ID NO 120
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 120
catgctattt gttcctgaag g                                              21

<210> SEQ ID NO 121
<211> LENGTH: 21
<212> TYPE: DNA
<213> ORGANISM: Artificial Sequence
<220> FEATURE:
<223> OTHER INFORMATION: Human immunodeficiency virus P24 B3 primer

<400> SEQUENCE: 121
catgctattt gttcctgagg a                                              21

<210> SEQ ID NO 122
<211> LENGTH: 21
<212> TYPE: DNA
<213> ORGANISM: Artificial Sequence
<220> FEATURE:
<223> OTHER INFORMATION: Human immunodeficiency virus P24 B3 primer
```

<400> SEQUENCE: 122
catgctattt gttcctgagg g                                        21

<210> SEQ ID NO 123
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 123
cagcctcctc attgatggtt tctaacacca tgctaaacac agt                43

<210> SEQ ID NO 124
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 124
cagcctcctc attgatggtt tctaacacca tgctaaacat agt                43

<210> SEQ ID NO 125
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 125
cagcctcctc attgatggtt tctaacacca tgctaaatac agt                43

<210> SEQ ID NO 126
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 126
cagcctcctc attgatggtt tctaacacca tgctaaatat agt                43

<210> SEQ ID NO 127
<211> LENGTH: 43
<212> TYPE: DNA
<213> ORGANISM: Artificial Sequence
<220> FEATURE:
<223> OTHER INFORMATION: Human immunodeficiency virus P24 FIP primer

```
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 127
cagcctcctc attgatggtt tctaacacca tgttaaacac agt                    43

<210> SEQ ID NO 128
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 128
cagcctcctc attgatggtt tctaacacca tgttaaacat agt                    43

<210> SEQ ID NO 129
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 129
cagcctcctc attgatggtt tctaacacca tgttaaatac agt                    43

<210> SEQ ID NO 130
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 130
cagcctcctc attgatggtt tctaacacca tgttaaatat agt                    43

<210> SEQ ID NO 131
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 131
cagcttcctc attgatggtt tctaacacca tgctaaacac agt                    43
```

```
<210> SEQ ID NO 132
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 132
cagcttcctc attgatggtt tctaacacca tgctaaacat agt                   43

<210> SEQ ID NO 133
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 133
cagcttcctc attgatggtt tctaacacca tgctaaatac agt                   43

<210> SEQ ID NO 134
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 134
cagcttcctc attgatggtt tctaacacca tgctaaatat agt                   43

<210> SEQ ID NO 135
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 135
cagcttcctc attgatggtt tctaacacca tgttaaacac agt                   43

<210> SEQ ID NO 136
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.
```

<400> SEQUENCE: 136
cagcttcctc attgatggtt tctaacacca tgttaaacat agt                                43

<210> SEQ ID NO 137
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 137
cagcttcctc attgatggtt tctaacacca tgttaaatac agt                                43

<210> SEQ ID NO 138
<211> LENGTH: 43
<212> TYPE: DNA
<213> ORGANISM: Artificial Sequence
<220> FEATURE:
<223> OTHER INFORMATION: Human immunodeficiency virus P24 FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 138
cagcttcctc attgatggtt tctaacacca tgttaaatat agt                                43

<210> SEQ ID NO 139
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 139
tattgcacca ggccagataa gtactagtag ttcctgctat a                                  41

<210> SEQ ID NO 140
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 140
tattgcacca ggccagataa gtactagtag ttcctgctat g                                  41

<210> SEQ ID NO 141
<211> LENGTH: 41
<212> TYPE: DNA
<213> ORGANISM: Artificial Sequence
<220> FEATURE:

```
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 141
tattgcacca ggccagataa gtacttgtag ttcctgctat a                              41

<210> SEQ ID NO 142
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 142
tattgcacca ggccagataa gtacttgtag ttcctgctat g                              41

<210> SEQ ID NO 143
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 143
tattgcacca ggccagatga gtactagtag ttcctgctat a                              41

<210> SEQ ID NO 144
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 144
tattgcacca ggccagatga gtactagtag ttcctgctat g                              41

<210> SEQ ID NO 145
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 145
tattgcacca ggccagatga gtacttgtag ttcctgctat a                              41
```

<210> SEQ ID NO 146
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and 21.

<400> SEQUENCE: 146
tattgcacca ggccagatga gtacttgtag ttcctgctat g        41

<210> SEQ ID NO 147
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and 21.

<400> SEQUENCE: 147
tgttgcacca ggccagataa gtactagtag ttcctgctat a        41

<210> SEQ ID NO 148
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and 21.

<400> SEQUENCE: 148
tgttgcacca ggccagataa gtactagtag ttcctgctat g        41

<210> SEQ ID NO 149
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and 21.

<400> SEQUENCE: 149
tgttgcacca ggccagataa gtacttgtag ttcctgctat a        41

<210> SEQ ID NO 150
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and -continued

21.

<400> SEQUENCE: 150
tgttgcacca ggccagataa gtacttgtag ttcctgctat g                41

<210> SEQ ID NO 151
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 151
tgttgcacca ggccagatga gtactagtag ttcctgctat a                41

<210> SEQ ID NO 152
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 152
tgttgcacca ggccagatga gtactagtag ttcctgctat g                41

<210> SEQ ID NO 153
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 153
tgttgcacca ggccagatga gtacttgtag ttcctgctat a                41

<210> SEQ ID NO 154
<211> LENGTH: 41
<212> TYPE: DNA
<213> ORGANISM: Artificial Sequence
<220> FEATURE:
<223> OTHER INFORMATION: Human immunodeficiency virus P24 BIP primer
<220> FEATURE:
<221> NAME/KEY: misc_feature
<222> LOCATION: (21)..(21)
<223> OTHER INFORMATION: A linker is present between nucleotides 20 and
      21.

<400> SEQUENCE: 154
tgttgcacca ggccagatga gtacttgtag ttcctgctat g                41

<210> SEQ ID NO 155
<211> LENGTH: 24
<212> TYPE: DNA
<213> ORGANISM: Artificial Sequence

```
<220> FEATURE:
<223> OTHER INFORMATION: Human immunodeficiency virus P24 loop F primer

<400> SEQUENCE: 155
tttaacatct gcatagctgc ctga                                          24

<210> SEQ ID NO 156
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 156
tttaacatct gcatagctgc ctgg                                          24

<210> SEQ ID NO 157
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 157
tttaacatct gcatagctgc ttga                                          24

<210> SEQ ID NO 158
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 158
tttaacatct gcatagctgc ttgg                                          24

<210> SEQ ID NO 159
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 159
tttaacatct gcatggctgc ctga                                          24

<210> SEQ ID NO 160
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 160
tttaacatct gcatggctgc ctgg                                          24

<210> SEQ ID NO 161
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 161
tttaacatct gcatggctgc ttga                                          24
```

```
<210> SEQ ID NO 162
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 162
tttaacatct gcatggctgc ttgg                                          24

<210> SEQ ID NO 163
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 163
tttaacattt gcatagctgc ctga                                          24

<210> SEQ ID NO 164
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 164
tttaacattt gcatagctgc ctgg                                          24

<210> SEQ ID NO 165
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 165
tttaacattt gcatagctgc ttga                                          24

<210> SEQ ID NO 166
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 166
tttaacattt gcatagctgc ttgg                                          24

<210> SEQ ID NO 167
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 167 tttaacatttt gcatggctgc ctga                                         24

<210> SEQ ID NO 168
<211> LENGTH: 24
<212> TYPE: DNA
<213> ORGANISM: Artificial Sequence
<220> FEATURE:
<223> OTHER INFORMATION: Human immunodeficiency virus P24 loop F primer
```

-continued

<400> SEQUENCE: 168
tttaacattt gcatggctgc ctgg                                          24

<210> SEQ ID NO 169
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 169
tttaacattt gcatggctgc ttga                                          24

<210> SEQ ID NO 170
<211> LENGTH: 24
<212> TYPE: DNA
<213> ORGANISM: Artificial Sequence
<220> FEATURE:
<223> OTHER INFORMATION: Human immunodeficiency virus P24 loop F primer

<400> SEQUENCE: 170
tttaacattt gcatggctgc ttgg                                          24

<210> SEQ ID NO 171
<211> LENGTH: 19
<212> TYPE: DNA
<213> ORGANISM: Artificial Sequence
<220> FEATURE:
<223> OTHER INFORMATION: Human immunodeficiency virus P24 loop B primer

<400> SEQUENCE: 171
gagaaccaag gggaagtga                                                19

<210> SEQ ID NO 172
<211> LENGTH: 19
<212> TYPE: DNA
<213> ORGANISM: Artificial Sequence
<220> FEATURE:
<223> OTHER INFORMATION: Human immunodeficiency virus P24 loop B primer

<400> SEQUENCE: 172
gagacccaag gggaagtga                                                19

<210> SEQ ID NO 173
<211> LENGTH: 19
<212> TYPE: DNA
<213> ORGANISM: Artificial Sequence
<220> FEATURE:
<223> OTHER INFORMATION: Human immunodeficiency virus P24 loop B primer

<400> SEQUENCE: 173
gggaaccaag gggaagtga                                                19

<210> SEQ ID NO 174
<211> LENGTH: 19
<212> TYPE: DNA
<213> ORGANISM: Artificial Sequence
<220> FEATURE:
<223> OTHER INFORMATION: Human immunodeficiency virus P24 loop B primer

<400> SEQUENCE: 174
gggacccaag gggaagtga                                                19

<210> SEQ ID NO 175

```
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 175
aaaaataggg ggacaact                                                    18

<210> SEQ ID NO 176
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 176
aaaaataggg ggacagct                                                    18

<210> SEQ ID NO 177
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 177
aaaaataggg gggcaact                                                    18

<210> SEQ ID NO 178
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 178
aaaaataggg gggcagct                                                    18

<210> SEQ ID NO 179
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 179
aaagataggg ggacaact                                                    18

<210> SEQ ID NO 180
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 180
aaagataggg ggacagct                                                    18

<210> SEQ ID NO 181
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 181
```

```
aaagataggg gggcaact                                                      18

<210> SEQ ID NO 182
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 182
aaagataggg gggcagct                                                      18

<210> SEQ ID NO 183
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 183
aagaataggg ggacaact                                                      18

<210> SEQ ID NO 184
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 184
aagaataggg ggacagct                                                      18

<210> SEQ ID NO 185
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 185
aagaataggg gggcaact                                                      18

<210> SEQ ID NO 186
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 186
aagaataggg gggcagct                                                      18

<210> SEQ ID NO 187
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 187
aaggataggg ggacaact                                                      18

<210> SEQ ID NO 188
<211> LENGTH: 18
<212> TYPE: DNA
```

<213> ORGANISM: Artificial Sequence
<220> FEATURE:
<223> OTHER INFORMATION: Human immunodeficiency virus protease F3 primer

<400> SEQUENCE: 188
aaggataggg ggacagct					18

<210> SEQ ID NO 189
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 189
aaggataggg gggcaact					18

<210> SEQ ID NO 190
<211> LENGTH: 18
<212> TYPE: DNA
<213> ORGANISM: Artificial Sequence
<220> FEATURE:
<223> OTHER INFORMATION: Human immunodeficiency virus protease F3 primer

<400> SEQUENCE: 190
aaggataggg gggcagct					18

<210> SEQ ID NO 191
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 191
gttgacaggg gtaggtccaa					20

<210> SEQ ID NO 192
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 192
gttgacaggg gtaggtccga					20

<210> SEQ ID NO 193
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 193
gttgacaggg gtaggtccta					20

<210> SEQ ID NO 194
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 194
gttgacaggt gtaggtccaa					20

<210> SEQ ID NO 195
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 195
gttgacaggt gtaggtccga                                           20

<210> SEQ ID NO 196
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 196
gttgacaggt gtaggtccta                                           20

<210> SEQ ID NO 197
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 197
gttgacgggg gtaggtccaa                                           20

<210> SEQ ID NO 198
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 198
gttgacgggg gtaggtccga                                           20

<210> SEQ ID NO 199
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 199
gttgacgggg gtaggtccta                                           20

<210> SEQ ID NO 200
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 200
gttgacgggt gtaggtccaa                                           20

<210> SEQ ID NO 201
<211> LENGTH: 20
<212> TYPE: DNA
<213> ORGANISM: Artificial Sequence
<220> FEATURE:

<223> OTHER INFORMATION: Human immunodeficiency virus protease B3 primer

<400> SEQUENCE: 201
gttgacgggt gtaggtccga                                                 20

<210> SEQ ID NO 202
<211> LENGTH: 20
<212> TYPE: DNA
<213> ORGANISM: Artificial Sequence
<220> FEATURE:
<223> OTHER INFORMATION: Human immunodeficiency virus protease B3 primer

<400> SEQUENCE: 202
gttgacgggt gtaggtccta                                                 20

<210> SEQ ID NO 203
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 203
ggtttccatc tccctggcaa attcgctatt agacacagga gcaga                     45

<210> SEQ ID NO 204
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 204
ggtttccatc tccctggcaa attcgctatt agatacagga gcaga                     45

<210> SEQ ID NO 205
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 205
ggtttccatc tccctggcaa attctctatt agacacagga gcaga                     45

<210> SEQ ID NO 206
<211> LENGTH: 45
<212> TYPE: DNA
<213> ORGANISM: Artificial Sequence
<220> FEATURE:
<223> OTHER INFORMATION: Human immunodeficiency virus protease FIP primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 206
ggtttccatc tccctggcaa attctctatt agatacagga gcaga                     45

<210> SEQ ID NO 207
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 207
ggtttccatc ttcctggcaa attcgctatt agacacagga gcaga                     45

<210> SEQ ID NO 208
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 208
ggtttccatc ttcctggcaa attcgctatt agatacagga gcaga                     45

<210> SEQ ID NO 209
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 209
ggtttccatc ttcctggcaa attctctatt agacacagga gcaga                     45

<210> SEQ ID NO 210
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 210
ggtttccatc ttcctggcaa attctctatt agatacagga gcaga                45

<210> SEQ ID NO 211
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 211
ggtttccatt tccctggcaa attcgctatt agacacagga gcaga                45

<210> SEQ ID NO 212
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 212
ggtttccatt tccctggcaa attcgctatt agatacagga gcaga                45

<210> SEQ ID NO 213
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 213
ggtttccatt tccctggcaa attctctatt agacacagga gcaga                45

<210> SEQ ID NO 214
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 214
ggtttccatt tccctggcaa attctctatt agatacagga gcaga                45

<210> SEQ ID NO 215
<211> LENGTH: 45

<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 215
ggtttccatt ttcctggcaa attcgctatt agacacagga gcaga          45

<210> SEQ ID NO 216
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 216
ggtttccatt ttcctggcaa attcgctatt agatacagga gcaga          45

<210> SEQ ID NO 217
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 217
ggtttccatt ttcctggcaa attctctatt agacacagga gcaga          45

<210> SEQ ID NO 218
<211> LENGTH: 45
<212> TYPE: DNA
<213> ORGANISM: Artificial Sequence
<220> FEATURE:
<223> OTHER INFORMATION: Human immunodeficiency virus protease FIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 218
ggtttccatt ttcctggcaa attctctatt agatacagga gcaga          45

<210> SEQ ID NO 219
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature

```
<222> LOCATION: (23)..(23)
<223> OTHER INFORMATION: A linker is present between nucleotides 22 and
      23.

<400> SEQUENCE: 219
tgataggagg aattggaggt ttcctatagc cttatgtcca caaa                    44

<210> SEQ ID NO 220
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 220
tgataggagg aattggaggt ttcctatagc cttatgtcca caga                    44

<210> SEQ ID NO 221
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 221
tgataggagg aattggaggt ttcctatagc cttatttcca caaa                    44

<210> SEQ ID NO 222
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 222
tgataggagg aattggaggt ttcctatagc cttatttcca caga                    44

<210> SEQ ID NO 223
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 223
tgataggagg aattggaggt ttcctatagc cttttgtcca caaa                    44
```

```
<210> SEQ ID NO 224
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 224
tgataggagg aattggaggt ttcctatagc cttttgtcca caga                44

<210> SEQ ID NO 225
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 225
tgataggagg aattggaggt ttcctatagc cttttttcca caaa                44

<210> SEQ ID NO 226
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 226
tgataggagg aattggaggt ttcctatagc cttttttcca caga                44

<210> SEQ ID NO 227
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 227
tgataggagg aattggaggt ttcctatagc tttatgtcca caaa                44

<210> SEQ ID NO 228
<211> LENGTH: 44
<212> TYPE: DNA
<213> ORGANISM: Artificial Sequence
<220> FEATURE:
```

-continued

<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 228
tgataggagg aattggaggt ttcctatagc tttatgtcca caga                    44

<210> SEQ ID NO 229
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 229
tgataggagg aattggaggt ttcctatagc tttatttcca caaa                    44

<210> SEQ ID NO 230
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 230
tgataggagg aattggaggt ttcctatagc tttatttcca caga                    44

<210> SEQ ID NO 231
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 231
tgataggagg aattggaggt ttcctatagc tttttgtcca caaa                    44

<210> SEQ ID NO 232
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

```
<400> SEQUENCE: 232
tgataggagg aattggaggt ttcctatagc tttttgtcca caga                  44

<210> SEQ ID NO 233
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE
<221> NAME/KEY: misc_feature
<222> LOCATION: (23)..(23)
<223> OTHER INFORMATION: A linker is present between nucleotides 22 and
      23.

<400> SEQUENCE: 233
tgataggagg aattggaggt ttcctatagc tttttttcca caaa                  44

<210> SEQ ID NO 234
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 234
tgataggagg aattggaggt ttcctatagc tttttttcca caga                  44

<210> SEQ ID NO 235
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 235
tgataggggg aattggaggt ttcctatagc cttatgtcca caaa                  44

<210> SEQ ID NO 236
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 236
tgataggggg aattggaggt ttcctatagc cttatgtcca caga                  44

<210> SEQ ID NO 237
```

```
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 237
tgataggggg aattggaggt ttcctatagc cttatttcca caaa              44

<210> SEQ ID NO 238
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 238
tgataggggg aattggaggt ttcctatagc cttatttcca caga              44

<210> SEQ ID NO 239
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 239
tgataggggg aattggaggt ttcctatagc cttttgtcca caaa              44

<210> SEQ ID NO 240
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 240
tgataggggg aattggaggt ttcctatagc cttttgtcca caga              44

<210> SEQ ID NO 241
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
```

```
<221> NAME/KEY: misc_feature
<222> LOCATION: (23)..(23)
<223> OTHER INFORMATION: A linker is present between nucleotides 22 and
      23.

<400> SEQUENCE: 241
tgataggggg aattggaggt ttcctatagc cttttttcca caaa                    44

<210> SEQ ID NO 242
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 242
tgataggggg aattggaggt ttcctatagc cttttttcca caga                    44

<210> SEQ ID NO 243
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 243
tgataggggg aattggaggt ttcctatagc tttatgtcca caaa                    44

<210> SEQ ID NO 244
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 244
tgataggggg aattggaggt ttcctatagc tttatgtcca caga                    44

<210> SEQ ID NO 245
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 245
``` tgatagggggg aattggaggt ttcctatagc tttatttcca caaa        44

<210> SEQ ID NO 246
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 246 tgatagggggg aattggaggt ttcctatagc tttatttcca caga        44

<210> SEQ ID NO 247
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 247 tgatagggggg aattggaggt ttcctatagc tttttgtcca caaa        44

<210> SEQ ID NO 248
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 248 tgatagggggg aattggaggt ttcctatagc tttttgtcca caga        44

<210> SEQ ID NO 249
<211> LENGTH: 44
<212> TYPE: DNA
<213> ORGANISM: Artificial Sequence
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 249 tgatagggggg aattggaggt ttcctatagc ttttttttcca caaa        44

<210> SEQ ID NO 250
<211> LENGTH: 44
<212> TYPE: DNA
<213> ORGANISM: Artificial Sequence

```
<220> FEATURE:
<223> OTHER INFORMATION: Human immunodeficiency virus protease BIP
      primer
<220> FEATURE:
<221> NAME/KEY: misc_feature
<222> LOCATION: (23)..(23)
<223> OTHER INFORMATION: A linker is present between nucleotides 22 and
      23.

<400> SEQUENCE: 250
tgataggggg aattggaggt ttcctatagc ttttttccca caga                      44

<210> SEQ ID NO 251
<211> LENGTH: 22
<212> TYPE: DNA
<213> ORGANISM: Artificial Sequence
<220> FEATURE:
<223> OTHER INFORMATION: Human immunodeficiency virus protease loop F
      primer

<400> SEQUENCE: 251
catgtcttct aatactgtat ca                                              22

<210> SEQ ID NO 252
<211> LENGTH: 22
<212> TYPE: DNA
<213> ORGANISM: Artificial Sequence
<220> FEATURE:
<223> OTHER INFORMATION: Human immunodeficiency virus protease loop F
      primer

<400> SEQUENCE: 252
catttcttct aatactgtat ca                                              22

<210> SEQ ID NO 253
<211> LENGTH: 22
<212> TYPE: DNA
<213> ORGANISM: Artificial Sequence
<220> FEATURE:
<223> OTHER INFORMATION: Human immunodeficiency virus protease loop F
      primer

<400> SEQUENCE: 253
tatgtcttct aatactgtat ca                                              22

<210> SEQ ID NO 254
<211> LENGTH: 22
<212> TYPE: DNA
<213> ORGANISM: Artificial Sequence
<220> FEATURE:
<223> OTHER INFORMATION: Human immunodeficiency virus protease loop F
      primer

<400> SEQUENCE: 254
tatttcttct aatactgtat ca                                              22

<210> SEQ ID NO 255
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 255
tatcaaagta aaacaata                                                   18
```

-continued

<210> SEQ ID NO 256
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 256
tatcaaagta aaacagta                                                 18

<210> SEQ ID NO 257
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 257
tatcaaagta agacaata                                                 18

<210> SEQ ID NO 258
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 258
tatcaaagta agacagta                                                 18

<210> SEQ ID NO 259
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 259
tatcaaggta aaacaata                                                 18

<210> SEQ ID NO 260
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 260
tatcaaggta aaacagta                                                 18

<210> SEQ ID NO 261
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 261
tatcaaggta agacaata                                                 18

<210> SEQ ID NO 262

```
<211> LENGTH: 18
<212> TYPE: DNA
<213> ORGANISM: Artificial Sequence
<220> FEATURE:
<223> OTHER INFORMATION: Human immunodeficiency virus protease loop F
      primer

<400> SEQUENCE: 262
tatcaaggta agacagta                                                 18

<210> SEQ ID NO 263
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 263
aaattgtggg tcacagtat                                                19

<210> SEQ ID NO 264
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 264
aaattgtggg tcacagtct                                                19

<210> SEQ ID NO 265
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 265
aaattgtggg tcacagttt                                                19

<210> SEQ ID NO 266
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 266
aacttgtggg tcacagtat                                                19

<210> SEQ ID NO 267
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 267
aacttgtggg tcacagtct                                                19

<210> SEQ ID NO 268
<211> LENGTH: 19
<212> TYPE: DNA
<213> ORGANISM: Artificial Sequence
<220> FEATURE:
<223> OTHER INFORMATION: Human immunodeficiency virus envelope F3 primer
```

<400> SEQUENCE: 268
aacttgtggg tcacagttt                                                    19

<210> SEQ ID NO 269
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 269
aatttgtggg tcacagtat                                                    19

<210> SEQ ID NO 270
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 270
aatttgtggg tcacagtct                                                    19

<210> SEQ ID NO 271
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 271
aatttgtggg tcacagttt                                                    19

<210> SEQ ID NO 272
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 272
caattgtggg tcacagtat                                                    19

<210> SEQ ID NO 273
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 273
caattgtggg tcacagtct                                                    19

<210> SEQ ID NO 274
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 274
caattgtggg tcacagttt                                                    19

<210> SEQ ID NO 275
<211> LENGTH: 19

-continued

```
<212> TYPE: DNA
<213> ORGANISM: Artificial Sequence
<220> FEATURE:
<223> OTHER INFORMATION: Human immunodeficiency virus envelope F3 primer

<400> SEQUENCE: 275
cacttgtggg tcacagtat                                                 19

<210> SEQ ID NO 276
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 276
cacttgtggg tcacagtct                                                 19

<210> SEQ ID NO 277
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 277
cacttgtggg tcacagttt                                                 19

<210> SEQ ID NO 278
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 278
catttgtggg tcacagtat                                                 19

<210> SEQ ID NO 279
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 279
catttgtggg tcacagtct                                                 19

<210> SEQ ID NO 280
<211> LENGTH: 19
<212> TYPE: DNA
<213> ORGANISM: Artificial Sequence
<220> FEATURE:
<223> OTHER INFORMATION: Human immunodeficiency virus envelope F3 primer

<400> SEQUENCE: 280
catttgtggg tcacagttt                                                 19

<210> SEQ ID NO 281
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 281
```
ccacatgtta aaatcttctg tcac 24

<210> SEQ ID NO 282
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 282
ccacatgtta aaatcttctg tgac 24

<210> SEQ ID NO 283
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 283
ccacatgtta aaatcttctg ttac 24

<210> SEQ ID NO 284
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 284
ccacatgtta aaattttctg tcac 24

<210> SEQ ID NO 285
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 285
ccacatgtta aaattttctg tgac 24

<210> SEQ ID NO 286
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 286
ccacatgtta aaattttctg ttac 24

<210> SEQ ID NO 287
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 287
ccacatgtta aactcttctg tcac 24

<210> SEQ ID NO 288
<211> LENGTH: 24
<212> TYPE: DNA
<213> ORGANISM: Artificial Sequence

```
<220> FEATURE:
<223> OTHER INFORMATION: Human immunodeficiency virus envelope B3 primer

<400> SEQUENCE: 288
ccacatgtta aactcttctg tgac                                              24

<210> SEQ ID NO 289
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 289
ccacatgtta aactcttctg ttac                                              24

<210> SEQ ID NO 290
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 290
ccacatgtta aactttctg tcac                                               24

<210> SEQ ID NO 291
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 291
ccacatgtta aactttctg tgac                                               24

<210> SEQ ID NO 292
<211> LENGTH: 24
<212> TYPE: DNA
<213> ORGANISM: Artificial Sequence
<220> FEATURE:
<223> OTHER INFORMATION: Human immunodeficiency virus envelope B3 primer

<400> SEQUENCE: 292
ccacatgtta aactttctg ttac                                               24

<210> SEQ ID NO 293
<211> LENGTH: 42
<212> TYPE: DNA
<213> ORGANISM: Artificial Sequence
<220> FEATURE:
<223> OTHER INFORMATION: Human immunodeficiency virus envelope FIP
      primer
<220> FEATURE:
<221> NAME/KEY: misc_feature
<222> LOCATION: (25)..(25)
<223> OTHER INFORMATION: A linker is present between nucleotides 24 and
      25.

<400> SEQUENCE: 293
tcatatgctt tagcatctga tgcagggtac ctgtgtggaa ag                          42

<210> SEQ ID NO 294
<211> LENGTH: 42
<212> TYPE: DNA
<213> ORGANISM: Artificial Sequence
<220> FEATURE:
```

<223> OTHER INFORMATION: Human immunodeficiency virus envelope FIP
      primer
<220> FEATURE:
<221> NAME/KEY: misc_feature
<222> LOCATION: (25)..(25)
<223> OTHER INFORMATION: A linker is present between nucleotides 24 and
      25.

<400> SEQUENCE: 294
tcatatgctt tagcatctga tgcagggtac ctgtgtggag ag                              42

<210> SEQ ID NO 295
<211> LENGTH: 42
<212> TYPE: DNA
<213> ORGANISM: Artificial Sequence
<220> FEATURE:
<223> OTHER INFORMATION: Human immunodeficiency virus envelope FIP
      primer
<220> FEATURE:
<221> NAME/KEY: misc_feature
<222> LOCATION: (25)..(25)
<223> OTHER INFORMATION: A linker is present between nucleotides 24 and
      25.

<400> SEQUENCE: 295
ttatatgctt tagcatctga tgcagggtac ctgtgtggaa ag                              42

<210> SEQ ID NO 296
<211> LENGTH: 42
<212> TYPE: DNA
<213> ORGANISM: Artificial Sequence
<220> FEATURE:
<223> OTHER INFORMATION: Human immunodeficiency virus envelope FIP
      primer
<220> FEATURE:
<221> NAME/KEY: misc_feature
<222> LOCATION: (25)..(25)
<223> OTHER INFORMATION: A linker is present between nucleotides 24 and
      25.

<400> SEQUENCE: 296
ttatatgctt tagcatctga tgcagggtac ctgtgtggag ag                              42

<210> SEQ ID NO 297
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 297
cagaagtaca taatgtctgg gccactactt cttgtgggtt gg                              42

<210> SEQ ID NO 298
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

-continued

<400> SEQUENCE: 298
cagaagtaca taatgtctgg gccactattt cttgtgggtt gg                            42

<210> SEQ ID NO 299
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 299
cagaagtaca taatgtctgg gcctctactt cttgtgggtt gg                            42

<210> SEQ ID NO 300
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 300
cagaagtaca taatgtctgg gcctctattt cttgtgggtt gg                            42

<210> SEQ ID NO 301
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 301
cagaagtaca taatgtctgg gctactactt cttgtgggtt gg                            42

<210> SEQ ID NO 302
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 302
cagaagtaca taatgtctgg gctactattt cttgtgggtt gg                            42

<210> SEQ ID NO 303

```
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 303
cagaagtaca taatgtctgg gcttctactt cttgtgggtt gg                           42

<210> SEQ ID NO 304
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 304
cagaagtaca taatgtctgg gcttctattt cttgtgggtt gg                           42

<210> SEQ ID NO 305
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 305
cagaagtaca taatgtttgg gccactactt cttgtgggtt gg                           42

<210> SEQ ID NO 306
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 306
cagaagtaca taatgtttgg gccactattt cttgtgggtt gg                           42

<210> SEQ ID NO 307
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
```

-continued

<221> NAME/KEY: misc_feature
<222> LOCATION: (24)..(24)
<223> OTHER INFORMATION: A linker is present between nucleotides 23 and
      24.

<400> SEQUENCE: 307
cagaagtaca taatgtttgg gcctctactt cttgtgggtt gg        42

<210> SEQ ID NO 308
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 308
cagaagtaca taatgtttgg gcctctattt cttgtgggtt gg        42

<210> SEQ ID NO 309
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 309
cagaagtaca taatgtttgg gctactactt cttgtgggtt gg        42

<210> SEQ ID NO 310
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 310
cagaagtaca taatgtttgg gctactattt cttgtgggtt gg        42

<210> SEQ ID NO 311
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 311
cagaagtaca taatgtttgg gcttctactt cttgtgggtt gg                              42

<210> SEQ ID NO 312
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 312
cagaagtaca taatgtttgg gcttctattt cttgtgggtt gg                              42

<210> SEQ ID NO 313
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 313
cagaagtgca taatgtctgg gccactactt cttgtgggtt gg                              42

<210> SEQ ID NO 314
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 314
cagaagtgca taatgtctgg gccactattt cttgtgggtt gg                              42

<210> SEQ ID NO 315
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 315
cagaagtgca taatgtctgg gcctctactt cttgtgggtt gg                              42

<210> SEQ ID NO 316
<211> LENGTH: 42
<212> TYPE: DNA
<213> ORGANISM: Artificial Sequence

```
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 316
cagaagtgca taatgtctgg gcctctattt cttgtgggtt gg                            42

<210> SEQ ID NO 317
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 317
cagaagtgca taatgtctgg gctactactt cttgtgggtt gg                            42

<210> SEQ ID NO 318
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 318
cagaagtgca taatgtctgg gctactatttt cttgtgggtt gg                           42

<210> SEQ ID NO 319
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 319
cagaagtgca taatgtctgg gcttctactt cttgtgggtt gg                            42

<210> SEQ ID NO 320
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
```

24.

<400> SEQUENCE: 320
cagaagtgca taatgtctgg gcttctattt cttgtgggtt gg        42

<210> SEQ ID NO 321
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 321
cagaagtgca taatgtttgg gccactactt cttgtgggtt gg        42

<210> SEQ ID NO 322
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 322
cagaagtgca taatgtttgg gccactatttt cttgtgggtt gg        42

<210> SEQ ID NO 323
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 323
cagaagtgca taatgtttgg gcctctactt cttgtgggtt gg        42

<210> SEQ ID NO 324
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24..

<400> SEQUENCE: 324
cagaagtgca taatgtttgg gcctctattt cttgtgggtt gg        42

```
<210> SEQ ID NO 325
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 325
cagaagtgca taatgtttgg gctactactt cttgtgggtt gg                           42

<210> SEQ ID NO 326
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 326
cagaagtgca taatgtttgg gctactattt cttgtgggtt gg                           42

<210> SEQ ID NO 327
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 327
cagaagtgca taatgtttgg gcttctactt cttgtgggtt gg                           42

<210> SEQ ID NO 328
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 328
cagaagtgca taatgtttgg gcttctattt cttgtgggtt gg                           42

<210> SEQ ID NO 329
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
```

```
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 329
cagaggtaca taatgtctgg gccactactt cttgtgggtt gg                        42

<210> SEQ ID NO 330
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 330
cagaggtaca taatgtctgg gccactattt cttgtgggtt gg                        42

<210> SEQ ID NO 331
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 331
cagaggtaca taatgtctgg gcctctactt cttgtgggtt gg                        42

<210> SEQ ID NO 332
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 332
cagaggtaca taatgtctgg gcctctattt cttgtgggtt gg                        42

<210> SEQ ID NO 333
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 333
```
cagaggtaca taatgtctgg gctactactt cttgtgggtt gg                         42

<210> SEQ ID NO 334
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 334
cagaggtaca taatgtctgg gctactattt cttgtgggtt gg                         42

<210> SEQ ID NO 335
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 335
cagaggtaca taatgtctgg gcttctactt cttgtgggtt gg                         42

<210> SEQ ID NO 336
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 336
cagaggtaca taatgtctgg gcttctattt cttgtgggtt gg                         42

<210> SEQ ID NO 337
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 337
cagaggtaca taatgtttgg gccactactt cttgtgggtt gg                         42

<210> SEQ ID NO 338
<211> LENGTH: 42
<212> TYPE: DNA

```
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 338
cagaggtaca taatgtttgg gccactattt cttgtgggtt gg                          42

<210> SEQ ID NO 339
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 339
cagaggtaca taatgtttgg gcctctactt cttgtgggtt gg                          42

<210> SEQ ID NO 340
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 340
cagaggtaca taatgtttgg gcctctattt cttgtgggtt gg                          42

<210> SEQ ID NO 341
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 341
cagaggtaca taatgtttgg gctactactt cttgtgggtt gg                          42

<210> SEQ ID NO 342
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
```

```
<223> OTHER INFORMATION: A linker is present between nucleotides 23 and
      24.

<400> SEQUENCE: 342
cagaggtaca taatgtttgg gctactattt cttgtgggtt gg                             42

<210> SEQ ID NO 343
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 343
cagaggtaca taatgtttgg gcttctactt cttgtgggtt gg                             42

<210> SEQ ID NO 344
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 344
cagaggtaca taatgtttgg gcttctattt cttgtgggtt gg                             42

<210> SEQ ID NO 345
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 345
cagaggtgca taatgtctgg gccactactt cttgtgggtt gg                             42

<210> SEQ ID NO 346
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 346
cagaggtgca taatgtctgg gccactattt cttgtgggtt gg                             42
```

```
<210> SEQ ID NO 347
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 347
cagaggtgca taatgtctgg gcctctactt cttgtgggtt gg                              42

<210> SEQ ID NO 348
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 348
cagaggtgca taatgtctgg gcctctattt cttgtgggtt gg                              42

<210> SEQ ID NO 349
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 349
cagaggtgca taatgtctgg gctactactt cttgtgggtt gg                              42

<210> SEQ ID NO 350
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 350
cagaggtgca taatgtctgg gctactattt cttgtgggtt gg                              42

<210> SEQ ID NO 351
<211> LENGTH: 42
<212> TYPE: DNA
<213> ORGANISM: Artificial Sequence
<220> FEATURE:
<223> OTHER INFORMATION: Human immunodeficiency virus envelope BIP
```

-continued primer
<220> FEATURE:
<221> NAME/KEY: misc_feature
<222> LOCATION: (24)..(24)
<223> OTHER INFORMATION: A linker is present between nucleotides 23 and
    24.

<400> SEQUENCE: 351
cagaggtgca taatgtctgg gcttctactt cttgtgggtt gg                                 42

<210> SEQ ID NO 352
<211> LENGTH: 42
<212> TYPE: DNA
<213> ORGANISM: Artificial Sequence
<220> FEATURE:
<223> OTHER INFORMATION: Human immunodeficiency virus envelope BIP
    primer
<220> FEATURE:
<221> NAME/KEY: misc_feature
<222> LOCATION: (24)..(24)
<223> OTHER INFORMATION: A linker is present between nucleotides 23 and
    24.

<400> SEQUENCE: 352
cagaggtgca taatgtctgg gcttctattt cttgtgggtt gg                                 42

<210> SEQ ID NO 353
<211> LENGTH: 42
<212> TYPE: DNA
<213> ORGANISM: Artificial Sequence
<220> FEATURE:
<223> OTHER INFORMATION: Human immunodeficiency virus envelope BIP
    primer
<220> FEATURE:
<221> NAME/KEY: misc_feature
<222> LOCATION: (24)..(24)
<223> OTHER INFORMATION: A linker is present between nucleotides 23 and
    24.

<400> SEQUENCE: 353
cagaggtgca taatgtttgg gccactactt cttgtgggtt gg                                 42

<210> SEQ ID NO 354
<211> LENGTH: 42
<212> TYPE: DNA
<213> ORGANISM: Artificial Sequence
<220> FEATURE:
<223> OTHER INFORMATION: Human immunodeficiency virus envelope BIP
    primer
<220> FEATURE:
<221> NAME/KEY: misc_feature
<222> LOCATION: (24)..(24)
<223> OTHER INFORMATION: A linker is present between nucleotides 23 and
    24.

<400> SEQUENCE: 354
cagaggtgca taatgtttgg gccactattt cttgtgggtt gg                                 42

<210> SEQ ID NO 355
<211> LENGTH: 42
<212> TYPE: DNA
<213> ORGANISM: Artificial Sequence
<220> FEATURE:
<223> OTHER INFORMATION: Human immunodeficiency virus envelope BIP
    primer
<220> FEATURE:
<221> NAME/KEY: misc_feature
<222> LOCATION: (24)..(24)
<223> OTHER INFORMATION: A linker is present between nucleotides 23 and
    24.

```
<400> SEQUENCE: 355
cagaggtgca taatgtttgg gcctctactt cttgtgggtt gg                              42

<210> SEQ ID NO 356
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 356
cagaggtgca taatgtttgg gcctctattt cttgtgggtt gg                              42

<210> SEQ ID NO 357
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 357
cagaggtgca taatgtttgg gctactactt cttgtgggtt gg                              42

<210> SEQ ID NO 358
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 358
cagaggtgca taatgtttgg gctactattt cttgtgggtt gg                              42

<210> SEQ ID NO 359
<211> LENGTH: 42
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 359
cagaggtgca taatgtttgg gcttctactt cttgtgggtt gg                              42

<210> SEQ ID NO 360
<211> LENGTH: 42
```

```
<212> TYPE: DNA
<213> ORGANISM: Artificial Sequence
<220> FEATURE:
<223> OTHER INFORMATION: Human immunodeficiency virus envelope BIP
      primer
<220> FEATURE:
<221> NAME/KEY: misc_feature
<222> LOCATION: (24)..(24)
<223> OTHER INFORMATION: A linker is present between nucleotides 23 and
      24.

<400> SEQUENCE: 360
cagaggtgca taatgtttgg gcttctattt cttgtgggtt gg                         42

<210> SEQ ID NO 361
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 361
caaaatagag tggtagttgc a                                                21

<210> SEQ ID NO 362
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 362
caaaatagag tggtagttgc g                                                21

<210> SEQ ID NO 363
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 363
caaaatagag tggtagttgc t                                                21

<210> SEQ ID NO 364
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 364
caaaatagag tggtatttgc a                                                21

<210> SEQ ID NO 365
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 365
caaaatagag tggtatttgc g                                                21
```

<210> SEQ ID NO 366
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 366
caaaatagag tggtatttgc t                                              21

<210> SEQ ID NO 367
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 367
caaaatagag tggttgttgc a                                              21

<210> SEQ ID NO 368
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 368
caaaatagag tggttgttgc g                                              21

<210> SEQ ID NO 369
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 369
caaaatagag tggttgttgc t                                              21

<210> SEQ ID NO 370
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 370
caaaatagag tggtttttgc a                                              21

<210> SEQ ID NO 371
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 371
caaaatagag tggtttttgc g                                              21

<210> SEQ ID NO 372
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 372
caaaatagag tggtttttgc t 21

<210> SEQ ID NO 373
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 373
caaaatagag tggtggttgc a 21

<210> SEQ ID NO 374
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 374
caaaatagag tggtggttgc g 21

<210> SEQ ID NO 375
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 375
caaaatagag tggtggttgc t 21

<210> SEQ ID NO 376
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 376
caaaatagag tggtgtttgc a 21

<210> SEQ ID NO 377
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 377
caaaatagag tggtgtttgc g 21

```
<210> SEQ ID NO 378
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 378
caaaatagag tggtgtttgc t                                              21

<210> SEQ ID NO 379
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 379
caaaatagag tggtcgttgc a                                              21

<210> SEQ ID NO 380
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 380
caaaatagag tggtcgttgc g                                              21

<210> SEQ ID NO 381
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 381
caaaatagag tggtcgttgc t                                              21

<210> SEQ ID NO 382
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 382
caaaatagag tggtctttgc a                                              21

<210> SEQ ID NO 383
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 383
caaaatagag tggtctttgc g                                              21

<210> SEQ ID NO 384
```

```
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 384
caaaatagag tggtctttgc t                                              21

<210> SEQ ID NO 385
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 385
caaaataggg tggtagttgc a                                              21

<210> SEQ ID NO 386
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 386
caaaataggg tggtagttgc g                                              21

<210> SEQ ID NO 387
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 387
caaaataggg tggtagttgc t                                              21

<210> SEQ ID NO 388
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 388
caaaataggg tggtatttgc a                                              21

<210> SEQ ID NO 389
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 389
caaaataggg tggtatttgc g                                              21

<210> SEQ ID NO 390
<211> LENGTH: 21
```

```
<212> TYPE: DNA
<213> ORGANISM: Artificial Sequence
<220> FEATURE:
<223> OTHER INFORMATION: Human immunodeficiency virus envelope loop F primer
<400> SEQUENCE: 390
caaaataggg tggtatttgc t 21

<210> SEQ ID NO 391
<211> LENGTH: 21
<212> TYPE: DNA
<213> ORGANISM: Artificial Sequence
<220> FEATURE:
<223> OTHER INFORMATION: Human immunodeficiency virus envelope loop F primer
<400> SEQUENCE: 391
caaaataggg tggttgttgc a 21

<210> SEQ ID NO 392
<211> LENGTH: 21
<212> TYPE: DNA
<213> ORGANISM: Artificial Sequence
<220> FEATURE:
<223> OTHER INFORMATION: Human immunodeficiency virus envelope loop F primer
<400> SEQUENCE: 392
caaaataggg tggttgttgc g 21

<210> SEQ ID NO 393
<211> LENGTH: 21
<212> TYPE: DNA
<213> ORGANISM: Artificial Sequence
<220> FEATURE:
<223> OTHER INFORMATION: Human immunodeficiency virus envelope loop F primer
<400> SEQUENCE: 393
caaaataggg tggttgttgc t 21

<210> SEQ ID NO 394
<211> LENGTH: 21
<212> TYPE: DNA
<213> ORGANISM: Artificial Sequence
<220> FEATURE:
<223> OTHER INFORMATION: Human immunodeficiency virus envelope loop F primer
<400> SEQUENCE: 394
caaaataggg tggtttttgc a 21

<210> SEQ ID NO 395
<211> LENGTH: 21
<212> TYPE: DNA
<213> ORGANISM: Artificial Sequence
<220> FEATURE:
<223> OTHER INFORMATION: Human immunodeficiency virus envelope loop F primer
<400> SEQUENCE: 395
caaaataggg tggtttttgc g 21

<210> SEQ ID NO 396
<211> LENGTH: 21
<212> TYPE: DNA

```
<213> ORGANISM: Artificial Sequence
<220> FEATURE:
<223> OTHER INFORMATION: Human immunodeficiency virus envelope loop F
      primer

<400> SEQUENCE: 396
caaaataggg tggtttttgc t                                              21

<210> SEQ ID NO 397
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 397
caaaataggg tggtggttgc a                                              21

<210> SEQ ID NO 398
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 398
caaaataggg tggtggttgc g                                              21

<210> SEQ ID NO 399
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 399
caaaataggg tggtggttgc t                                              21

<210> SEQ ID NO 400
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 400
caaaataggg tggtgtttgc a                                              21

<210> SEQ ID NO 401
<211> LENGTH: 21
<212> TYPE: DNA
<213> ORGANISM: Artificial Sequence
<220> FEATURE:
<223> OTHER INFORMATION: Human immunodeficiency virus envelope loop F
      primer

<400> SEQUENCE: 401
caaaataggg tggtgtttgc g                                              21

<210> SEQ ID NO 402
<211> LENGTH: 21
<212> TYPE: DNA
<213> ORGANISM: Artificial Sequence
```

<220> FEATURE:
<223> OTHER INFORMATION: Human immunodeficiency virus envelope loop F
      primer

<400> SEQUENCE: 402
caaaataggg tggtgtttgc t 21

<210> SEQ ID NO 403
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 403
caaaataggg tggtcgttgc a 21

<210> SEQ ID NO 404
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 404
caaaataggg tggtcgttgc g 21

<210> SEQ ID NO 405
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 405
caaaataggg tggtcgttgc t 21

<210> SEQ ID NO 406
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 406
caaaataggg tggtctttgc a 21

<210> SEQ ID NO 407
<211> LENGTH: 21
<212> TYPE: DNA
<213> ORGANISM: Artificial Sequence
<220> FEATURE:
<223> OTHER INFORMATION: Human immunodeficiency virus envelope loop F primer

<400> SEQUENCE: 407
caaaataggg tggtctttgc g 21

<210> SEQ ID NO 408
<211> LENGTH: 21
<212> TYPE: DNA
<213> ORGANISM: Artificial Sequence
<220> FEATURE:

<223> OTHER INFORMATION: Human immunodeficiency virus envelope loop F
     primer

<400> SEQUENCE: 408
caaaataggg tggtctttgc t                                             21

<210> SEQ ID NO 409
<211> LENGTH: 18
<212> TYPE: DNA
<213> ORGANISM: Artificial Sequence
<220> FEATURE:
<223> OTHER INFORMATION: Human immunodeficiency virus envelope loop B
     primer

<400> SEQUENCE: 409
acacacgcct gtgtacca                                                 18

<210> SEQ ID NO 410
<211> LENGTH: 18
<212> TYPE: DNA
<213> ORGANISM: Artificial Sequence
<220> FEATURE:
<223> OTHER INFORMATION: Human immunodeficiency virus envelope loop B
     primer

<400> SEQUENCE: 410
acacacgcct gtgtaccc                                                 18

<210> SEQ ID NO 411
<211> LENGTH: 18
<212> TYPE: DNA
<213> ORGANISM: Artificial Sequence
<220> FEATURE:
<223> OTHER INFORMATION: Human immunodeficiency virus envelope loop B
     primer

<400> SEQUENCE: 411
acacatgcct gtgtacca                                                 18

<210> SEQ ID NO 412
<211> LENGTH: 18
<212> TYPE: DNA
<213> ORGANISM: Artificial Sequence
<220> FEATURE:
<223> OTHER INFORMATION: Human immunodeficiency virus envelope loop B
     primer

<400> SEQUENCE: 412
acacatgcct gtgtaccc                                                 18

<210> SEQ ID NO 413
<211> LENGTH: 9181
<212> TYPE: DNA
<213> ORGANISM: Human immunodeficiency virus

<400> SEQUENCE: 413
ggtctctctg gttagaccag atctgagcct gggagctctc tggctaacta gggaacccac    60
tgcttaagcc tcaataaagc ttgccttgag tgcttcaagt agtgtgtgcc cgtctgttgt   120
gtgactctgg taactagaga tccctcagac ccttttagtc agtgtggaaa atctctagca   180
gtggcgcccg aacagggacc tgaaagcgaa agggaaacca gaggagctct ctcgacgcag   240
gactcggctt gctgaagcgc gcacggcaag aggcgagggg cggcgactgg tgagtacgcc   300
aaaaattttg actagcggag gctagaagga gagagatggg tgcgagagcg tcagtattaa   360

```
gcgggggaga attagatcga tgggaaaaaa ttcggttaag gccagggggga aagaaaaaat    420 ataaattaaa acatatagta tgggcaagca gggagctaga acgattcgca gttaatcctg    480
gcctgttaga acatcagaa ggctgtagac aaatactggg acagctacaa ccatcccttc     540
agacaggatc agaagaactt agatcattat ataatacagt agcaaccctc tattgtgtgc    600
atcaaaggat agagataaaa gacaccaagg aagctttaga caagatagag gaagagcaaa   660
acaaaagtaa gaaaaaagca cagcaagcag cagctgacac aggacacagc aatcaggtca    720
gccaaaatta ccctatagtg cagaacatcc aggggcaaat ggtacatcag gccatatcac    780
ctagaacttt aaatgcatgg gtaaaagtag tagaagagaa ggctttcagc ccagaagtga    840
tacccatgtt ttcagcatta tcagaaggag ccaccccaca agatttaaac accatgctaa    900
acacagtggg gggacatcaa gcagccatgc aaatgttaaa agagaccatc aatgaggaag    960
ctgcagaatg ggatagagtg catccagtgc atgcagggcc tattgcacca ggccagatga   1020
gagaaccaag gggaagtgac atagcaggaa ctactagtac ccttcaggaa caaataggat   1080
ggatgacaaa taatccacct atcccagtag gagaaattta taaaagatgg ataatcctgg   1140
gattaaataa aatagtaaga atgtatagcc ctaccagcat tctggacata agacaaggac   1200
caaaggaacc ctttagagac tatgtagacc ggttctataa aactctaaga gccgagcaag   1260
cttcacagga ggtaaaaaat tggatgacag aaaccttgtt ggtccaaaat gcgaacccag   1320
attgtaagac tattttaaaa gcattgggac cagcggctac actagaagaa atgatgacag   1380
catgtcaggg agtaggagga cccggccata aggcaagagt tttggctgaa gcaatgagcc   1440
aagtaacaaa ttcagctacc ataatgatgc agagaggcaa ttttaggaac caagaaaaga   1500
ttgttaagtg tttcaattgt ggcaaagaag ggcacacagc cagaaattgc agggccccta   1560
ggaaaaaggg ctgttggaaa tgtggaaagg aaggacacca aatgaaagat tgtactgaga   1620
gacaggctaa ttttttaggg aagatctggc cttcctacaa gggaaggcca gggaattttc   1680
ttcagagcag accagagcca acagccccac cagaagagag cttcaggtct ggggtagaga   1740
caacaactcc ccctcagaag caggagccga tagacaagga actgtatcct ttaacttccc   1800
tcaggtcact ctttggcaac gaccctcgt cacaataaag ataggggggc aactaaagga    1860
agctctatta gatacaggag cagatgatac agtattagaa gaaatgagtt tgccaggaag   1920
atggaaacca aaaatgatag ggggaattgg aggttttatc aaagtaagac agtatgatca   1980
gatactcata gaaatctgtg gacataaagc tataggtaca gtattagtag gacctacacc   2040
tgtcaacata attggaagaa atctgttgac tcagattggt tgcactttaa attttcccat   2100
tagccctatt gagactgtac cagtaaaatt aaagccagga atggatggcc caaaagttaa   2160
acaatggcca ttgacagaag aaaaaataaa agcattagta gaaatttgta cagagatgga   2220
aaaggaaggg aaaatttcaa aaattgggcc tgaaaatcca tacaatactc cagtatttgc   2280
cataaagaaa aaagacagta ctaaatggag aaaattagta gatttcagag aacttaataa   2340
gagaactcaa gacttctggg aagttcaatt aggaatacca catcccgcag ggttaaaaaa   2400
gaaaaaatca gtaacagtac tggatgtggg tgatgcatat ttttcagttc ccttagatga   2460
agacttcagg aagtatactg catttaccat acctagtata aacaatgaga caccagggat   2520
tagatatcag tacaatgtgc ttccacaggg atggaaagga tcaccagcaa tattccaaag   2580
tagcatgaca aaaatcttag agccttttag aaaacaaaat ccagacatag ttatctatca   2640
atacatggat gatttgtatg taggatctga cttagaaata gggcagcata gaacaaaaat   2700
agaggagctg agacaacatc tgttgaggtg gggacttacc acaccagaca aaaacatca    2760
```

```
gaaagaacct ccattccttt ggatgggtta tgaactccat cctgataaat ggacagtaca      2820
gcctatagtg ctgccagaaa aagacagctg gactgtcaat gacatacaga agttagtggg      2880
gaaattgaat tgggcaagtc agatttaccc agggattaaa gtaaggcaat tatgtaaact      2940
ccttagagga accaaagcac taacagaagt aataccacta acagaagaag cagagctaga      3000
actggcagaa aacagagaga ttctaaaaga accagtacat ggagtgtatt atgacccatc      3060
aaaagactta atagcagaaa tacagaagca ggggcaaggc caatggacat atcaaattta      3120
tcaagagcca tttaaaaatc tgaaaacagg aaaatatgca agaatgaggg gtgcccacac      3180
taatgatgta aaacaattaa cagaggcagt gcaaaaaata accacagaaa gcatagtaat      3240
atggggaaag actcctaaat ttaaactgcc catacaaaag gaaacatggg aaacatggtg      3300
gacagagtat tggcaagcca cctggattcc tgagtgggag tttgttaata cccctccctt      3360
agtgaaatta tggtaccagt tagagaaaga acccatagta ggagcagaaa ccttctatgt      3420
agatggggca gctaacaggg agactaaatt aggaaaagca ggatatgtta ctaatagagg      3480
aagacaaaaa gttgtcaccc taactgacac aacaaatcag aagactgagt tacaagcaat      3540
ttatctagct ttgcaggatt cgggattaga agtaaacata gtaacagact cacaatatgc      3600
attaggaatc attcaagcac aaccagatca aagtgaatca gagttagtca atcaaataat      3660
agagcagtta ataaaaaagg aaaaggtcta tctggcatgg gtaccagcac acaaaggaat      3720
tggaggaaat gaacaagtag ataaattagt cagtgctgga atcaggaaag tactatttt      3780 agatggaata gataaggccc aagatgaaca tgagaaatat cacagtaatt ggagagcaat      3840
ggctagtgat tttaacctgc cacctgtagt agcaaaagaa atagtagcca gctgtgataa      3900
atgtcagcta aaaggagaag ccatgcatgg acaagtagac tgtagtccag gaatatggca      3960
actagattgt acacatttag aaggaaaagt tatcctggta gcagttcatg tagccagtgg      4020
atatatagaa gcagaagtta ttccagcaga acagggcag gaaacagcat attttctttt      4080
aaaattagca ggaagatggc cagtaaaaac aatacatact gacaatggca gcaatttcac      4140
cggtgctacg gttagggccg cctgttggtg ggcgggaatc aagcaggaat ttggaattcc      4200
ctacaatccc caaagtcaag gagtagtaga atctatgaat aaagaattaa agaaaattat      4260
aggacaggta agagatcagg ctgaacatct taagacagca gtacaaatgg cagtattcat      4320
ccacaatttt aaaagaaaag gggggattgg ggggtacagt gcaggggaaa gaatagtaga      4380
cataatagca acagacatac aaactaaaga attacaaaaa caaattacaa aaattcaaaa      4440
ttttcgggtt tattacaggg acagcagaaa tccactttgg aaaggaccag caaagctcct      4500
ctggaaaggt gaaggggcag tagtaataca agataatagt gacataaaag tagtgccaag      4560
aagaaaagca aagatcatta gggattatgg aaaacagatg gcaggtgatg attgtgtggc      4620
aagtagacag gatgaggatt agaacatgga aagtttagt aaaacaccat atgtatgttt      4680
cagggaaagc tagggatgg ttttatagac atcactatga aagccctcat ccaagaataa      4740
gttcagaagt acacatccca ctaggggatg ctagattggt aataacaaca tattggggtc      4800
tgcatacagg agaaagagac tggcatttgg gtcagggagt ctccatagaa tggaggaaaa      4860
agagatatag cacacaagta gaccctgaac tagcagacca actaattcat ctgtattact      4920
ttgactgttt ttcagactct gctataagaa aggccttatt aggacacata gttagcccta      4980
ggtgtgaata tcaagcagga cataacaagg taggatctct acaatacttg gcactagcag      5040
cattaataac accaaaaaag ataaagccac ctttgcctag tgttacgaaa ctgacagagg      5100
```

```
atagatggaa caagccccag aagaccaagg gccacagagg gagccacaca atgaatggac    5160
actagagctt ttagaggagc ttaagaatga agctgttaga cattttccta ggatttggct    5220
ccatggctta gggcaacata tctatgaaac ttatggggat acttgggcag gagtggaagc    5280
cataataaga attctgcaac aactgctgtt tatccatttt cagaattggg tgtcgacata    5340
gcagaatagg cgttactcga cagaggagag caagaaatgg agccagtaga tcctagacta    5400
gagccctgga agcatccagg aagtcagcct aaaactgctt gtaccaattg ctattgtaaa    5460
aagtgttgct ttcattgcca agtttgtttc ataacaaaag ccttaggcat ctcctatggc    5520
aggaagaagc ggagacagcg acgaagagct catcagaaca gtcagactca tcaagcttct    5580
ctatcaaagc agtaagtagt acatgtaatg caacctatac aatagtagc aatagtagca    5640 ttagtagtag caataataat agcaatagtt gtgtggtcca tagtaatcat agaatatagg    5700
aaaatattaa gacaaagaaa aatagacagg ttaattgata gactaataga aagagcagaa    5760
gacagtggca atgagagtga aggagaaata tcagcacttg tggagatggg ggtggagatg    5820
gggcaccatg ctccttggga tgttgatgat ctgtagtgct acagaaaaat tgtgggtcac    5880
agtctattat ggggtacctg tgtggaagga agcaaccacc actctatttt gtgcatcaga    5940
tgctaaagca tatgatacag aggtacataa tgtttgggcc acacatgcct gtgtacccac    6000 agacccccaac ccacaagaag tagtattggt aaatgtgaca gaaaatttta acatgtggaa    6060
aaatgacatg gtagaacaga tgcatgagga tataatcagt ttatgggatc aaagcctaaa    6120
gccatgtgta aaattaaccc cactctgtgt tagtttaaag tgcactgatt tgaagaatga    6180
tactaatacc aatagtagta gcgggagaat gataatggag aaaggagaga taaaaaactg    6240
ctctttcaat atcagcacaa gcataagagg taaggtgcag aaagaatatg catttttta    6300 taaacttgat ataataccaa tagataatga tactaccagc tataagttga caagttgtaa    6360
cacctcagtc attacacagg cctgtccaaa ggtatccttt gagccaattc ccatacatta    6420
ttgtgccccg gctggttttg cgattctaaa atgtaataat aagacgttca atggaacagg    6480
accatgtaca aatgtcagca cagtacaatg tacacatgga attaggccag tagtatcaac    6540
tcaactgctg ttaaatggca gtctagcaga agaagaggta gtaattagat ctgtcaattt    6600
cacggacaat gctaaaacca taatagtaca gctgaacaca tctgtagaaa ttaattgtac    6660
aagacccaac aacaatacaa gaaaaagaat ccgtatccag agaggaccag ggagagcatt    6720
tgttacaata ggaaaaatag gaaatatgag acaagcacat tgtaacatta gtagagcaaa    6780
atggaataac actttaaaac agatagctag caaattaaga gaacaatttg gaaataataa    6840
aacaataatc tttaagcaat cctcaggagg ggacccagaa attgtaacgc acagttttaa    6900
ttgtggaggg gaatttttct actgtaattc aacacaactg tttaatagta cttggtttaa    6960
tagtacttgg agtactgaag ggtcaaataa cactgaagga agtgacacaa tcaccctccc    7020
atgcagaata aaacaaatta taaacatgtg gcagaaagta ggaaaagcaa tgtatgcccc    7080
tcccatcagt ggacaaatta gatgttcatc aaatattaca gggctgctat taacaagaga    7140
tggtggtaat agcaacaatg agtccgagat cttcagacct ggaggaggag atatgaggga    7200
caattggaga agtgaattat ataaatataa agtagtaaaa attgaaccat taggagtagc    7260
acccaccaag gcaaagagaa gagtggtgca gagagaaaaa agagcagtgg aataggagc    7320 tttgttcctt gggttcttgg gagcagcagg aagcactatg ggcgcagcct caatgacgct    7380
gacggtacag gccagacaat tattgtctgg tatagtgcag cagcagaaca atttgctgag    7440
ggctattgag gcgcaacagc atctgttgca actcacagtc tggggcatca agcagctcca    7500
```

```
ggcaagaatc ctggctgtgg aaagatacct aaaggatcaa cagctcctgg ggatttgggg    7560
ttgctctgga aaactcattt gcaccactgc tgtgccttgg aatgctagtt ggagtaataa    7620
atctctggaa cagatttgga atcacacgac ctggatggag tgggacagag aaattaacaa    7680
ttacacaagc ttaatacact ccttaattga gaatcgcaa aaccagcaag aaagaatga     7740 acaagaatta ttggaattag ataaatgggc aagtttgtgg aattggttta cataacaaa    7800 ttggctgtgg tatataaaat tattcataat gatagtagga ggcttggtag gtttaagaat    7860 agttttgct gtactttcta tagtgaatag agttaggcag ggatattcac cattatcgtt     7920
tcagacccac ctcccaaccc cgaggggacc cgacaggccc gaaggaatag aagaagaagg    7980
tggagagaga gacagagaca gatccattcg attagtgaac ggatccttgg cacttatctg    8040
ggacgatctg cggagcctgt gcctcttcag ctaccaccgc ttgagagact tactcttgat    8100
tgtaacgagg attgtggaac ttctgggacg caggggtgg gaagccctca aatattggtg    8160
gaatctccta cagtattgga gtcaggaact aagaatagt gctgttagct tgctcaatgc    8220
cacagccata gcagtagctg aggggacaga taggttata gaagtagtac aaggagcttg    8280
tagagctatt cgccacatac ctagaagaat aagacagggc ttggaaagga ttttgctata    8340
agatgggtgg caagtggtca aaaagtagtg tgattggatg cctactgta agggaaagaa    8400 tgagacgagc tgagccagca gcagatagg tgggagcagc atctcgagac ctggaaaaac     8460
atggagcaat cacaagtagc aatacagcag ctaccaatgc tgcttgtgcc tggctagaag    8520
cacaagagga ggaggaggtg ggttttccag tcacacctca ggtacctta agaccaatga    8580 cttacaaggc agctgtagat cttagccact ttttaaaaga aaaggggggga ctggaagggc    8640 taattcactc ccaaagaaga caagatatcc ttgatctgtg gatctaccac acacaaggct    8700
acttccctga ttagcagaac tacacaccag gccaggggt cagatatcca ctgacctttg     8760
gatggtgcta caagctagta ccagttgagc cagataagat agaagaggcc aataaaggag    8820
agaacaccag cttgttacac cctgtgagcc tgcatgggat ggatgacccg agagagaag    8880 tgttagagtg gaggttttgac agccgcctag catttcatca cgtggcccga gagctgcatc    8940
cggagtactt caagaactgc tgacatcgag cttgctacaa gggactttcc gctgggact     9000 ttccagggag gcgtggcctg ggcgggactg gggagtggcg agccctcaga tcctgcatat    9060
aagcagctgc ttttgcctg tactgggtct ctctggttag accagatctg agcctgggag     9120
ctctctggct aactagggaa cccactgctt aagcctcaat aaagcttgcc ttgagtgctt    9180
c                                                                    9181

<210> SEQ ID NO 414
<211> LENGTH: 9028
<212> TYPE: DNA
<213> ORGANISM: Human immunodeficiency virus

<400> SEQUENCE: 414
aaaggcgcgg gtcggtacca gacggcgtga ggagcgggag aggaagaggc ctccggttgc      60
aggtaagtgc aacacaaaaa agaaatagct gtcttttatc caggaagggg taataagata     120
gagtgggaga tgggcgcgag aaactccgtc ttgtcaggga agaaagcaga tgaattagaa     180
aaaattaggc tacgacccaa cggaaagaaa agtacatgt tgaagcatgt agtatgggca     240
gcaaatgaat tagatagatt tggattagca gaaagcctgt tggagaacaa agaaggatgt    300
caaaaaatac tttcggtctt agctccatta gtgccaacag gctcagaaaa tttaaaaagc    360
```

```
ctttataata ctgtctgcgt catctggtgc attcacgcag aagagaaagt gaaacacact    420
gaggaagcaa aacagatagt gcagagacac ctagtggtgg aaacaggaac aacagaaact    480
atgccaaaaa caagtagacc aacagcacca tctagcggca gaggaggaaa ttacccagta    540
caacaaatag gtggtaacta tgtccacctg ccattaagcc cgagaacatt aaatgcctgg    600
gtaaaattga tagaggaaaa gaaatttgga gcagaagtag tgccaggatt tcaggcactg    660
tcagaaggtt gcacccccta tgacattaat cagatgttaa attgtgtggg agaccatcaa    720
gcggctatgc agattatcag agatattata aacgaggagg ctgcagattg ggacttgcag    780
cacccacaac cagctccaca acaaggacaa cttagggagc cgtcaggatc agatattgca    840
ggaacaacta gttcagtaga tgaacaaatc cagtggatgt acagacaaca gaaccccata    900
ccagtaggca catttacaga gatggatc caactgggt tgcaaaaatg tgtcagaatg    960
tataacccaa caaacattct agatgtaaaa caagggccaa agagccatt tcagagctat   1020
gtagacaggt tctacaaaag tttaagagca gaacagacag atgcagcagt aaagaattgg   1080
atgactcaaa cactgctgat tcaaaatgct aacccagatt gcaagctagt gctgaagggg   1140
ctgggtgtga atcccaccct agaagaaatg ctgacggctt gtcaaggagt aggggggccg   1200
ggacagaagg ctagattaat ggcagaagcc ctgaagagg ccctcgcacc agtgccaatc   1260
cctttttgcag cagcccaaca gaggggacca agaaagccaa ttaagtgttg gaattgtggg   1320
aaagagggac actctgcaag gcaatgcaga gccccaagaa gacagggatg ctggaaatgt   1380
ggaaaaatgg accatgttat ggccaaatgc ccagacagac aggcgggttt tttaggcctt   1440
ggtccatggg gaaagaagcc ccgcaatttc cccatggctc aagtgcatca ggggctgatg   1500
ccaactgctc ccccagagga cccagctgtg atctgctaa agaactacat gcagttgggc   1560
aagcagcaga gagaaaagca gagagaaagc agagagaagc cttacaagga ggtgacagag   1620
gatttgctgc acctcaattc tctctttgga ggagaccagt agtcactgct catattgaag   1680
gacagcctgt agaagtatta ctggatacag gggctgatga ttctattgta acaggaatag   1740
agttaggtcc acattatacc ccaaaaatag taggaggaat aggaggtttt attaatacta   1800
aagaatacaa aaatgtagaa atagaagttt aggcaaaaag gattaaaggg acaatcatga   1860
caggggacac cccgattaac attttttggta gaaatttgct aacagctctg gggatgtctc   1920
taaattttcc catagctaaa gtagagcctg taaaagtygc cttaaagcca ggaaaggatg   1980
gaccaaaatt gaagcagtgg ccattatcaa aagaaaagat agttgcatta agagaaatct   2040
gtgaaaagat ggaaaaggat ggtcagttgg aggaagctcc cccgaccaat ccatacaaca   2100
cccccacatt tgctataaag aaaaaggata agaacaaatg gagaatgctg atagatttta   2160
gggaactaaa tagggtcact caggacttta cggaagtcca attaggaata ccacaccctg   2220
caggactagc aaaaaggaaa agaattacag tactggatat aggtgatgca tatttctcca   2280
tacctctaga tgaagaattt aggcagtaca ctgcctttac tttaccatca gtaaataatg   2340
cagagccagg aaaacgatac atttataagg ttctgcctca gggatggaag gggtcaccag   2400
ccatcttcca atacactatg agacatgtgc tagaaccctt caggaaggca atccagatg   2460
tgaccttagt ccagtatatg gatgacatct aatagctag tgacaggaca gacctggaac   2520
atgacagggt agttttacag ttaaaggaac tcttgaatag catagggttt tctaccccag   2580
aagagaaatt ccaaaaagat cccccatttc aatggatggg gtacgaattg tggccaacaa   2640
aatgaagtt gcaaagata gagttgccac aagagagac ctgacagtg aatgatatac   2700
agaagttagt aggagtatta aattgggcag ctcaaattta tccaggtata aaaccaaac   2760
```

```
atctctgtag gttaattaga ggaaaaatga ctctaacaga ggaagttcag tggactgaga   2820
tggcagaagc agaatatgag gaaaataaaa taattctcag tcaggaacaa gaaggatgtt   2880
attaccaaga aggcaagcca ttagaagcca cggtaataaa gagtcaggac aatcagtggt   2940
cttataaaat tcaccaagaa gacaaaatac tgaaagtagg aaaatttgca agataaaga    3000 atacacatac caatggagtg agactattag cacatgtaat acagaaaata ggaaaggaag   3060
caatagtgat ctggggacag gtcccaaaat tccacttacc agttgagaag gatgtatggg   3120
aacagtggtg gacagactat tggcaggtaa cctggatacc ggaatgggat tttatctcaa   3180
caccaccgct agtaagatta gtcttcaatc tagtgaagga ccctatagag ggagaagaaa   3240
cctattatac agatggatca tgtaataaac agtcaaaaga agggaaagca ggatatatca   3300 cagataggg caaagacaaa gtaaagtgt tagaacagac tactaatcaa caagcagaat    3360
tggaagcatt tctcatggca ttgacagact cagggccaaa ggcaaatatt atagtagatt   3420
cacaatatgt tatgggaata ataacaggat gccctacaga atcagagagc aggctagtta   3480
atcaaataat agaagaaatg attaaaaagt cagaaattta tgtagcatgg gtaccagcac   3540
acaaaggtat aggaggaaac caagaaatag accacctagt tagtcaaggg attagacaag   3600
ttctcttctt ggaaaagata gagccagcac aagaagaaca tgataaatac catagtaatg   3660
taaaagaatt ggtattcaaa tttggattac ccagaatagt ggccagacag atagtagaca   3720
cctgtgataa atgtcatcag aaaggagagg ctatacatgg gcagryaaat tcagatctag   3780
ggacttggca aatggattgt acccatctag agggaaaaat aatcatagtt gcagtacatg   3840
tagctagtgg attcatagaa gcagaggtaa ttccacaaga gacaggaaga cagacagcac   3900
tatttctgtt aaaattggca ggcagatggc ctattacaca tctacacaca gataatggtg   3960
ctaactttgc ttcgcaagaa gtaaagatgg ttgcatggtg ggcagggata gagcacacct   4020 ttgggtacc atacaatcca cagagtcagg gagtagtgga agcaatgaat caccacctga   4080
aaaatcaaat agatagaatc agggaacaag caaattcagt agaaaccata gtattaatgg   4140
cagttcattg catgaatttt aaaagaaggg gaggaatagg ggatatgact ccagcagaaa   4200
gattaattaa catgatcact acagaacaag agatacaatt tcaacaatca aaaaactcaa   4260
aatttaaaaa ttttcgggtc tattacagag aaggcagaga tcaactgtgg aagggacccg   4320
gtgagctatt gtggaaaggg gaaggagcag tcatcttaaa ggtagggaca gacattaagg   4380
tagtacccag aagaaaggct aaaattatca agattatgg aggagaaaa gaggtggata    4440 gcagttccca catggaggat accggagagg ctagagaggt ggcatagcct cataaaatat   4500
ctgaaatata aaactaaaga tctacaaaag gtttgctatg tgccccattt taaggtcgga   4560
tgggcatggt ggacctgcag cagagtaatc ttcccactac aggaaggaag ccatttagaa   4620
gtacaagggt attggcattt gacaccagaa aaagggtggc tcagtactta tgcagtgagg   4680
ataacctggt actcaagaa cttttggaca gatgtaacac caaactatgc agacatttta   4740
ctgcatagca cttatttccc ttgctttaca gcgggagaag tgagaagggc catcagggga   4800
gaacaactgc tgtcttgctg caggttcccg agagctcata agtaccaggt accaagccta   4860
cagtacttag cactgaaagt agtaagcgat gtcagatccc agggagagaa tcccacctgg   4920
aaacagtgga gaagacaa taggagaggc cttcgaatgg ctaaacagaa cagtagagga    4980
gataaacaga gaggcggtaa accacctacc aaggagcta attttccagg tttggcaaag   5040
gtcttgggaa tactggcatg atgaacaagg gatgtcacca agctatgtaa aatacagata   5100
```

```
cttgtgttta atacaaaagg cttttatttat gcattgcaag aaaggctgta gatgtctagg    5160
ggaaggacat ggggcagggg gatggagacc aggacctcct cctcctcccc ctccaggact    5220
agcataaatg gaagaaagac ctccagaaaa tgaaggacca caagggaac catgggatga     5280
atgggtagtg gaggttctgg aagaactgaa agaagaagct ttaaaacatt ttgatcctcg    5340
cttgctaact gcacttggta atcatatcta taatagacat ggagacaccc ttgagggagc    5400
aggagaactc attagaatcc tccaacgagc gctcttcatg catttcagag gcggatgcat    5460
ccactccaga atcggccaac ctgggggagg aaatcctctc tcagctatac cgccctctag    5520
aagcatgcta taacacatgc tattgtaaaa agtgttgcta ccattgccag ttttgttttc    5580
ttaaaaaagg cttggggata tgttatgagc aatcacgaaa gagaagaaga actccgaaaa    5640
aggctaaggc taatacatct tctgcatcaa acaagtaagt atgggatgtc ttgggaatca    5700
gctgcttatc gccatcttgc ttttaagtgt ctatgggatc tattgtactc tatatgtcac    5760
agtcttttat ggtgtaccag cttggaggaa tgcgacaatt cccctctttt gtcaaccaa     5820
gaatagggat acttggggaa caactcagtg cctaccagat aatggtgatt attcagaaat    5880
ggcccttaat gttacagaaa gctttgatgc ctggaataat acagtcacag aacaggcaat    5940
agaggatgta tggcaactct ttgagacctc aataaggcct tgtgtaaaat tatccccatt    6000
atgcattact atgagatgca ataaaagtga gacagataga tggggattga caaaatcaat    6060
aacaacaaca gcatcaacaa catcaacgac agcatcagca aaagtagaca tggtcaatga    6120
gactagttct tgtatagccc aggataattg cacaggcttg gaacaagagc aaatgataag    6180
ctgtaaattc aacatgacag ggttaraaag agacaagaaa aaagagtaca atgaaacttg    6240
gtactctgca gatttggtat gtgaacaagg gaataacact ggtaatgaaa gtagatgtta    6300
catgaaccac tgtaacactt ctgttatcca agagtcttgt gacaaacatt attgggatgc    6360
tattagattt aggtattgtg cacctccagg ttatgctttg cttagatgta atgacacaaa    6420
ttattcaggc tttatgccta aatgttctaa ggtggtggtc tcttcatgca caaggatgat    6480
ggagacacag acttctactt ggtttggctt taatggaact agagcagaaa atagaactta    6540
tatttactgg catggtaggg ataataggac tataattagt ttaaataagt attataatct    6600
aacaatgaaa tgtagaagac aggaaataaa gacagtttta ccagtcacca ttatgtctgg    6660
attggttttc cactcacaac caatcaatga taggccaaag caggcatggt gttggtttgg    6720
aggaaaatgg aaggatgcaa taaagaggt gaagcagacc attgtcaaac atcccaggta    6780
tactggaact aacaatactg ataaaatcaa tttgacggct cctagaggag agatccgga    6840
agttaccttc atgtggacaa attgcagagg agagttcctc tactgtaaaa tgaattggtt    6900
tctaaattgg gtagaagata ggaatacagc taaccgaaag ccaaggaac agcataaaag    6960
gaattacgtg ccatgtcata ttagacaaat aatcaacact tggcataaag taggcaaaaa    7020
tgtttatttg cctccaagag agggagacct cacgtgtaac tccacagtga ccagtctcat    7080
agcaaacata gattggattg atggaaacca aactaatatc accatgagtg cagaggtggc    7140
agaactgtat cgattggaat tgggagatta taattagta gagatcactc caattggctt    7200
ggccccaca ratgtgaaga gtacactac tggtggcacc tcaagaaata aaagaggggt     7260
ctttgtgcta gggttcttgg gttttctcgc aacggcaggt tctgcaatgg cgcggcgtc    7320
gttgacgctg accgctcagt cccgaacttt attggctggg atagtgcagc aacagcaaca    7380
gctgttggac gtggtcaaga acaacaaga attgttgcga ctgaccgtct ggggaacaaa     7440
gaacctccag actagggtca ctgccatcga gaagtactta aaggaccagg cgcagctgaa    7500
```

```
tgcttgggga tgtgcgttta gacaagtctg ccacactact gtaccatggc caaatgcaag    7560
tctaacacca aagtggaaca atgagacttg gcaagagtgg gagcgaaagg ttgacttctt    7620
ggargaaaat ataacagccc tcctagagga ggcacaaatt caacaagaga agaacatgta    7680
tgaattacaa aagttgaata gctgggatgt gtttggcaat tggtttgacc ttgcttcttg    7740
gataaagtat atacaatatg gagtttatat agttgtagga gtaatactgt taagaatagt    7800
gatctatata gtacaaatgc tagctaagtt aaggcagggg tataggccag tgttctcttc    7860
cccaccctct tatttccagc agacccatat ccaacaggac ccggcactgc caaccagaga    7920
aggcaaagaa ggagacgtgt gagaaggcgg tgcaacagc tcctggcctt ggcagataga    7980
atatattcat ttcctgatcc gccaactgat acgcctcttg acttggctat tcagcaactg    8040
cagaaccttg ctatygagag tataccagat cctccaacca atactccaga ggctctctgc    8100
gaccctacag aggattcgag aagtcctcag gactgaactg gcctacctac aatatgggtg    8160
gagctatttc catgaggcgg tccaggccgt ctggagatct gcgacagaga ctcttgcggg    8220
cgcgtgggga gacttatggg agactcttag gagaggtgga agatggatac tcgcaatccc    8280
caggaggatt agacaaggc ttgagctcac tctcttgtga gggacagaaa tacaatcagg    8340
gacagtatat gaatactcca tggagaaacc cagctgaaga gagagaaaaa ttagcataca    8400
gaaaacaaaa tatggatgat atagatgagg aagatgatga cttggtaggg gtatcagtga    8460
ggccaaaagg tccctaaga acaatgagtt acaaattggc aatagacatg tctcatttta    8520
taaaagaaaa gggggactg gaagggattt attacagtgc aagaagacat agaatcttag    8580
acatatactt agaaaaggaa gaaggcatca taccagattg gcaggattac accttaggac    8640
caggaattag atwcccaaag acatttggct ggctatggaa attagtccct gtaaatgtat    8700
cagatgaggc acaggaggat gagragcatt rtttaatgca tccagctcaa acttcccagt    8760
gggatgaccc ttgggagag gttctagcat ggaagtttga tccaactctg gcctacactt    8820
atgaggcata tgttagatac ccagaagagt ttggaagcaa gtcaggcctg tcagaggaag    8880
aggttagaag aaggctaacc gcaagaggcc ttcttaacat ggctgacaag aaggaaactc    8940
gctgaaacag cagggacttt ccacaagggg atgttacggg gaggtactgg ggaggagccg    9000
gtcgggaacg cccactttct tgatgtat                                       9028
```

COMPOSITION AND METHODS FOR RAPID DETECTION OF HIV BY LOOP-MEDIATED ISOTHERMAL AMPLIFICATION (LAMP)

REFERENCE TO RELATED APPLICATION

This application claims priority from U.S. Provisional Patent Application Ser. No. 61/031,128, filed Feb. 25, 2008, the entire content of which is incorporated herein by reference.

FIELD OF THE INVENTION

The invention relates generally to rapid detection of a virus in a sample. More specifically, the invention relates to compositions and methods for rapid detection of HIV-1 and/or HIV-2 by loop-mediated isothermal amplification (LAMP) in a sample.

BACKGROUND OF THE INVENTION

Nearly 25 years since the discovery of the etiologic agent of AIDS, the HIV pandemic continues to be a major public health concern. As there is currently no available vaccine for HIV-1, much emphasis has been placed on the development of diagnostic tests to assist in the evaluation of various intervention strategies. Additionally, diagnosis of acute HIV-1 infection may have important implications for reducing the dissemination of the virus. During acute HIV infection, infected individuals are at a higher risk for transmitting the virus due to peak viral levels in blood, oral fluid and genital secretions prior to the development of an HIV-specific immune response (Pilcher et al., 2001). Though identification of early infection and intervention with antiretroviral therapy or risk-reduction counseling may reduce HIV transmission, only a very small percentage of acutely infected individuals are diagnosed within the first month of infection (Patel et al., 2006; Pilcher et al., 2004) or within the first 6 months following infection (Puchhammer-Stockl et al., 2005; Schacker et al., 1996).

The importance of diagnostic HIV tests in controlling the HIV epidemic is evidenced by the numerous tests currently licensed by the FDA, each having their own strengths and weaknesses (Ketema et al., 2005). Despite the evolving array of HIV diagnostic tests available, HIV testing algorithms have not been updated since the late 80's. Based on the previous CDC/ASTPHLD (Association of State and Territorial Public Health Laboratory Directors) guidelines, HIV testing in large patient populations frequently involves some combination of antibody-based enzyme immunoassay (EIA) test, followed by confirmation by Western Blot or indirect immunofluorescence assay (IFA) (1989).

The use of rapid HIV tests is highly attractive for screening of patient samples, especially in developing countries where resources are limited, because they are quick, easy to perform, and do not require any special equipment. Rapid tests for the identification of HIV antibody, however, will remain negative during the 4-5 week window post-infection and pre-seroconversion, necessitating the need for diagnosis based on p24 antigen or HIV-1 nucleic acid (Fiebig et al., 2003; Fiscus et al., 2007). HIV p24 antigen based tests are attractive for diagnosis of acute infection pre-seroconversion given that p24 antigen can be detected as early as 2 weeks post-infection (Weber, 2006). Due to the short window of peak viremia, antigen-based tests are relatively insensitive and are rarely used as primary screening tests for HIV (Iweala, 2004). For this reason, the EIA remains the "gold standard" for rapid, large-scale screening of clinical samples.

While the EIA is highly sensitive and relatively inexpensive, nucleic acid-based detection methods, such as PCR and RT-PCR, yield a positive result earlier in infection (Daar et al., 2001). With most HIV RNA detection assays, virus in plasma can be detected about 7 days prior to p24 antigen and about 12 days prior to antibody detection tests (Fiebig et al., 2003). Current PCR techniques, however, are not feasible screening approaches for developing countries or point-of-care testing due to personnel training requirements and the timely and expensive procedure, requiring sample processing, nucleic acid isolation, and multiple amplification steps. Furthermore, as compared to the EIA, HIV RNA assays are less specific, yielding as high as 1% false-positive rates (Hecht et al., 2002; Pilcher et al., 2004).

Thus, there is a continuing need for a rapid, cost-effective diagnostic test for the detection of early HIV infection, especially for use in resource-poor or point-of-care settings.

SUMMARY OF THE INVENTION

Methods and compositions for detection of HIV nucleic acids in a sample are provided according to embodiments of the present invention which include providing a reaction mixture including at least one LAMP, accelerated LAMP, RT-LAMP or RT-accelerated LAMP assay primer set specific for HIV-1 or HIV-2 nucleic acids and a sample to be tested for presence of HIV-1 and/or HIV-2 nucleic acids; incubating the reaction mixture under conditions suitable to produce a LAMP assay reaction product; and detecting the reaction product.

Methods for detection of HIV nucleic acids in a sample are provided according to embodiments of the present invention which include providing a reaction mixture including at least one LAMP assay primer set specific for HIV-1 or HIV-2 nucleic acids, magnesium, dNTPs, a reaction buffer, a DNA polymerase and heat-treated plasma or blood to be tested for presence of HIV-1 and/or HIV-2 nucleic acids; incubating the reaction mixture under DNA polymerase reactions conditions to produce a reaction product including amplified HIV nucleic acids; and detecting the reaction product.

In embodiments of methods of the present invention, the LAMP primer set is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets.

Optionally, the LAMP primer set includes at least one primer in the LAMP assay primer set is identical or substantially identical to a primer selected from the group consisting of SEQ ID No. 1-30, 47-58, 77-84 and 91-412.

In further embodiments of methods of the present invention, a LAMP primer set includes an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence. Optionally, the primer set further includes a LoopF primer selected from HIV-1 P24 LoopF primers of SEQ ID Nos. 155-170 or a substantially identical nucleic acid sequence and a LoopB primer selected from HIV-1 P24

LoopB primers of SEQ ID Nos. 171-174 or a substantially identical nucleic acid sequence.

In embodiments of methods of the present invention, a LAMP primer set includes an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence. Optionally, the LAMP primer set further includes a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence.

In further embodiments of methods of the present invention, a LAMP primer set includes an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence. Optionally, the LAMP primer set further includes a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

Reverse transcriptase can be included in a reaction mixture according to embodiments of the present invention.

Methods for detection of HIV nucleic acid in a sample are provided according to embodiments of the present invention which include providing a reaction mixture including a LAMP primer set specific for HIV-1 or HIV-2 nucleic acid, magnesium, dNTPs, a reaction buffer, a DNA polymerase and a sample to be tested for presence of HIV-1 and/or HIV-2 nucleic acid, wherein at least one primer of the primer set is a detectably labeled primer; incubating the reaction mixture under DNA polymerase reactions conditions to produce a reaction product mixture including a detectably labeled reaction product; and detecting the detectable label of the detectably labeled reaction product. Reverse transcriptase can be included in a reaction mixture according to embodiments of the present invention. In further embodiments, methods of the present invention include adding an oligonucleotide bonded to a quencher of the detectable label to the reaction product mixture, the reaction product mixture including detectably labeled primers unincorporated into the detectably labeled reaction product, the oligonucleotide complementary to the detectably labeled primers, thereby quenching a detectable signal from the detectably labeled primers unincorporated into the detectably labeled reaction product. Optionally, the LAMP primer set is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets. In a further option, the LAMP primer set includes at least one primer that is identical or substantially identical to a primer selected from the group consisting of SEQ ID No. 1-30, 47-58, 77-84 and 91-412. In further embodiments of methods of the present invention, a LAMP primer set includes an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence. Optionally, the primer set further includes a LoopF primer selected from HIV-1 P24 LoopF primers of SEQ ID Nos. 155-170 or a substantially identical nucleic acid sequence and a LoopB primer selected from HIV-1 P24 LoopB primers of SEQ ID Nos. 171-174 or a substantially identical nucleic acid sequence.

In embodiments of methods of the present invention, a LAMP primer set includes an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence. Optionally, the LAMP primer set further includes a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence.

In further embodiments of methods of the present invention, a LAMP primer set includes an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence. Optionally, the LAMP primer set further includes a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

Primer sets for use in a LAMP assay and specific for HIV-1 or HIV-2 nucleic acids are provided according to embodiments of the present invention where each primer set includes at least a forward inner primer, a backward inner primer, a forward outer primer and a backward outer primer, wherein each primer specifically hybridizes to a target HIV-1 or HIV-2 nucleic acid or the complement of a target HIV-1 or HIV-2 nucleic acid consistent with the function of each primer in a LAMP assay. Primer sets for use in a LAMP assay and specific for HIV-1 or HIV-2 nucleic acids are provided according to embodiments of the present invention where each primer set includes at least a forward inner primer, a backward inner primer, a forward outer primer, a backward outer primer, a LoopF primer and a Loop B primer, wherein each primer specifically hybridizes to a target HIV-1 or HIV-2 nucleic acid or the complement of a target HIV-1 or HIV-2 nucleic acid consistent with the function of each primer in a LAMP assay.

According to embodiments of the present invention, a LAMP primer set specific for HIV-1 nucleic acids, specifically hybridizes to and amplifies target HIV-1 protease, integrase, envelope or p24 nucleic acids. According to embodiments of the present invention, a LAMP primer set specific for HIV-1 nucleic acids, specifically hybridizes to and amplifies target HIV-2 pol nucleic acids. Optionally, the LAMP primer set is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets. In a further option, the LAMP primer set includes at least one primer that is identical or substantially identical to a primer selected from the group consisting of SEQ ID No. 1-30, 47-58, 77-84 and 91-412. In further embodiments of methods of the present invention, a LAMP primer set includes an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence. Optionally, the primer set further includes a LoopF primer selected from HIV-1 P24 LoopF primers of SEQ ID Nos. 155-170 or a substantially identical nucleic acid sequence and a LoopB primer selected from HIV-1 P24 LoopB primers of SEQ ID Nos. 171-174 or a substantially identical nucleic acid sequence. In further embodiments of methods of the present invention, a LAMP primer set includes an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence. Optionally, the LAMP primer set further includes a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence. In still further embodiments of methods of the present invention, a LAMP primer set includes an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence. Optionally, the LAMP primer set further includes a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

Methods for detection of HIV nucleic acids in a sample are provided according to embodiments of the present invention which include providing a reaction mixture including a LAMP primer set specific for HIV-1 or HIV-2 nucleic acid, magnesium, dNTPs, a reaction buffer, a DNA polymerase and a sample to be tested for presence of HIV-1 and/or HIV-2 nucleic acid; incubating the reaction mixture under DNA polymerase reactions conditions to produce a reaction product including amplified HIV-1 nucleic acid; and detecting the reaction product. Optionally, a reverse transcriptase is included in the reaction mixture to perform an RT-LAMP assay. A sample to be tested for presence of HIV nucleic acids is preferably obtained from a human. In embodiments of methods of the present invention, the sample includes nucleic acids isolated from a sample obtained from a subject. In further embodiments, plasma or whole blood is a sample assayed according to methods of the present invention. In still further embodiments, dried blood is a sample assayed according to methods of the present invention.

Kits for detection of HIV nucleic acids in a sample are provided according to embodiments of the present invention which include a LAMP primer set specific for HIV-1 or HIV-2 nucleic acids. In embodiments of inventive kits, the LAMP primer set is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets. In preferred embodiments, the LAMP primer set includes at least one primer that is substantially identical to a primer selected from the group consisting of SEQ ID No. 1-30, 47-58, 77-84, and 91-412.

According to embodiments of kits of the present invention, a LAMP primer set specific for HIV-1 nucleic acids, specifically hybridizes to and amplifies target HIV-1 protease, integrase, envelope or p24 nucleic acids. According to embodiments of kits the present invention, a LAMP primer set specific for HIV-2 nucleic acids, specifically hybridizes to and amplifies target HIV-2 pol nucleic acids. Optionally, a LAMP primer set included in an inventive kit is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets. In a further option, a LAMP primer set in a kit according to embodiments of the present invention includes at least one primer that is identical or substantially identical to a primer selected from the group consisting of SEQ ID No. 1-30, 47-58, 77-84 and 91-412. In further embodiments of kits of the present invention, a LAMP primer set includes an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence. Optionally, the primer set further includes a LoopF primer selected from HIV-1 P24 LoopF primers of SEQ ID Nos. 155-170 or a substantially identical nucleic acid sequence and a LoopB primer selected from HIV-1 P24 LoopB primers of SEQ ID Nos. 171-174 or a substantially identical nucleic acid sequence. In further embodiments of kits of the present invention, a LAMP primer set includes an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence. Optionally, the LAMP primer set further includes a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence. In still further embodiments of kits of the present invention, a LAMP primer set includes an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence. Optionally, the LAMP primer set further includes a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

BRIEF DESCRIPTION OF THE DRAWINGS

FIG. 4A is an image showing visualization, using a UV lamp, of a fluorescently labeled primer incorporated into amplified HIV-1 nucleic acid products in reaction tubes in which the signal from unincorporated fluorescently labeled primer is quenched by specific hybridization with a complementary quencher-bonded primer;

FIG. 4B is an image showing visualization, using a UV lamp, of a fluorescently labeled primer incorporated into amplified HIV-1 nucleic acid products in reaction tubes in which the signal from unincorporated fluorescently labeled primer is quenched by specific hybridization with a complementary quencher-bonded primer;

FIG. 4C is an image of an agarose gel including electrophoresed LAMP reaction products and controls where signal is due to a non-specific intercalator;

DETAILED DESCRIPTION OF THE PREFERRED EMBODIMENTS

Figure 1:
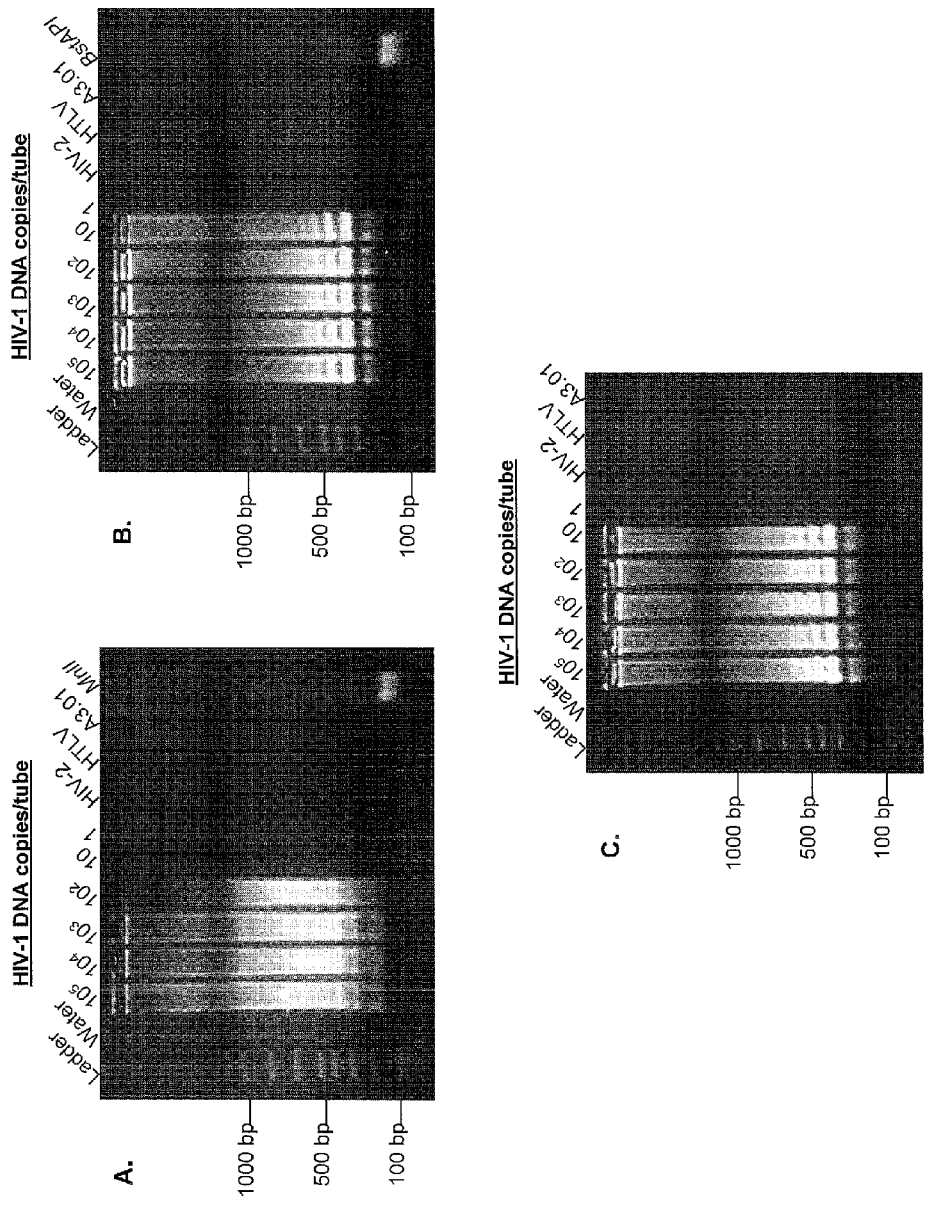
FIG. 1A is an image of an agarose gel stained with ethidium bromide showing reaction products of a method of accelerated LAMP of the present invention using a primer set specific for HIV-1 protease DNA and RNA, and using an isolated HIV-1 DNA template.
FIG. 1B is an image of an agarose gel stained with ethidium bromide showing reaction products of a method of accelerated LAMP using a primer set specific for HIV-1 p24 DNA and RNA, and using an isolated HIV-1 DNA template.
FIG. 1C is an image of an agarose gel stained with ethidium bromide showing reaction products of a method of accelerated LAMP using two primer sets in a single reaction, one primer set specific for HIV-1 protease DNA and RNA and one primer set specific for HIV-1 p24 DNA and RNA, and using an isolated HIV-1 DNA template.

Methods and compositions for LAMP assay detection of HIV-1 DNA and RNA are provided according to the present invention. Methods and compositions for LAMP assay detection of HIV-2 DNA and RNA are provided according to the present invention. Methods and compositions of the present invention provide a simple, cost-effective alternative to PCR/RT-PCR for the rapid diagnosis of infected individuals and allow for large scale screening of HIV in resource-poor field settings.

LAMP is a one step amplification reaction that amplifies a target DNA sequence with high sensitivity and specificity under isothermal conditions and exhibits sensitivity similar to traditional PCR as described in (Notomi et al., 2000). LAMP utilizes a DNA polymerase with strand displacement activity and 4 primers, specially designed for 6 specific regions within the target sequence, ensuring specificity of the amplification reaction. Furthermore, an accelerated LAMP procedure has been developed that utilizes 2 additional primers for enhanced specificity and reaction efficiency (Nagamine et al., 2002). The LAMP technology has also been adapted for the detection of RNA viruses using reverse transcription loop-mediated isothermal amplification (RT-LAMP), using a heat stable reverse transcriptase (Hong et al., 2004; Kurosaki et al., 2007; Soliman and El-Matbouli, 2006; Yoshida et al., 2007). Methods and compositions according to embodiments of the present invention include methods and compositions for standard LAMP, accelerated LAMP and RT-LAMP detection of HIV-1 DNA and RNA. Methods and compositions according to embodiments of the present invention include methods and compositions for standard LAMP, accelerated LAMP and RT-LAMP detection of HIV-2 DNA and RNA. Methods and compositions according to embodiments of the present invention include methods and compositions for standard LAMP, accelerated LAMP and RT-LAMP detection of both HIV-1 and HIV-2 DNA and RNA. The terms "LAMP assay" and "LAMP reaction" are used herein to refer generally to standard LAMP, accelerated LAMP and RT-LAMP.

Embodiments of methods and compositions of the present invention provide a rapid nucleic acid based test for the detection of HIV-1 and/or HIV-2 nucleic acid present in plasma and whole blood of infected individuals without the need for nucleic acid isolation.

Methods and compositions provided by the present invention allow detection of a lab-adapted strain of HIV-1 (BaL) as well as detection of clinical isolates using patient plasma and blood samples. Methods and compositions provided by the present invention allow detection of a lab-adapted strain of HIV-2, NIH-Z, as well as detection of clinical isolates, including, but not limited to, SLRHC and GB122, using patient plasma and blood samples.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization," "specifically hybridizes" and grammatical equivalents refer to hybridization of a particular nucleic acid to a target nucleic acid without substantial hybridization to nucleic acids other than the target nucleic acid in a sample. Primers of SEQ ID Nos. 1-58 and 65-412 and primers which are substantially identical to primers of SEQ ID Nos. 1-58 and 65-412 specifically hybridize to target HIV-1 or HIV-2 RNA and/or DNA under stringent hybridization conditions and are specific for detection of HIV nucleic acids.

Primers

Primers directed against highly conserved regions of the HIV-1 genome are provided which successfully amplify HIV-1 DNA and RNA using standard LAMP, accelerated LAMP and RT-LAMP detection of HIV-1 DNA and RNA.

Primers are provided by the present invention, which are specific for HIV-1 protease, p24, integrase or envelope genes. Primers directed against highly conserved regions of the HIV-2 genome are provided which successfully amplify HIV-2 DNA and RNA using standard LAMP, accelerated LAMP and RT-LAMP detection of HIV-2 DNA and RNA. Primers are provided by the present invention which are specific for HIV-2 pol genes.

Primers are provided according to the present invention which encompass primers which specifically and sensitively amplify and allow detection of multiple clades of HIV-1 and HIV-2. Use of the primers allows for detection of HIV-1 or HIV-2 viral particles and incorporated HIV-1 or HIV-2 proviral DNA in a cell.

The term "primer" refers to a single stranded oligonucleotide, typically about 10-60 nucleotides in length which serves as a point of initiation for template-directed DNA synthesis. One of skill in the art will recognize conditions suitable for template-directed DNA synthesis, including factors such as length of an included primer, buffer, nucleotides, pH, Mg salt concentration and temperature.

As noted above, standard LAMP, and standard RT-LAMP, utilizes 4 primers. These primers are termed forward inner primer (FIP), backward inner primer (BIP), forward outer primer (F3) and backward outer primer (B3). Compositions and methods for accelerated LAMP and accelerated RT-LAMP include two additional primers, Loop F and Loop B. The terms "forward inner primer," "FIP," "backward inner primer," "BIP," "forward outer primer," "F3," "backward outer primer," "B3," "Loop F" and "Loop B" refer to nucleic acid sequences having characteristics and functions described in detail in Notomi et al., 2000 and Nagamine et al., 2002.

Primers for LAMP provided by the present invention include nucleic acid sequences which specifically hybridize to a target HIV-1 or HIV-2 nucleic acid or the complement of a target HIV-1 or HIV-2 nucleic acid. It is noted that FIPs and BIPs each contain two such nucleic acid sequences joined by a linker wherein the linker does not hybridize either to a target HIV-1 or HIV-2 nucleic acid or to a complement of a target HIV-1 or HIV-2 nucleic acid. A linker included in FIP and BIP primers is a nucleic acid or non-nucleic acid moiety which provides flexibility between the two adjoining primers. A nucleic acid linker typically includes 2-6 nucleotides or nucleotide analogs. A non-nucleic acid moiety is illustratively a peptide, carbohydrate, lipid, polyether, polyamide, polyamide, or hydrocarbon. Exemplary non-nucleic acid linkers are described in W. Pils et al., Nucleic Acids Res., 28:1859-1863, 2000.

Each nucleic acid sequence of the primers of the present invention, which specifically hybridizes to a target HIV-1 or HIV-2 nucleic acid or the complement of a target HIV-1 or HIV-2 nucleic acid, has at least 12 contiguous nucleotides, more preferably at least 16 contiguous nucleotides, having a nucleotide sequence at least 70% complementary to 12 or more contiguous nucleotides of the target HIV-1 or HIV-2 nucleic acid or its complement, more preferably at least 80% complementary to 12 or more contiguous nucleotides of the target HIV-1 or HIV-2 nucleic acid or its complement, more preferably at least 85% complementary to 12 or more contiguous nucleotides of the target HIV-1 or HIV-2 nucleic acid or its complement, still more preferably at least 90% complementary to 12 or more contiguous nucleotides of the target HIV-1 or HIV-2 nucleic acid or its complement, and most preferably 95%, 96%, 97%, 98%, 99% or 100% complementary to 12 or more contiguous nucleotides of the target HIV-1 or HIV-2 nucleic acid or its complement.

Primers provided according to embodiments of the present invention include nucleotide sequences having SEQ ID Nos. 1-30, 47-58, 77-84 and 91-412.

In particular embodiments, a nucleic acid sequence of an HIV-1 specific primer provided according to the present invention is substantially identical to one of SEQ ID Nos. 1-30, 47-58, 77-78 and 91-412 and specifically hybridizes to a target HIV-1 nucleic acid or the complement of a target HIV-1 nucleic acid. The substantially identical nucleic acid sequence has at least 12 contiguous nucleotides, more preferably at least 16 contiguous nucleotides, having a nucleotide sequence at least 70% identical to 12 or more contiguous nucleotides of a nucleotide sequence having SEQ ID Nos. 1, 2, 5-8, 11-14, 17-26, 29, 30, 47, 48, 51-54, 57-58, 78, 91-122, 155-202, 251-292 or 361-412, more preferably at least 80% identical to 12 or more contiguous nucleotides of a nucleotide sequence having SEQ ID Nos. 1, 2, 5-8, 11-14, 17-26, 29, 30, 47, 48, 51-54, 57-58, 78, 91-122, 155-202, 251-292 or 361-412, more preferably at least 85% identical to 12 or more contiguous nucleotides of a nucleotide sequence having SEQ ID Nos. SEQ ID Nos. 1, 2, 5-8, 11-14, 17-26, 29, 30, 47, 48, 51-54, 57-58, 78, 91-122, 155-202, 251-292 or 361-412, still more preferably at least 90% identical to 12 or more contiguous nucleotides of a nucleotide sequence having SEQ ID Nos. SEQ ID Nos. 1, 2, 5-8, 11-14, 17-26, 29, 30, 47, 48, 51-54, 57-58, 78, 91-122, 155-202, 251-292 or 361-412, and most preferably 95%, 96%, 97%, 98%, 99% or 100% identical to 12 or more contiguous nucleotides of a nucleotide sequence having SEQ ID Nos. 1, 2, 5-8, 11-14, 17-26, 29, 30, 47, 48, 51-54, 57-58, 78, 91-122, 155-202, 251-292 or 361-412.

With regard to HIV-1 specific FIP and BIP primers provided by the present invention, each FIP and BIP contains two nucleic acid sequences, a first nucleic acid sequence which specifically hybridizes to a target HIV-1 nucleic acid and a second nucleic acid sequence which specifically hybridizes to the complement of a target HIV-1 nucleic acid, the first and second nucleic acid sequences joined by a linker. In particular embodiments, a nucleic acid sequence of an HIV-1 specific FIP or BIP primer provided according to the present invention is substantially identical to at least the non-linker portions of one of SEQ ID Nos. 3-4, 9-10, 15-16, 21-22, 27-28, 49-50, 55-56, 123-154, 203-250 or 293-360 and specifically hybridizes to a first target HIV-1 nucleic acid and a complement of a second target HIV-1 nucleic acid. It is noted that in each of these sequences depicted herein, the linker is denoted by lower case symbols. Thus, a substantially identical FIP or BIP primer has first and second nucleic acid non-linker sequences separated by a contiguous linker, each of the first and second nucleic acid non-linker sequences having at least 12 contiguous nucleotides, more preferably at least 16 contiguous nucleotides, having a nucleotide sequence at least 70%, 80%, 85%, 90% and most preferably 95%, 96%, 97%, 98%, 99% or 100% identical to nucleic acid non-linker sequences of 3-4, 9-10, 15-16, 21-22, 27-28, 49-50, 55-56, 123-154, 203-250 or 293-360.

In particular embodiments, the first and second nucleic acid sequences of each FIP and BIP primer of the present invention is substantially identical to SEQ ID Nos. 31 and 32, 33 and 34, 35 and 36, 37 and 38, 39 and 40, 41 and 42, 43 and 44, 45 and 46, 65 and 66, 67 and 68, 69 and 70, 71 and 72, 73 and 74, 75 and 76 or 85 and 86. The substantially identical first and second nucleic acid sequences each has at least 12 contiguous nucleotides, more preferably at least 16 contiguous nucleotides, having a nucleotide sequence at least 70%, 80%, 85%, 90% and most preferably 95%, 96%, 97%, 98%, 99% or 100% identical to 12 or more contiguous nucleotides of first and second reference nucleotide sequences, respectively, the first and second reference sequences having SEQ ID Nos. 31 and 32, 33 and 34, 35 and 36, 37 and 38, 39 and 40, 41 and 42, 43 and 44, 45 and 46, 65 and 66, 67 and 68, 69 and 70, 71 and 72, 73 and 74, 75 and 76 or 85 and 86.

In particular embodiments, a nucleic acid sequence of an HIV-2 specific primer provided according to the present invention is substantially identical to one of SEQ ID Nos. 79-84 and specifically hybridizes to a target HIV-2 nucleic acid or the complement of a target HIV-2 nucleic acid. The substantially identical nucleic acid sequence has at least 12 contiguous nucleotides, more preferably at least 16 contiguous nucleotides, having a nucleotide sequence at least 70% identical to 12 or more contiguous nucleotides of a nucleotide sequence having SEQ ID Nos. 79-84, more preferably at least 80% identical to 12 or more contiguous nucleotides of a nucleotide sequence having SEQ ID Nos. 79-84, more preferably at least 85% identical to 12 or more contiguous nucleotides of a nucleotide sequence having SEQ ID Nos. SEQ ID Nos. 79-84, still more preferably at least 90% identical to 12 or more contiguous nucleotides of a nucleotide sequence having SEQ ID Nos. SEQ ID Nos. 79-84, and most preferably 95%, 96%, 97%, 98%, 99% or 100% identical to 12 or more contiguous nucleotides of a nucleotide sequence having SEQ ID Nos. 79-84.

With regard to HIV-2 specific FIP and BIP primers provided by the present invention, each FIP and BIP contains two nucleic acid sequences, a first nucleic acid sequence which specifically hybridizes to a target HIV-2 nucleic acid and a second nucleic acid sequence which specifically hybridizes to the complement of a target HIV-1 nucleic acid, the first and second nucleic acid sequences joined by a linker as described above. In particular embodiments, a nucleic acid sequence of an HIV-2 specific FIP or BIP primer provided according to the present invention is substantially identical to at least the non-linker portions of one of SEQ ID Nos. 81-82 and specifically hybridizes to a first target HIV-2 nucleic acid and a complement of a second target HIV-2 nucleic acid. It is noted that in each of these sequences depicted herein, the linker is denoted by lower case symbols. Thus, a substantially identical FIP or BIP primer has first and second nucleic acid non-linker sequences separated by a contiguous linker, each of the first and second nucleic acid non-linker sequences having at least 12 contiguous nucleotides, more preferably at least 16 contiguous nucleotides, having a nucleotide sequence at least 70%, 80%, 85%, 90% and most preferably 95%, 96%, 97%, 98%, 99% or 100% identical to nucleic acid non-linker sequences of 81-82.

The first and second nucleic acid sequences of each FIP and BIP primer of the present invention is substantially identical to SEQ ID Nos. 87 and 88, 89 and 90. The substantially identical first and second nucleic acid sequences each has at least 12 contiguous nucleotides, more preferably at least 16 contiguous nucleotides, having a nucleotide sequence at least 70%, 80%, 85%, 90% and most preferably 95%, 96%, 97%, 98%, 99% or 100% identical to 12 or more contiguous nucleotides of first and second reference nucleotide sequences, respectively, the first and second reference sequences having SEQ ID Nos. 87 and 88, 89 and 90.

Sets of primers specific for particular HIV-1 or HIV-2 genes are provided by the present invention for use in standard or accelerated LAMP reactions. In particular embodiments, primer sets are provided which allow detection of HIV-1 p24, protease, envelope or integrase nucleic acids; and HIV-2 pol nucleic acids.

A primer set for use in LAMP to detect HIV-1 p24 nucleic acid includes nucleic acids having SEQ ID Nos. 1-4 or substantially identical nucleic acid sequences. A primer set for use in accelerated LAMP to detect HIV-1 p24 nucleic acid includes nucleic acids having SEQ ID Nos. 1-6 or substantially identical nucleic acid sequences.

A second primer set for use in LAMP to detect HIV-1 p24 nucleic acid includes nucleic acids having SEQ ID Nos. 19-22 or substantially identical nucleic acid sequences. A second primer set for use in accelerated LAMP to detect HIV-1 p24 nucleic acid includes nucleic acids having SEQ ID Nos. 19-24 or substantially identical nucleic acid sequences.

A primer set for use in LAMP to detect HIV-1 protease nucleic acid includes nucleic acids having SEQ ID Nos. 7-10 or substantially identical nucleic acid sequences. A primer set for use in accelerated LAMP to detect HIV-1 protease nucleic acid includes nucleic acids having SEQ ID Nos. 7-12 or substantially identical nucleic acid sequences.

A second primer set for use in LAMP to detect HIV-1 protease nucleic acid includes nucleic acids having SEQ ID Nos. 47-50 or substantially identical nucleic acid sequences. A second primer set for use in accelerated LAMP to detect HIV-1 protease nucleic acid includes nucleic acids having SEQ ID Nos. 47-52 or substantially identical nucleic acid sequences.

A primer set for use in LAMP to detect HIV-1 envelope nucleic acid includes nucleic acids having SEQ ID Nos. 13-16 or substantially identical nucleic acid sequences. A primer set for use in accelerated LAMP to detect HIV-1 envelope nucleic acid includes nucleic acids having SEQ ID Nos. 13-18 or substantially identical nucleic acid sequences.

A second primer set for use in LAMP to detect HIV-1 envelope nucleic acid includes nucleic acids having SEQ ID Nos. 53-56 or substantially identical nucleic acid sequences. A second primer set for use in accelerated LAMP to detect HIV-1 envelope nucleic acid includes nucleic acids having SEQ ID Nos. 53-58 or substantially identical nucleic acid sequences.

A primer set for use in LAMP to detect HIV-1 integrase nucleic acid includes nucleic acids having SEQ ID Nos. 25-28 or substantially identical nucleic acid sequences. A primer set for use in accelerated LAMP to detect HIV-1 integrase nucleic acid includes nucleic acids having SEQ ID Nos. 25-30 or substantially identical nucleic acid sequences.

A primer set for use in LAMP to detect HIV-2 pol nucleic acid includes nucleic acids having SEQ ID Nos. 79-82 or substantially identical nucleic acid sequences. A primer set for use in accelerated LAMP to detect HIV-2 pol nucleic acid includes nucleic acids having SEQ ID Nos. 79-84 or substantially identical nucleic acid sequences.

A primer set for use in LAMP to detect HIV-1 p24 nucleic acids of clades F, G and E with additional sensitivity and specificity includes nucleic acids having SEQ ID Nos. 1-3 and 77 or substantially identical nucleic acid sequences. A primer set for use in accelerated LAMP to detect HIV-1 p24 nucleic acids of clades F, G and E with additional sensitivity and specificity includes nucleic acids having SEQ ID Nos. 1-3, 5, 77 and 78 or substantially identical nucleic acid sequences.

Degenerate oligonucleotide primers are provided according to the present invention which encompass primers which specifically and sensitively amplify and allow detection of multiple clades of HIV-1.

Specific primers encoded by the HIV-1 P24 F3 degenerate primer are HIV-1 P24 F3 primers of SEQ ID Nos. 91-106. Specific primers encoded by the HIV-1 P24 B3 degenerate primer are HIV-1 P24 B3 primers of SEQ ID Nos. 107-122. Specific primers encoded by the HIV-1 P24 FIP degenerate primer are HIV-1 P24 FIP primers of SEQ ID Nos. 123-138. Specific primers encoded by the HIV-1 P24 BIP degenerate primer are HIV-1 P24 BIP primers of SEQ ID Nos. 139-154. Specific primers encoded by the HIV-1 P24 LoopF degenerate primer are HIV-1 P24 LoopF primers of SEQ ID Nos. 155-170. Specific primers encoded by the HIV-1 P24 LoopB degenerate primer are HIV-1 P24 LoopB primers of SEQ ID Nos. 171-174.

A primer set for use in LAMP to detect HIV-1 p24 nucleic acid includes an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence. A primer set for use in accelerated LAMP to detect HIV-1 P24 nucleic acid further includes a LoopF primer selected from HIV-1 P24 LoopF primers of SEQ ID Nos. 155-170 or a substantially identical nucleic acid sequence and a LoopB primer selected from HIV-1 P24 LoopB primers of SEQ ID Nos. 171-174 or a substantially identical nucleic acid sequence.

Specific primers encoded by the HIV-1 Protease F3 degenerate primer are HIV-1 Protease F3 primers of SEQ ID Nos. 175-190. Specific primers encoded by the HIV-1 Protease B3 degenerate primer are HIV-1 Protease B3 primers of SEQ ID Nos. 191-202. Specific primers encoded by the HIV-1 Protease FIP degenerate primer are HIV-1 Protease FIP primers of SEQ ID Nos. 203-218. Specific primers encoded by the HIV-1 Protease BIP degenerate primer are HIV-1 Protease BIP primers of SEQ ID Nos. 219-250. Specific primers encoded by the HIV-1 Protease LoopF degenerate primer are HIV-1 Protease LoopF primers of SEQ ID Nos. 251-254. Specific primers encoded by the HIV-1 Protease LoopB degenerate primer are HIV-1 Protease LoopB primers of SEQ ID Nos. 255-262.

A primer set for use in LAMP to detect HIV-1 Protease nucleic acid includes an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence. A primer set for use in accelerated LAMP to detect HIV-1 Protease nucleic acid further includes a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence.

Specific primers encoded by the HIV-1 Envelope F3 degenerate primer are HIV-1 Envelope F3 primers of SEQ ID Nos. 263-280. Specific primers encoded by the HIV-1 Envelope B3 degenerate primer are HIV-1 Envelope B3 primers of SEQ ID Nos. 281-292. Specific primers encoded by the HIV-1 Envelope FIP degenerate primer are HIV-1 Envelope FIP primers of SEQ ID Nos. 293-296. Specific primers encoded by the HIV-1 Envelope BIP degenerate primer are HIV-1 Envelope BIP primers of SEQ ID Nos. 297-360. Specific primers encoded by the HIV-1 Envelope LoopF degenerate primer are HIV-1 Envelope LoopF primers of SEQ ID Nos. 361-408. Specific primers encoded by the HIV-1 Envelope LoopB degenerate primer are HIV-1 Envelope LoopB primers of SEQ ID Nos. 409-412.

A primer set for use in LAMP to detect HIV-1 Envelope nucleic acid includes an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence. A primer set for use in accelerated LAMP to detect HIV-1 Envelope nucleic acid further includes a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

Biological Sample

A biological sample from any source can be assayed for HIV-1 or HIV-2 using compositions and methods of the present invention. A biological sample is typically a fluid or tissue of a mammalian subject, including a primate or human subject. A biological sample assayed for HIV-1 or HIV-2 according to the present invention illustratively includes blood, plasma, serum, lymph fluid, urine, saliva, cerebrospinal fluid, nasopharyngeal secretions, tears, milk and leukocytes. A dried fluid or tissue is a biological sample assayed in embodiments of methods according to the present invention. In embodiments, dried blood is a biological sample in an assay of the present invention.

A sample for use in methods of the present invention to detect HIV-1 or HIV-2 nucleic acid can also be nucleic acids isolated from a biological sample.

The term "isolated" refers to nucleic acids separated from substances with which the nucleic acids naturally occur. The term "isolated" does not implicate absolute purity of the HIV-1 or HIV-2 nucleic acids. In embodiments, the isolated HIV-1 or HIV-2 nucleic acids in a sample represent at least 50%, 60%, 70%, 80%, 90%, 95%, 99% or greater of the total nucleic acid content of the sample.

In embodiments of the present invention, nucleic acids are not isolated from the sample. In particular embodiments, a sample, such as blood or plasma, is heated to a temperature in the range of about 90-120° C. and nucleic acids are not isolated from the sample prior to use in a method for detection of HIV-1 or HIV-2 of the present invention.

Assay

Broadly described, a LAMP assay according to embodiments of the present invention includes combining one or more sets of primers, dNTPs, a buffer, magnesium, a DNA polymerase and a sample to be assayed for presence of HIV-1 and/or HIV-2 nucleic acid in a reaction mixture. Optionally, a reverse transcriptase is included. In a further option, a reaction enhancing additive can be included.

A primer set included in a reaction mixture is any primer set described herein. In particular embodiments of the present invention, more than one primer set is included in a reaction mixture. For example, two or more primers sets for use in LAMP to detect HIV-1 protease, p24, integrase and/or envelope nucleic acids can be included in a reaction mixture. In a further example, two or more primers sets for use in LAMP to detect HIV-1 and HIV-2 can be included in a reaction mixture.

Magnesium can be included as a magnesium salt such as magnesium acetate, magnesium chloride or magnesium sulfate.

Any buffer compatible with the reagents and reaction can be used, illustratively including sodium phosphate buffer, potassium phosphate buffer, Tris-HCl buffer and Tricine buffer.

DNA polymerases included in the reaction mixture include DNA polymerases derived from a strain of thermophilic microorganism. Preferred are DNA polymerases lacking a 5' to 3' exonuclease activity. Illustrative examples of DNA polymerases used in the present invention include *Bacillus stearothermophilus*, Bst, DNA polymerase; *Thermus, thermophilus*, Tth, DNA polymerase; *Thermus aquaticus*, Taq, DNA polymerase; *Thermococcus litoralis* DNA polymerase; *Pyrococcus furiosus*, Pfu, DNA polymerase; and *Bacillus caldotenax* DNA polymerase.

Reverse transcriptase enzymes included in the reaction mixture illustratively include Moloney murine leukemia virus, MMLV, reverse transcriptase and avian myeloblastosis virus, AMV, reverse transcriptase.

Reaction enhancing additives which can be included in the reaction mixture illustratively include betaine and DMSO.

The skilled artisan will appreciate that nucleotide analogs may be used in a reaction mixture. The term "nucleotide analog" refers to a modified or non-naturally occurring nucleotide, particularly nucleotide analogs which can be polymerized, with or without naturally occurring nucleotides, by template directed DNA synthesis. Nucleotide analogs are well-known in the art. Particular nucleotide analogs are capable of Watson-Crick pairing via hydrogen bonds with a complementary nucleotide and illustratively include, but are not limited to, those containing an analog of a nucleotide base such as substituted purines or pyrimidines, deazapurines, methylpurines, methylpyrimidines, aminopurines, aminopyrimidines, thiopurines, thiopyrimidines, indoles, pyrroles, 7-deazaguanine, 7-deazaadenine, 7-methylguanine, hypoxanthine, pseudocytosine, pseudoisocytosine, isocytosine, isoguanine, 2-thiopyrimidines, 4-thiothymine, 6-thioguanine, nitropyrrole, nitroindole, and 4-methylindole. Nucleotide analogs include those containing an analog of a deoxyribose such as a substituted deoxyribose, a substituted or non-substituted arabinose, a substituted or non-substituted xylose, and a substituted or non-substituted pyranose. Nucleotide analogs include those containing an analog of a phosphate ester such as phosphorothioates, phosphorodithioates, phosphoroamidates, phosphoroselenoates, phosophoroanilothioates, phosphoroanilidates, phosphoroamidates, boronophosphates, phosphotriesters, and alkylphosphonates such as methylphosphonates.

In one example, a reaction mixture includes 0.2 µM of each of F3 and B3 primers, 1.6 µM of each of FIP and BIP primers, 0.8 µM of each of LoopF and LoopB primers, 0.4M betaine (Sigma-Aldrich, St. Louis, Mo.), 10 mM MgSO$_4$, 1.4 mM dNTPs, 1× ThermoPol reaction buffer (New England Biolabs, Ipswich, Ma.), 8 U Bst DNA polymerase (New England Biolabs), 0.625 U AMV reverse transcriptase (Invitrogen, Carlsbad, Calif.), and 10 µl of a sample containing nucleic acids to be assayed for HIV-1 and/or HIV-2 nucleic acids is included in a reaction volume of 25 µl.

A reaction mixture is then incubated at a temperature suitable for activity of the DNA polymerase and, where included, the reverse transcriptase. The temperature depends on the particular enzymes used and the nucleotide sequence of the desired target and can be determined by one of skill in the art without undue experimentation. The reaction mixture is incubated at the appropriate temperature for a time suitable for production of amplified nucleic acid. The reaction time will depend on the reaction conditions and can be determined by one of skill in the art without undue experimentation. In general, reaction time is in the range of about 15-60 minutes but can be longer or shorter depending on factors including the amount of template nucleic acid in the sample to be tested for presence of HIV-1 and/or HIV-2 nucleic acids.

Additional sensitivity of a method for detecting HIV-1 and/or HIV-2 nucleic acids is observed when the reaction volume is increased along with concomitant increases in reactants to a volume greater than 25 microliters.

In preferred embodiments of compositions and methods of the present invention, both a DNA polymerase and a reverse transcriptase are included in a reaction mixture. In a reaction mixture containing both a DNA polymerase and a reverse transcriptase, both DNA and RNA present in the sample are amplified allowing for robust production of amplified product as well as ease of use. In particular, a reaction mixture including both a DNA polymerase and a reverse transcriptase is preferred where a whole blood sample is used since both DNA and RNA of HIV-1 and/or HIV-2 are typically present. Since the RT-LAMP method of the present invention can amplify directly from DNA as well as from reverse-transcribed RNA, proviral DNA and/or RNA can be detected in heat-treated blood samples added to the reaction without isolation of HIV-1 and/or HIV-2 nucleic acids.

The detection of proviral DNA in whole blood samples is beneficial for diagnosis of individuals past the stage of primary infection, where plasma viral loads have decreased or may become undetectable. Though viral RNA levels in the plasma may fluctuate greatly and drop past the level of detection, proviral DNA levels remain detectable throughout the course of infection (Lillo et al., 2004).

Methods of the present invention can be performed in any of a variety of assay formats, including reaction in liquid phase and/or including one or more components bonded or adsorbed to a solid phase.

Reaction Product Detection

Detection of amplified reaction products is achieved by any of various methods illustratively including detection of turbidity, fluorescence and/or electrophoresis pattern. In general, amplified reaction products produced in a reaction mixture containing a test sample, such as a sample obtained from a patient, is compared with any products produced in positive and/or negative controls.

In embodiments of the present invention, specific amplified reaction products are detected instead of, or in addition to, detection of total amplified nucleic acid in the reaction product.

In a particular embodiment, a detectably labeled primer is included in a reaction mixture and a detectably labeled reaction product is produced. A signal from the detectably labeled reaction product is detected to determine whether amplified HIV-1 and/or HIV-2 nucleic acids are produced, indicative of presence of HIV-1 and/or HIV-2 nucleic acids in the sample tested. This method allows for detection of HIV-1 and/or HIV-2 specific reaction product absent detection of non-specific products in the reaction.

The terms "detectably labeled" and "detectable label" refers to a material detectable capable of producing a signal indicative of the presence of a detectably labeled nucleic acid by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, a magnetic particle, an enzyme, a substrate, a radioisotope and a chromophore. In a preferred embodiment, a detectable label is a fluorescent label.

In a specific embodiment, a fluorescently labeled primer is included in a reaction mixture and a fluorescently labeled reaction product is produced. Fluorophores used as labels to generate a fluorescently labeled primer included in embodiments of methods and compositions of the present invention can be any of numerous fluorophores including, but not limited to, those described in Haughland, R. P., The Handbook, A Guide to Fluorescent Probes and Labeling Technologies, 10th Ed., 2005; Lakowicz, J. R., Principles of Fluorescence Spectroscopy, Springer, 3rd ed., 2006; 4-acetamido-4'-isothiocyanatostilbene-2,2' disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcouluarin (Coumaran 151); cyanosine; DAPDXYL sulfonyl chloride; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), hexachlorofluorescenin, 5-(4,6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl}amino)naphthalene-1-sulfonic acid), Malachite Green isothiocyanate;

4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethyl-carboxyrhodamine (TAMRA); tetramethyl rhodamine; tetramethyl rhodamine isothiocyanate (TRITC); riboflavin; rosolic acid and terbium chelate derivatives.

Any detection method or system operable to detect a labeled reaction product can be used in methods according to embodiments of the present invention and such appropriate detection methods and systems are well-known in the art. A signal from the fluorescently labeled reaction product is detected, for instance, using a UV light source, to determine whether amplified HIV-1 and/or HIV-2 nucleic acids are produced, indicative of presence of HIV-1 and/or HIV-2 nucleic acids in the sample tested.

In particular embodiments, following the LAMP reaction, quencher primers complementary to the fluorescently labeled primers may be added to the reaction product. Labeled primers incorporated in LAMP reaction products remain detectable following addition of the quencher primers. In contrast, fluorescently labeled primers which remain unincorporated into LAMP reaction products following a LAMP reaction hybridize with the quencher primers such that the quencher diminishes or eliminates detectable fluorescence from the fluorescently labeled primers.

The term "quencher" refers to a substance which reduces emission from a fluorescent donor when in proximity to the donor. Fluorescence is quenched when the fluorescence emitted from the fluorophore is detectably reduced, such as reduced by 10%, 20%, 30%, 40%, 50%, 60%, 70%, 80%, 90%, 95%, 99% or more.

Numerous fluorophore quenchers are known in the art, including, dabcyl; sulfonyl chlorides such as dansyl chloride; and Black Hole Quenchers BHQ-1, BHQ-2 and BHQ-3.

Additional examples of fluorophore/quencher pairs are known in the art, for instance, described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005.

A detectable label or quencher is attached to a nucleic acid by any method and at any location consistent with the function of the nucleic acid, label and quencher. A detectable label or quencher can be covalently or non-covalently bound to a nucleic acid using methods well-known in the art. Preferred is attachment of the detectable label and quencher at or near the 5' or 3' end of oligonucleotides. In further preferred embodiments, a fluorophore is covalently attached at the 5' end of a primer used in a LAMP reaction and a quencher is covalently attached to the 3' end of a complementary oligonucleotide of the same or similar length.

Attachment of detectable label or quencher can be by direct coupling to the nucleic acid or indirect, such as by an intervening spacer. A detectable label or quencher can be incorporated into a nucleic acid by any of various well-known methods such as by introduction of a fluorophore or quencher-modified base into an oligonucleotide. Methods suitable for attachment of detectable label or quencher to an oligonucleotide are exemplified in Nucleic Acids Res., 25: 2923-2929, 1997 and WO/2005/051967.

If it is desired to determine whether non-HIV-1 specific and/or non-HIV-2 specific priming took place in the LAMP reaction and whether non-HIV-1 specific and/or non-HIV-2 specific reaction products are present, a non-specific nucleic acid labeling reagent, such as ethidium bromide or Picogreen, may be used to detect total nucleic acids in a "reagent control" reaction, that is, a reaction mixture without added template RNA or DNA.

Kits

Kits including one or more reaction components are provided according to embodiments of the present invention. In particular embodiments, a kit includes at least one primer set for use in detection of HIV-1 and/or HIV-2 nucleic acids in a sample by LAMP or accelerated LAMP.

Embodiments of inventive compositions and methods are illustrated in the following examples. These examples are provided for illustrative purposes and are not considered limitations on the scope of inventive compositions and methods.

EXAMPLES

Example 1

Plasma and Blood Samples

HIV-1 seropositive plasma samples with known viral loads are obtained from ZeptoMetrix Corp., Buffalo, N.Y. (Seroconversion Panel Donor No. 62357, 60772, 65389, 68106, 65522). HIV-infected whole blood clinical specimens unlinked from personal identifiers are also used (IRB protocol #1896).

Example 2

Primer Design

HIV-1 specific outer primers (F3 and B3), forward inner primer (FIP), backward inner primer (BIP), and loop primers (LoopF and Loop B) are designed using the PrimerExplorer V3 software available on the Eiken Chemical Co. Ltd. website (http://primerexplorer.jp/e/).

The HIV-1 BaL sequence (GenBank accession number AY713409), chosen as a representative Glade B strain, is used as a reference for generating the primer sets other than FGE-optimized primers BIP-FGE and Loop B-FGE (Brown et al., 2005). Five sets of LAMP primers are designed, each recognizing a target sequence located within the HIV-1 protease, p24, integrase or envelope gene.

| HIV-1 and HIV-2 Targets | | |
|---|---|---|
| Primer Set | Region of Amplification | Amplified Sequence (5'-3') |
| HIV-1 P24 Primers | genome location 1311→ 1535 within HXB2 reference strain | attatcagaaggagccacccacaagatt taaacaccatgctaaacacagtgggggg acatcaagcagccatgcaaatgttaaaag aaaccatcaatgaggaagctgcagaatg ggatagattgcatcccgtgcaggcaggg cctgttgcaccaggccagataagagatcc aaggggaagtgacatagcaggaactacc agtaccettcaggaacaaataggatg (SEQ ID No. 59) |

| HIV-1 and HIV-2 Targets | | |
|---|---|---|
| Primer Set | Region of Amplification | Amplified Sequence (5'-3') |
| HIV-1 Protease Primers | genome location 2291→2501 within HXB2 reference strain | aaagatagggggggcaactaaaggaagct ctattagatacaggagcagatgatacagta ttagaagaaataaatttgccaggaagatg gaaaccaaaaatgatagggggaattgga ggttttatcaaagtaagacagtatgatcag atactcatagaaatctgtggacataaagct ataggtacagtattaataggacctacacct gtcaac (SEQ ID No. 60) |
| HIV-1 Envelope Primers | genome location 6321→6512 within HXB2 reference strain | aaattgtgggtcacagtctattatgggta cctgtgtgaaagaagcaaccaccactct attttgtgcatcagatgctaaagcatatgat acagaggtacataatgtttgggccacacat gcctgtgtacccacagaccccaacccaca agaagtagtattggaaaatgtgacagaaa attttaacatgtgg (SEQ ID No. 61) |
| HIV-1 Integrase Primers | genome location 4283→4474 within HXB2 reference strain | ttggagagcaatggctagtgattttaacct gcacctgtggtgcaaaagaaatagtagc cagctgtgataaatgtcagctaaaaggag aagccatgcatggacaagtagactgtagt ccaggaatatggcaactagattgtacacat ttagaaggaaaaattatcctggtagcagtt catgtagccagtgg (SEQ ID No. 62) |
| HIV-2 Pol Primers | genome location 3488→3685 within MAC239 reference strain | ggattttctaccccagatgaagttccaa aaggaccctccataccactggatgggcta tgaactgtggccaactaagtggaagctgc agaagatacagttgccccaaaaagatgta tggacagtaaatgacatccaaaagttagtg ggtgtcttaaactgggcagcacaaatctac ccagggataaaaaccagacac (SEQ ID No. 63) |

* Degenerate primers are designed to recognize the same regions as the original primer set The sequences of the specific primer sets used in this example are shown below. Conventional symbols for nucleotides are used in these sequences and R is A or G; Y is C or T; M is A or C; W is A or T; K is G or T; D is A, G or T; H is A, C or T; B is C, G or T; V is A, C or G; and S is C or G. Lower case letter x in FIP and BIP primers represents a linker. For FIP and BIP primers used in LAMP assays in examples detailed herein, x is tttt (SEQ ID No. 64).

HIV-1 P24
F3
SEQ ID No. 1
5' ATTATCAGAAGGAGCCACC 3'

B3
SEQ ID No. 2
5' CATCCTATTTGTTCCTGAAGG 3'

FIP
SEQ ID No. 3
5' CAGCTTCCTCATTGATGGTTTCTxAACACCATGCTAAACACAGT 3'

BIP
SEQ ID No. 4
5' TGTTGCACCAGGCCAGATAAxGTACTGGTAGTTCCTGCTATG 3'

BIP-FGE
SEQ ID No. 77
5' TATCCCACCAGGCCAGATAAxGTACTAGTAGTTCCTGCTATA 3'

Loop F
SEQ ID No. 5
5' TTTAACATTTGCATGGCTGCTTGAT 3'

Loop B
SEQ ID No. 6
5' GAGATCCAAGGGGAAGTGA 3'

Loop B-FGE
SEQ ID No. 78
5' GAGAACCAAGGGGAAGTGA 3'

HIV-1 Protease
F3
SEQ ID No. 7
5' AAAGATAGGGGGGCAACT 3'

B3
SEQ ID No. 8
5' GTTGACAGGTGTAGGTCCTA 3'

FIP
SEQ ID No. 9
5' GGTTTCCATCTTCCTGGCAAATTxCTCTATTAGATACAGGAGCAGA 3'

BIP
SEQ ID No. 10
5' TGATAGGGGGAATTGGAGGTTTxCCTATAGCTTTATGTCCACAGA 3'

Loop F
SEQ ID No. 11
5' TATTTCTTCTAATACTGTATCA 3'

Loop B
SEQ ID No. 12
5' TATCAAAGTAAGACAGTA 3'

HIV-1 Envelope
F3
SEQ ID No. 13
5' AAATTGTGGGTCACAGTCT 3'

B3
SEQ ID No. 14
5' CCACATGTTAAAATTTTCTGTCAC 3'

FIP
SEQ ID No. 15
5' TCATATGCTTTAGCATCTGATGCAxGGGTACCTGTGTGGAAAG 3'

BIP
SEQ ID No. 16
5' CAGAGGTACATAATGTTTGGGCCxACTACTTCTTGTGGGTTGG 3'

Loop F
SEQ ID No. 17
5' CAAAATAGAGTGGTGGTTGCT 3'

Loop B
SEQ ID No. 18
5' ACACATGCCTGTGTACCC 3'

HIV-1 P24 Degenerate
F3
SEQ ID No. 19
5' ATTAKCAGARGGAGCCAYY 3'

B3
SEQ ID No. 20
5' CATSCTATTTGYTCCTGARGR 3'

FIP
SEQ ID No. 21
5' CAGCYTCCTCATTGATGGTTTCTxAACACCATGYTAAAYAYAGT 3'

BIP
SEQ ID No. 22
5' TRTTGCACCAGGCCAGATRAxGTACTWGTAGTTCCTGCTATR 3'

Loop F
SEQ ID No. 23
5' TTTAACATYTGCATRGCTGCYTGR 3'

Loop B

SEQ ID No. 24
5' GRGAMCCAAGGGGAAGTGA 3'

HIV-1 Integrase
F3

SEQ ID No. 25
5' TTGGAGAGCAATGGCTAG 3'

B3

SEQ ID No. 26
5' CCACTGGCTACATGAACTG 3'

FIP

SEQ ID No. 27
5' GCTGACATTTATCACAGCTGGCxTGATTTTAACCTGCCACCT 3'

BIP

SEQ ID No. 28
5' GCCATGCATGGACAAGTAGACTxCTACCAGGATAATTTTTCCTTCT 3'

Loop F

SEQ ID No. 29
5' ACTATTTCTTTTGCTACCAC 3'

Loop B

SEQ ID No. 30
5' CCAGGAATATGGCAACTA 3'

HIV-1 Protease Degenerate
F3

SEQ ID No. 47
5' AARRATAGGGGGRCARCT 3'

B3

SEQ ID No. 48
5' GTTGACRGGKGTAGGTCCDA 3'

FIP

SEQ ID No. 49
5' GGTTTCCATYTYCCTGGCAAATTxCKCTATTAGAYACAGGAGCAGA 3'

BIP

SEQ ID No. 50
5' TGATAGGRGGAATTGGAGGTTTxCCTATAGCYTTWTKTCCACARA 3'

Loop F

SEQ ID No. 51
5' YATKTCTTCTAATACTGTATCA 3'

Loop B

SEQ ID No. 52
5' TATCAARGTAARACARTA 3'

HIV-1 Envelope Degenerate
F3

SEQ ID No. 53
5' MAHTTGTGGGTCACAGTHT 3'

B3

SEQ ID No. 54
5' CCACATGTTAAAMTYTTCTGTBAC 3'

FIP

SEQ ID No. 55
5' TYATATGCTTTAGCATCTGATGCAxGGGTACCTGTGTGGARAG 3'

BIP

SEQ ID No. 56
5' CAGARGTRCATAATGTYTGGGCYxWCTAYTTCTTGTGGGTTGG 3'

Loop F

SEQ ID No. 57
5' CAAAATAGRGTGGTNKTTGCD 3'

Loop B

SEQ ID No. 58
5' ACACAYGCCTGTGTACCM 3'

HIV-2 Pol
F3

SEQ ID No. 79
5' GGATTCTCTACCCCAGATGA 3'

B3

SEQ ID No. 80
5' GTGTTTGGTCTTTATCCCTG 3'

FIP

SEQ ID No. 81
5' TTCCATTTAGTTGGCCATAGTTCxGAAGTTCCAAAAAGACCCT 3'

BIP

SEQ ID No. 82
5' GAAGATACAGTTGCCCCAAAAAGAxCCAATTTAGGACACCCACTA 3'

Loop F

SEQ ID No. 83
5' AGCCCATCCAGTGGTATGG 3'

Loop B

SEQ ID No. 84
5' TGTATGGACAGTAAATGACATCCAA 3'

Portions of FIP and BIP Sequences which Hybridize Either to a Target HIV-1 or HIV-2 Nucleic Acid or to a Complement of a Target HIV-1 or HIV-2 Nucleic Acid HIV-1 P24
FIP 1st sequence SEQ ID No. 31
5' CAGCTTCCTCATTGATGGTTTCT 3'

FIP 2nd sequence

SEQ ID No. 32
5' AACACCATGCTAAACACAGT 3'

BIP 1st sequence

SEQ ID No. 33
5' TGTTGCACCAGGCCAGATAA 3'

BIP 2nd sequence

SEQ ID No. 34
5' GTACTGGTAGTTCCTGCTATG 3'

BIP-FGE 1st sequence

SEQ ID No. 85
5' TATCCCACCAGGCCAGATAA 3'

BIP-FGE 2nd sequence

SEQ ID No. 86
5' GTACTAGTAGTTCCTGCTATA 3'

HIV-1 Protease
FIP 1st sequence

SEQ ID No. 35
5' GGTTTCCATCTTCCTGGCAAATT 3'

FIP 2nd sequence

SEQ ID No. 36
5' CTCTATTAGATACAGGAGCAGA 3'

BIP 1st sequence

SEQ ID No. 37
5' TGATAGGGGGAATTGGAGGTTT 3'

BIP 2nd sequence

SEQ ID No. 38
5' CCTATAGCTTTATGTCCACAGA 3'

HIV-1 Envelope
FIP 1st sequence

5'TCATATGCTTTAGCATCTGATGCA 3'  SEQ ID No. 39

FIP 2nd sequence

5' GGGTACCTGTGTGGAAAG 3'  SEQ ID No. 40

BIP 1st sequence

5' CAGAGGTACATAATGTTTGGGCC 3'  SEQ ID No. 41

BIP 2nd sequence

5' ACTACTTCTTGTGGGTTGG 3'  SEQ ID No. 42

HIV-1 Integrase
FIP 1st sequence

5'GCTGACATTTATCACAGCTGGC 3'  SEQ ID No. 43

FIP 2nd sequence

5' TGATTTTAACCTGCCACCT 3'  SEQ ID No. 44

BIP 1st sequence

5' GCCATGCATGGACAAGTAGACT 3'  SEQ ID No. 45

BIP 2nd sequence

5' CTACCAGGATAATTTTTCCTTCT 3'  SEQ ID No. 46

HIV-1 P24 Degenerate
FIP 1st sequence

5'CAGCYTCCTCATTGATGGTTTCT 3'  SEQ ID No. 65

FIP 2nd sequence

5' AACACCATGYTAAAYAYAGT 3'  SEQ ID No. 66

BIP 1st sequence

5' TRTTGCACCAGGCCAGATRA 3'  SEQ ID No. 67

BIP 2nd sequence

5' GTACTWGTAGTTCCTGCTATR 3'  SEQ ID No. 68

HIV-1 Protease Degenerate
FIP 1st sequence

5'GGTTTCCATYTYCCTGGCAAATT 3'  SEQ ID No. 69

FIP 2nd sequence

5' CKCTATTAGAYACAGGAGCAGA 3'  SEQ ID No. 70

BIP 1st sequence

5' TGATAGGGGGAATTGGAGGTTT 3'  SEQ ID No. 71

BIP 2nd sequence

5' CCTATAGCYTTWTKTCCACARA 3'  SEQ ID No. 72

HIV-1 Envelope Degenerate
FIP 1st sequence

5' TYATATGCTTTAGCATCTGATGCA 3'  SEQ ID No. 73

FIP 2nd sequence

5' GGGTACCTGTGTGGARAG 3'  SEQ ID No. 74

BIP 1st sequence

5' CAGARGTRCATAATGTYTGGGCY 3'  SEQ ID No. 75

BIP 2nd sequence

5' WCTAYTTCTTGTGGGTTGG 3'  SEQ ID No. 76

HIV-2 Pol
FIP 1st sequence

5' TTCCATTTAGTTGGCCATAGTTC 3'  SEQ ID No. 87

FIP 2nd sequence

5' GAAGTTCCAAAAAGACCCT 3'  SEQ ID No. 88

BIP 1st sequence

5' GAAGATACAGTTGCCCCAAAAGA 3'  SEQ ID No. 89

BIP 2nd sequence

5' CCAATTTAGGACACCCACTA 3'  SEQ ID No. 90

HIV-1 P24 F3 Primers

5' ATTAGCAGAAGGAGCCACC 3'  SEQ ID No. 91

5' ATTAGCAGAAGGAGCCACT 3'  SEQ ID No. 92

5' ATTAGCAGAAGGAGCCATC 3'  SEQ ID No. 93

5' ATTAGCAGAAGGAGCCATT 3'  SEQ ID No. 94

5' ATTAGCAGAGGGAGCCACC 3'  SEQ ID No. 95

5' ATTAGCAGAGGGAGCCACT 3'  SEQ ID No. 96

5' ATTAGCAGAGGGAGCCATC 3'  SEQ ID No. 97

5' ATTAGCAGAGGGAGCCATT 3'  SEQ ID No. 98

5' ATTATCAGAAGGAGCCACC 3'  SEQ ID No. 99

5' ATTATCAGAAGGAGCCACT 3'  SEQ ID No. 100

5' ATTATCAGAAGGAGCCATC 3'  SEQ ID No. 101

5' ATTATCAGAAGGAGCCATT 3'  SEQ ID No. 102

5' ATTATCAGAGGGAGCCACC 3'  SEQ ID No. 103

5' ATTATCAGAGGGAGCCACT 3'  SEQ ID No. 104

5' ATTATCAGAGGGAGCCATC 3'  SEQ ID No. 105

5' ATTATCAGAGGGAGCCATT 3'  SEQ ID No. 106

HIV-1 P24 B3 Primers

5' CATCCTATTTGCTCCTGAAGA 3'  SEQ ID No. 107

5' CATCCTATTTGCTCCTGAAGG 3'  SEQ ID No. 108

5' CATCCTATTTGCTCCTGAGGA 3'  SEQ ID No. 109

SEQ ID No. 110
5' CATCCTATTTGCTCCTGAGGG 3'
                                              SEQ ID No. 111
5' CATCCTATTTGTTCCTGAAGA 3'
                                              SEQ ID No. 112
5' CATCCTATTTGTTCCTGAAGG 3'
                                              SEQ ID No. 113
5' CATCCTATTTGTTCCTGAGGA 3'
                                              SEQ ID No. 114
5' CATCCTATTTGTTCCTGAGGG 3'
                                              SEQ ID No. 115
5' CATGCTATTTGCTCCTGAAGA 3'
                                              SEQ ID No. 116
5' CATGCTATTTGCTCCTGAAGG 3'
                                              SEQ ID No. 117
5' CATGCTATTTGCTCCTGAGGA 3'
                                              SEQ ID No. 118
5' CATGCTATTTGCTCCTGAGGG 3'
                                              SEQ ID No. 119
5' CATGCTATTTGTTCCTGAAGA 3'
                                              SEQ ID No. 120
5' CATGCTATTTGTTCCTGAAGG 3'
                                              SEQ ID No. 121
5' CATGCTATTTGTTCCTGAGGA 3'
                                              SEQ ID No. 122
5' CATGCTATTTGTTCCTGAGGG 3'
HIV-1 P24 FIP Primers
                                              SEQ ID No. 123
5' CAGCCTCCTCATTGATGGTTTCTxAACACCATGCTAAACACAGT 3'
                                              SEQ ID No. 124
5' CAGCCTCCTCATTGATGGTTTCTxAACACCATGCTAAACATAGT 3'
                                              SEQ ID No. 125
5' CAGCCTCCTCATTGATGGTTTCTxAACACCATGCTAAATACAGT 3'
                                              SEQ ID No. 126
5' CAGCCTCCTCATTGATGGTTTCTxAACACCATGCTAAATATAGT 3'
                                              SEQ ID No. 127
5' CAGCCTCCTCATTGATGGTTTCTxAACACCATGTTAAACACAGT 3'
                                              SEQ ID No. 128
5' CAGCCTCCTCATTGATGGTTTCTxAACACCATGTTAAACATAGT 3'
                                              SEQ ID No. 129
5' CAGCCTCCTCATTGATGGTTTCTxAACACCATGTTAAATACAGT 3'
                                              SEQ ID No. 130
5' CAGCCTCCTCATTGATGGTTTCTxAACACCATGTTAAATATAGT 3'
                                              SEQ ID No. 131
5' CAGCTTCCTCATTGATGGTTTCTxAACACCATGCTAAACACAGT 3'
                                              SEQ ID No. 132
5' CAGCTTCCTCATTGATGGTTTCTxAACACCATGCTAAACATAGT 3'
                                              SEQ ID No. 133
5' CAGCTTCCTCATTGATGGTTTCTxAACACCATGCTAAATACAGT 3'
                                              SEQ ID No. 134
5' CAGCTTCCTCATTGATGGTTTCTxAACACCATGCTAAATATAGT 3'
                                              SEQ ID No. 135
5' CAGCTTCCTCATTGATGGTTTCTxAACACCATGTTAAACACAGT 3'
                                              SEQ ID No. 136
5' CAGCTTCCTCATTGATGGTTTCTxAACACCATGTTAAACATAGT 3'
                                              SEQ ID No. 137
5' CAGCTTCCTCATTGATGGTTTCTxAACACCATGTTAAATACAGT 3'
                                              SEQ ID No. 138
5' CAGCTTCCTCATTGATGGTTTCTxAACACCATGTTAAATATAGT 3'
HIV-1 P24 BIP Primers
                                              SEQ ID No. 139
5' TATTGCACCAGGCCAGATAAxGTACTAGTAGTTCCTGCTATA 3'
                                              SEQ ID No. 140
5' TATTGCACCAGGCCAGATAAxGTACTAGTAGTTCCTGCTATG 3'
                                              SEQ ID No. 141
5' TATTGCACCAGGCCAGATAAxGTACTTGTAGTTCCTGCTATA 3'
                                              SEQ ID No. 142
5' TATTGCACCAGGCCAGATAAxGTACTTGTAGTTCCTGCTATG 3'
                                              SEQ ID No. 143
5' TATTGCACCAGGCCAGATGAxGTACTAGTAGTTCCTGCTATA 3'
                                              SEQ ID No. 144
5' TATTGCACCAGGCCAGATGAxGTACTAGTAGTTCCTGCTATG 3'
                                              SEQ ID No. 145
5' TATTGCACCAGGCCAGATGAxGTACTTGTAGTTCCTGCTATA 3'
                                              SEQ ID No. 146
5' TATTGCACCAGGCCAGATGAxGTACTTGTAGTTCCTGCTATG 3'
                                              SEQ ID No. 147
5' TGTTGCACCAGGCCAGATAAxGTACTAGTAGTTCCTGCTATA 3'
                                              SEQ ID No. 148
5' TGTTGCACCAGGCCAGATAAxGTACTAGTAGTTCCTGCTATG 3'
                                              SEQ ID No. 149
5' TGTTGCACCAGGCCAGATAAxGTACTTGTAGTTCCTGCTATA 3'
                                              SEQ ID No. 150
5' TGTTGCACCAGGCCAGATAAxGTACTTGTAGTTCCTGCTATG 3'
                                              SEQ ID No. 151
5' TGTTGCACCAGGCCAGATGAxGTACTAGTAGTTCCTGCTATA 3'
                                              SEQ ID No. 152
5' TGTTGCACCAGGCCAGATGAxGTACTAGTAGTTCCTGCTATG 3'
                                              SEQ ID No. 153
5' TGTTGCACCAGGCCAGATGAxGTACTTGTAGTTCCTGCTATA 3'
                                              SEQ ID No. 154
5' TGTTGCACCAGGCCAGATGAxGTACTTGTAGTTCCTGCTATG 3'
HIV-1 P24 LoopF Primers
                                              SEQ ID No. 155
5' TTTAACATCTGCATAGCTGCCTGA 3'
                                              SEQ ID No. 156
5' TTTAACATCTGCATAGCTGCCTGG 3'
                                              SEQ ID No. 157
5' TTTAACATCTGCATAGCTGCTTGA 3'
                                              SEQ ID No. 158
5' TTTAACATCTGCATAGCTGCTTGG 3'
                                              SEQ ID No. 159
5' TTTAACATCTGCATGGCTGCCTGA 3'
                                              SEQ ID No. 160
5' TTTAACATCTGCATGGCTGCCTGG 3'
                                              SEQ ID No. 161
5' TTTAACATCTGCATGGCTGCTTGA 3'
                                              SEQ ID No. 162
5' TTTAACATCTGCATGGCTGCTTGG 3'

5' TTTAACATTTGCATAGCTGCCTGA 3'
SEQ ID No. 163

5' TTTAACATTTGCATAGCTGCCTGG 3'
SEQ ID No. 164

5' TTTAACATTTGCATAGCTGCTTGA 3'
SEQ ID No. 165

5' TTTAACATTTGCATAGCTGCTTGG 3'
SEQ ID No. 166

5' TTTAACATTTGCATGGCTGCCTGA 3'
SEQ ID No. 167

5' TTTAACATTTGCATGGCTGCCTGG 3'
SEQ ID No. 168

5' TTTAACATTTGCATGGCTGCTTGA 3'
SEQ ID No. 169

5' TTTAACATTTGCATGGCTGCTTGG 3'
SEQ ID No. 170

HIV-1 P24 LoopB Primers

5' GAGAACCAAGGGGAAGTGA 3'
SEQ ID No. 171

5' GAGACCCAAGGGGAAGTGA 3'
SEQ ID No. 172

5' GGGAACCAAGGGGAAGTGA 3'
SEQ ID No. 173

5' GGGACCCAAGGGGAAGTGA 3'
SEQ ID No. 174

HIV-1 Protease F3 Primers

5' AAAAATAGGGGGACAACT 3'
SEQ ID No. 175

5' AAAAATAGGGGGACAGCT 3'
SEQ ID No. 176

5' AAAAATAGGGGGCAACT 3'
SEQ ID No. 177

5' AAAAATAGGGGGCAGCT 3'
SEQ ID No. 178

5' AAAGATAGGGGGACAACT 3'
SEQ ID No. 179

5' AAAGATAGGGGGACAGCT 3'
SEQ ID No. 180

5' AAAGATAGGGGGCAACT 3'
SEQ ID No. 181

5' AAAGATAGGGGGCAGCT 3'
SEQ ID No. 182

5' AAGAATAGGGGGACAACT 3'
SEQ ID No. 183

5' AAGAATAGGGGGACAGCT 3'
SEQ ID No. 184

5' AAGAATAGGGGGCAACT 3'
SEQ ID No. 185

5' AAGAATAGGGGGCAGCT 3'
SEQ ID No. 186

5' AAGGATAGGGGGACAACT 3'
SEQ ID No. 187

5' AAGGATAGGGGGACAGCT 3'
SEQ ID No. 188

5' AAGGATAGGGGGCAACT 3'
SEQ ID No. 189

5' AAGGATAGGGGGCAGCT 3'
SEQ ID No. 190

HIV-1 Protease B3 Primers

5' GTTGACAGGGGTAGGTCCAA 3'
SEQ ID No. 191

5' GTTGACAGGGGTAGGTCCGA 3'
SEQ ID No. 192

5' GTTGACAGGGGTAGGTCCTA 3'
SEQ ID No. 193

5' GTTGACAGGTGTAGGTCCAA 3'
SEQ ID No. 194

5' GTTGACAGGTGTAGGTCCGA 3'
SEQ ID No. 195

5' GTTGACAGGTGTAGGTCCTA 3'
SEQ ID No. 196

5' GTTGACGGGGTAGGTCCAA 3'
SEQ ID No. 197

5' GTTGACGGGGTAGGTCCGA 3'
SEQ ID No. 198

5' GTTGACGGGGTAGGTCCTA 3'
SEQ ID No. 199

5' GTTGACGGGTGTAGGTCCAA 3'
SEQ ID No. 200

5' GTTGACGGGTGTAGGTCCGA 3'
SEQ ID No. 201

5' GTTGACGGGTGTAGGTCCTA 3'
SEQ ID No. 202

HIV-1 Protease FIP Primers

5' GGTTTCCATCTCCCTGGCAAATT<u>x</u>CGCTATTAGACACAGGAGCAGA 3'
SEQ ID No. 203

5' GGTTTCCATCTCCCTGGCAAATT<u>x</u>CGCTATTAGATACAGGAGCAGA 3'
SEQ ID No. 204

5' GGTTTCCATCTCCCTGGCAAATT<u>x</u>CTCTATTAGACACAGGAGCAGA 3'
SEQ ID No. 205

5' GGTTTCCATCTCCCTGGCAAATT<u>x</u>CTCTATTAGATACAGGAGCAGA 3'
SEQ ID No. 206

5' GGTTTCCATCTTCCTGGCAAATT<u>x</u>CGCTATTAGACACAGGAGCAGA 3'
SEQ ID No. 207

5' GGTTTCCATCTTCCTGGCAAATT<u>x</u>CGCTATTAGATACAGGAGCAGA 3'
SEQ ID No. 208

5' GGTTTCCATCTTCCTGGCAAATT<u>x</u>CTCTATTAGACACAGGAGCAGA 3'
SEQ ID No. 209

-continued

SEQ ID No. 210
5' GGTTTCCATCTTCCTGGCAAATTxCTCTATTAGATACAGGAGCAGA 3'

SEQ ID No. 211
5' GGTTTCCATTTCCCTGGCAAATTxCGCTATTAGACACAGGAGCAGA 3'

SEQ ID No. 212
5' GGTTTCCATTTCCCTGGCAAATTxCGCTATTAGATACAGGAGCAGA 3'

SEQ ID No. 213
5' GGTTTCCATTTCCCTGGCAAATTxCTCTATTAGACACAGGAGCAGA 3'

SEQ ID No. 214
5' GGTTTCCATTTCCCTGGCAAATTxCTCTATTAGATACAGGAGCAGA 3'

SEQ ID No. 215
5' GGTTTCCATTTTCCTGGCAAATTxCGCTATTAGACACAGGAGCAGA 3'

SEQ ID No. 216
5' GGTTTCCATTTTCCTGGCAAATTxCGCTATTAGATACAGGAGCAGA 3'

SEQ ID No. 217
5' GGTTTCCATTTTCCTGGCAAATTxCTCTATTAGACACAGGAGCAGA 3'

SEQ ID No. 218
5' GGTTTCCATTTTCCTGGCAAATTxCTCTATTAGATACAGGAGCAGA 3'

HIV-1 Protease BIP Primers

SEQ ID No. 219
5' TGATAGGAGGAATTGGAGGTTTxCCTATAGCCTTATGTCCACAAA 3'

SEQ ID No. 220
5' TGATAGGAGGAATTGGAGGTTTxCCTATAGCCTTATGTCCACAGA 3'

SEQ ID No. 221
5' TGATAGGAGGAATTGGAGGTTTxCCTATAGCCTTATTTCCACAAA 3'

SEQ ID No. 222
5' TGATAGGAGGAATTGGAGGTTTxCCTATAGCCTTATTTCCACAGA 3'

SEQ ID No. 223
5' TGATAGGAGGAATTGGAGGTTTxCCTATAGCCTTTTGTCCACAAA 3'

SEQ ID No. 224
5' TGATAGGAGGAATTGGAGGTTTxCCTATAGCCTTTTGTCCACAGA 3'

SEQ ID No. 225
5' TGATAGGAGGAATTGGAGGTTTxCCTATAGCCTTTTTTCCACAAA 3'

SEQ ID No. 226
5' TGATAGGAGGAATTGGAGGTTTxCCTATAGCCTTTTTTCCACAGA 3'

SEQ ID No. 227
5' TGATAGGAGGAATTGGAGGTTTxCCTATAGCTTTATGTCCACAAA 3'

SEQ ID No. 228
5' TGATAGGAGGAATTGGAGGTTTxCCTATAGCTTTATGTCCACAGA 3'

SEQ ID No. 229
5' TGATAGGAGGAATTGGAGGTTTxCCTATAGCTTTATTTCCACAAA 3'

SEQ ID No. 230
5' TGATAGGAGGAATTGGAGGTTTxCCTATAGCTTTATTTCCACAGA 3'

SEQ ID No. 231
5' TGATAGGAGGAATTGGAGGTTTxCCTATAGCTTTTTGTCCACAAA 3'

SEQ ID No. 232
5' TGATAGGAGGAATTGGAGGTTTxCCTATAGCTTTTTGTCCACAGA 3'

SEQ ID No. 233
5' TGATAGGAGGAATTGGAGGTTTxCCTATAGCTTTTTTCCACAAA 3'

SEQ ID No. 234
5' TGATAGGAGGAATTGGAGGTTTxCCTATAGCTTTTTTCCACAGA 3'

SEQ ID No. 235
5' TGATAGGGGAATTGGAGGTTTxCCTATAGCCTTATGTCCACAAA 3'

SEQ ID No. 236
5' TGATAGGGGAATTGGAGGTTTxCCTATAGCCTTATGTCCACAGA 3'

SEQ ID No. 237
5' TGATAGGGGAATTGGAGGTTTxCCTATAGCCTTATTTCCACAAA 3'

SEQ ID No. 238
5' TGATAGGGGAATTGGAGGTTTxCCTATAGCCTTATTTCCACAGA 3'

SEQ ID No. 239
5' TGATAGGGGAATTGGAGGTTTxCCTATAGCCTTTTGTCCACAAA 3'

SEQ ID No. 240
5' TGATAGGGGAATTGGAGGTTTxCCTATAGCCTTTTGTCCACAGA 3'

SEQ ID No. 241
5' TGATAGGGGAATTGGAGGTTTxCCTATAGCCTTTTTTCCACAAA 3'

SEQ ID No. 242
5' TGATAGGGGGAATTGGAGGTTTxCCTATAGCCTTTTTTCCACAGA 3'

SEQ ID No. 243
5' TGATAGGGGGAATTGGAGGTTTxCCTATAGCTTTATGTCCACAAA 3'

SEQ ID No. 244
5' TGATAGGGGGAATTGGAGGTTTxCCTATAGCTTTATGTCCACAGA 3'

SEQ ID No. 245
5' TGATAGGGGGAATTGGAGGTTTxCCTATAGCTTTATTTCCACAAA 3'

SEQ ID No. 246
5' TGATAGGGGGAATTGGAGGTTTxCCTATAGCTTTATTTCCACAGA 3'

SEQ ID No. 247
5' TGATAGGGGGAATTGGAGGTTTxCCTATAGCTTTTTGTCCACAAA 3'

SEQ ID No. 248
5' TGATAGGGGGAATTGGAGGTTTxCCTATAGCTTTTTGTCCACAGA 3'

SEQ ID No. 249
5' TGATAGGGGGAATTGGAGGTTTxCCTATAGCTTTTTTTCCACAAA 3'

SEQ ID No. 250
5' TGATAGGGGGAATTGGAGGTTTxCCTATAGCTTTTTTTCCACAGA 3'

HIV-1 Protease LoopF Primers
SEQ ID No. 251
5' CATGTCTTCTAATACTGTATCA 3'

SEQ ID No. 252
5' CATTTCTTCTAATACTGTATCA 3'

SEQ ID No. 253
5' TATGTCTTCTAATACTGTATCA 3'

SEQ ID No. 254
5' TATTTCTTCTAATACTGTATCA 3'

HIV-1 Protease LoopB Primers
SEQ ID No. 255
5' TATCAAAGTAAAACAATA 3'

SEQ ID No. 256
5' TATCAAAGTAAAACAGTA 3'

SEQ ID No. 257
5' TATCAAAGTAAGACAATA 3'

SEQ ID No. 258
5' TATCAAAGTAAGACAGTA 3'

SEQ ID No. 259
5' TATCAAGGTAAAACAATA 3'

SEQ ID No. 260
5' TATCAAGGTAAAACAGTA 3'

SEQ ID No. 261
5' TATCAAGGTAAGACAATA 3'

SEQ ID No. 262
5' TATCAAGGTAAGACAGTA 3'

HIV-1 Envelope F3 Primers
SEQ ID No. 263
5' AAATTGTGGGTCACAGTAT 3'

SEQ ID No. 264
5' AAATTGTGGGTCACAGTCT 3'

SEQ ID No. 265
5' AAATTGTGGGTCACAGTTT 3'

SEQ ID No. 266
5' AACTTGTGGGTCACAGTAT 3'

SEQ ID No. 267
5' AACTTGTGGGTCACAGTCT 3'

SEQ ID No. 268
5' AACTTGTGGGTCACAGTTT 3'

SEQ ID No. 269
5' AATTTGTGGGTCACAGTAT 3'

SEQ ID No. 270
5' AATTTGTGGGTCACAGTCT 3'

SEQ ID No. 271
5' AATTTGTGGGTCACAGTTT 3'

SEQ ID No. 272
5' CAATTGTGGGTCACAGTAT 3'

SEQ ID No. 273
5' CAATTGTGGGTCACAGTCT 3'

SEQ ID No. 274
5' CAATTGTGGGTCACAGTTT 3'

SEQ ID No. 275
5' CACTTGTGGGTCACAGTAT 3'

SEQ ID No. 276
5' CACTTGTGGGTCACAGTCT 3'

SEQ ID No. 277
5' CACTTGTGGGTCACAGTTT 3'

SEQ ID No. 278
5' CATTTGTGGGTCACAGTAT 3'

SEQ ID No. 279
5' CATTTGTGGGTCACAGTCT 3'

SEQ ID No. 280
5' CATTTGTGGGTCACAGTTT 3'

HIV-1 Envelope B3 Primers
SEQ ID No. 281
5' CCACATGTTAAAATCTTCTGTCAC 3'

SEQ ID No. 282
5' CCACATGTTAAAATCTTCTGTGAC 3'

SEQ ID No. 283
5' CCACATGTTAAAATCTTCTGTTAC 3'

SEQ ID No. 284
5' CCACATGTTAAAATTTTCTGTCAC 3'

SEQ ID No. 285
5' CCACATGTTAAAATTTTCTGTGAC 3'

SEQ ID No. 286
5' CCACATGTTAAAATTTTCTGTTAC 3'

SEQ ID No. 287
5' CCACATGTTAAACTCTTCTGTCAC 3'

-continued

SEQ ID No. 288
5' CCACATGTTAAACTCTTCTGTGAC 3'

SEQ ID No. 289
5' CCACATGTTAAACTCTTCTGTTAC 3'

SEQ ID No. 290
5' CCACATGTTAAACTTTTCTGTCAC 3'

SEQ ID No. 291
5' CCACATGTTAAACTTTTCTGTGAC 3'

SEQ ID No. 292
5' CCACATGTTAAACTTTTCTGTTAC 3'

HIV-1 Envelope FIP Primers

SEQ ID No. 293
5' TCATATGCTTTAGCATCTGATGCAxGGGTACCTGTGTGGAAAG 3'

SEQ ID No. 294
5' TCATATGCTTTAGCATCTGATGCAxGGGTACCTGTGTGGAGAG 3'

SEQ ID No. 295
5' TTATATGCTTTAGCATCTGATGCAxGGGTACCTGTGTGGAAAG 3'

SEQ ID No. 296
5' TTATATGCTTTAGCATCTGATGCAxGGGTACCTGTGTGGAGAG 3'

HIV-1 Envelope BIP Primers

SEQ ID No. 297
5' CAGAAGTACATAATGTCTGGGCCxACTACTTCTTGTGGGTTGG 3'

SEQ ID No. 298
5' CAGAAGTACATAATGTCTGGGCCxACTATTTCTTGTGGGTTGG 3'

SEQ ID No. 299
5' CAGAAGTACATAATGTCTGGGCCxTCTACTTCTTGTGGGTTGG 3'

SEQ ID No. 300
5' CAGAAGTACATAATGTCTGGGCCxTCTATTTCTTGTGGGTTGG 3'

SEQ ID No. 301
5' CAGAAGTACATAATGTCTGGGCTxACTACTTCTTGTGGGTTGG 3'

SEQ ID No. 302
5' CAGAAGTACATAATGTCTGGGCTxACTATTTCTTGTGGGTTGG 3'

SEQ ID No. 303
5' CAGAAGTACATAATGTCTGGGCTxTCTACTTCTTGTGGGTTGG 3'

SEQ ID No. 304
5' CAGAAGTACATAATGTCTGGGCTxTCTATTTCTTGTGGGTTGG 3'

SEQ ID No. 305
5' CAGAAGTACATAATGTTTGGGCCxACTACTTCTTGTGGGTTGG 3'

SEQ ID No. 306
5' CAGAAGTACATAATGTTTGGGCCxACTATTTCTTGTGGGTTGG 3'

SEQ ID No. 307
5' CAGAAGTACATAATGTTTGGGCCxTCTACTTCTTGTGGGTTGG 3'

SEQ ID No. 308
5' CAGAAGTACATAATGTTTGGGCCxTCTATTTCTTGTGGGTTGG 3'

SEQ ID No. 309
5' CAGAAGTACATAATGTTTGGGCTxACTACTTCTTGTGGGTTGG 3'

SEQ ID No. 310
5' CAGAAGTACATAATGTTTGGGCTxACTATTTCTTGTGGGTTGG 3'

SEQ ID No. 311
5' CAGAAGTACATAATGTTTGGGCTxTCTACTTCTTGTGGGTTGG 3'

SEQ ID No. 312
5' CAGAAGTACATAATGTTTGGGCTxTCTATTTCTTGTGGGTTGG 3'

SEQ ID No. 313
5' CAGAAGTGCATAATGTCTGGGCCxACTACTTCTTGTGGGTTGG 3'

SEQ ID No. 314
5' CAGAAGTGCATAATGTCTGGGCCxACTATTTCTTGTGGGTTGG 3'

SEQ ID No. 315
5' CAGAAGTGCATAATGTCTGGGCCxTCTACTTCTTGTGGGTTGG 3'

SEQ ID No. 316
5' CAGAAGTGCATAATGTCTGGGCCxTCTATTTCTTGTGGGTTGG 3'

SEQ ID No. 317
5' CAGAAGTGCATAATGTCTGGGCTxACTACTTCTTGTGGGTTGG 3'

SEQ ID No. 318
5' CAGAAGTGCATAATGTCTGGGCTxACTATTTCTTGTGGGTTGG 3'

SEQ ID No. 319
5' CAGAAGTGCATAATGTCTGGGCTxTCTACTTCTTGTGGGTTGG 3'

SEQ ID No. 320
5' CAGAAGTGCATAATGTCTGGGCTxTCTATTTCTTGTGGGTTGG 3'

SEQ ID No. 321
5' CAGAAGTGCATAATGTTTGGGCCxACTACTTCTTGTGGGTTGG 3'

SEQ ID No. 322
5' CAGAAGTGCATAATGTTTGGGCCxACTATTTCTTGTGGGTTGG 3'

SEQ ID No. 323
5' CAGAAGTGCATAATGTTTGGGCCxTCTACTTCTTGTGGGTTGG 3'

SEQ ID No. 324
5' CAGAAGTGCATAATGTTTGGGCCxTCTATTTCTTGTGGGTTGG 3'

SEQ ID No. 325
5' CAGAAGTGCATAATGTTTGGGCTxACTACTTCTTGTGGGTTGG 3'

SEQ ID No. 326
5' CAGAAGTGCATAATGTTTGGGCTxACTATTTCTTGTGGGTTGG 3'

SEQ ID No. 327
5' CAGAAGTGCATAATGTTTGGGCTxTCTACTTCTTGTGGGTTGG 3'

SEQ ID No. 328
5' CAGAAGTGCATAATGTTTGGGCTxTCTATTTCTTGTGGGTTGG 3'

SEQ ID No. 329
5' CAGAGGTACATAATGTCTGGGCCxACTACTTCTTGTGGGTTGG 3'

SEQ ID No. 330
5' CAGAGGTACATAATGTCTGGGCCxACTATTTCTTGTGGGTTGG 3'

SEQ ID No. 331
5' CAGAGGTACATAATGTCTGGGCCxTCTACTTCTTGTGGGTTGG 3'

SEQ ID No. 332
5' CAGAGGTACATAATGTCTGGGCCxTCTATTTCTTGTGGGTTGG 3'

SEQ ID No. 333
5' CAGAGGTACATAATGTCTGGGCTxACTACTTCTTGTGGGTTGG 3'

SEQ ID No. 334
5' CAGAGGTACATAATGTCTGGGCTxACTATTTCTTGTGGGTTGG 3'

SEQ ID No. 335
5' CAGAGGTACATAATGTCTGGGCTxTCTACTTCTTGTGGGTTGG 3'

SEQ ID No. 336
5' CAGAGGTACATAATGTCTGGGCTxTCTATTTCTTGTGGGTTGG 3'

SEQ ID No. 337
5' CAGAGGTACATAATGTTTGGGCCxACTACTTCTTGTGGGTTGG 3'

SEQ ID No. 338
5' CAGAGGTACATAATGTTTGGGCCxACTATTTCTTGTGGGTTGG 3'

SEQ ID No. 339
5' CAGAGGTACATAATGTTTGGGCCxTCTACTTCTTGTGGGTTGG 3'

SEQ ID No. 340
5' CAGAGGTACATAATGTTTGGGCCxTCTATTTCTTGTGGGTTGG 3'

```
                                      SEQ ID No. 341                    SEQ ID No. 367
5' CAGAGGTACATAATGTTTGGGCTxACTACTTCTTGTGGGTTGG 3'    5' CAAAATAGAGTGGTTGTTGCA 3'

SEQ ID No. 342                    SEQ ID No. 368
5' CAGAGGTACATAATGTTTGGGCTxACTATTTCTTGTGGGTTGG 3'    5' CAAAATAGAGTGGTTGTTGCG 3'

SEQ ID No. 343                    SEQ ID No. 369
5' CAGAGGTACATAATGTTTGGGCTxTCTACTTCTTGTGGGTTGG 3'    5' CAAAATAGAGTGGTTGTTGCT 3'

SEQ ID No. 344                    SEQ ID No. 370
5' CAGAGGTACATAATGTTTGGGCTxTCTATTTCTTGTGGGTTGG 3'    5' CAAAATAGAGTGGTTTTTGCA 3'

SEQ ID No. 345                    SEQ ID No. 371
5' CAGAGGTGCATAATGTCTGGGCCxACTACTTCTTGTGGGTTGG 3'    5' CAAAATAGAGTGGTTTTTGCG 3'

SEQ ID No. 346                    SEQ ID No. 372
5' CAGAGGTGCATAATGTCTGGGCCxACTATTTCTTGTGGGTTGG 3'    5' CAAAATAGAGTGGTTTTTGCT 3'

SEQ ID No. 347                    SEQ ID No. 373
5' CAGAGGTGCATAATGTCTGGGCCxTCTACTTCTTGTGGGTTGG 3'    5' CAAAATAGAGTGGTGGTTGCA 3'

SEQ ID No. 348                    SEQ ID No. 374
5' CAGAGGTGCATAATGTCTGGGCCxTCTATTTCTTGTGGGTTGG 3'    5' CAAAATAGAGTGGTGGTTGCG 3'

SEQ ID No. 349                    SEQ ID No. 375
5' CAGAGGTGCATAATGTCTGGGCTxACTACTTCTTGTGGGTTGG 3'    5' CAAAATAGAGTGGTGGTTGCT 3'

SEQ ID No. 350                    SEQ ID No. 376
5' CAGAGGTGCATAATGTCTGGGCTxACTATTTCTTGTGGGTTGG 3'    5' CAAAATAGAGTGGTGTTTGCA 3'

SEQ ID No. 351                    SEQ ID No. 377
5' CAGAGGTGCATAATGTCTGGGCTxTCTACTTCTTGTGGGTTGG 3'    5' CAAAATAGAGTGGTGTTTGCG 3'

SEQ ID No. 352                    SEQ ID No. 378
5' CAGAGGTGCATAATGTCTGGGCTxTCTATTTCTTGTGGGTTGG 3'    5' CAAAATAGAGTGGTGTTTGCT 3'

SEQ ID No. 353                    SEQ ID No. 379
5' CAGAGGTGCATAATGTTTGGGCCxACTACTTCTTGTGGGTTGG 3'    5' CAAAATAGAGTGGTCGTTGCA3'

SEQ ID No. 354                    SEQ ID No. 380
5' CAGAGGTGCATAATGTTTGGGCCxACTATTTCTTGTGGGTTGG 3'    5' CAAAATAGAGTGGTCGTTGCG 3'

SEQ ID No. 355                    SEQ ID No. 381
5' CAGAGGTGCATAATGTTTGGGCCxTCTACTTCTTGTGGGTTGG 3'    5' CAAAATAGAGTGGTCGTTGCT 3'

SEQ ID No. 356                    SEQ ID No. 382
5' CAGAGGTGCATAATGTTTGGGCCxTCTATTTCTTGTGGGTTGG 3'    5' CAAAATAGAGTGGTCTTTGCA 3'

SEQ ID No. 357                    SEQ ID No. 383
5' CAGAGGTGCATAATGTTTGGGCTxACTACTTCTTGTGGGTTGG 3'    5' CAAAATAGAGTGGTCTTTGCG 3'

SEQ ID No. 358                    SEQ ID No. 384
5' CAGAGGTGCATAATGTTTGGGCTxACTATTTCTTGTGGGTTGG 3'    5' CAAAATAGAGTGGTCTTTGCT 3'

SEQ ID No. 359                    SEQ ID No. 385
5' CAGAGGTGCATAATGTTTGGGCTxTCTACTTCTTGTGGGTTGG 3'    5' CAAAATAGGGTGGTAGTTGCA 3'

SEQ ID No. 360                    SEQ ID No. 386
5' CAGAGGTGCATAATGTTTGGGCTxTCTATTTCTTGTGGGTTGG 3'    5' CAAAATAGGGTGGTAGTTGCG 3'

HIV-1 Envelope LoopF Primers                                            SEQ ID No. 387
                                      SEQ ID No. 361    5' CAAAATAGGGTGGTAGTTGCT 3'
5' CAAAATAGAGTGGTAGTTGCA 3'
                                      SEQ ID No. 362                    SEQ ID No. 388
5' CAAAATAGAGTGGTAGTTGCG 3'                          5' CAAAATAGGGTGGTATTTGCA 3'

SEQ ID No. 363                    SEQ ID No. 389
5' CAAAATAGAGTGGTAGTTGCT 3'                          5' CAAAATAGGGTGGTATTTGCG 3'

SEQ ID No. 364                    SEQ ID No. 390
5' CAAAATAGAGTGGTATTTGCA 3'                          5' CAAAATAGGGTGGTATTTGCT 3'

SEQ ID No. 365                    SEQ ID No. 391
5' CAAAATAGAGTGGTATTTGCG 3'                          5' CAAAATAGGGTGGTTGTTGCA 3'

SEQ ID No. 366                    SEQ ID No. 392
5' CAAAATAGAGTGGTATTTGCT 3'                          5' CAAAATAGGGTGGTTGTTGCG 3'

SEQ ID No. 393
                                                     5' CAAAATAGGGTGGTTGTTGCT 3'
```

-continued

5' CAAAATAGGGTGGTTTTTGCA 3'  SEQ ID No. 394

5' CAAAATAGGGTGGTTTTTGCG 3'  SEQ ID No. 395

5' CAAAATAGGGTGGTTTTTGCT 3'  SEQ ID No. 396

5' CAAAATAGGGTGGTGGTTGCA 3'  SEQ ID No. 397

5' CAAAATAGGGTGGTGGTTGCG 3'  SEQ ID No. 398

5' CAAAATAGGGTGGTGGTTGCT 3'  SEQ ID No. 399

5' CAAAATAGGGTGGTGTTTGCA 3'  SEQ ID No. 400

5' CAAAATAGGGTGGTGTTTGCG 3'  SEQ ID No. 401

5' CAAAATAGGGTGGTGTTTGCT 3'  SEQ ID No. 402

5' CAAAATAGGGTGGTCGTTGCA 3'  SEQ ID No. 403

5' CAAAATAGGGTGGTCGTTGCG 3'  SEQ ID No. 404

5' CAAAATAGGGTGGTCGTTGCT 3'  SEQ ID No. 405

5' CAAAATAGGGTGGTCTTTGCA 3'  SEQ ID No. 406

5' CAAAATAGGGTGGTCTTTGCG 3'  SEQ ID No. 407

5' CAAAATAGGGTGGTCTTTGCT 3'  SEQ ID No. 408

HIV-1 Envelope LoopB Primers

5' ACACACGCCTGTGTACCA 3'  SEQ ID No. 409

5' ACACACGCCTGTGTACCC 3'  SEQ ID No. 410

5' ACACATGCCTGTGTACCA 3'  SEQ ID No. 411

5' ACACATGCCTGTGTACCC 3'  SEQ ID No. 412

The LAMP primers used in these examples are synthesized by Sigma-Genosys (St. Louis, Mo.).

Example 3

Nucleic Acid Isolation

Total DNA or RNA is isolated using a QIAamp DNA blood mini kit or Viral RNA mini kit (QIAGEN, Valencia, Calif.), respectively, according to the manufacturer's protocol. To determine sensitivity of the RT-LAMP reaction for DNA, isolations are performed on OM10.1 cells, a human monocytic cell line latently infected with HIV-1 (Butera et al., 1991). Negative controls included isolated DNA from PBMC infected with SLRHC HIV-2, the HTLV-1 infected cell line MT-2, and the human T-cell line A3.01 (Buttke and Folks, 1992; Folks et al., 1985).

For determining RNA sensitivity, RNA isolated from an OptiQuant® HIV-1 RNA Quantification Panel (Acrometrix, Benicia, Ca.) is evaluated. Sensitivity for primary HIV-1 isolates is determined using isolated RNA from patient plasma or blood samples. Negative RNA controls included RNA isolated from HIV-2, HTLV-1 or HTLV-2 (ABI, Columbia, Md.) viral stocks, and HIV-1 seronegative plasma and blood samples. Eluted nucleic acid is stored at −80° C. until ready for use.

Example 4

Optimization of RT-LAMP Reaction Conditions

Optimization of the RT-LAMP reaction is carried out by evaluating different concentrations of betaine (0.2-0.8M) and $MgSO_4$ (6-10 mM) in the reaction mix, and a range of amplification temperatures (58-63° C.).

The minimum amplification time required for maximum sensitivity is determined for both DNA and RNA, using the HIV-1 protease primers of SEQ ID Nos 7-12 and HIV-1 p24 primers of SEQ ID Nos 1-6 in combination. The target DNA or RNA is added to the reaction in 10-fold dilutions and amplification is performed for 15, 30, 45, or 60 minutes. Table I shows results of this test.

TABLE I

| Nucleic Acid | Copies/tube | Test result for RT-LAMP reaction time | | | |
|---|---|---|---|---|---|
| | | 15 min | 30 min | 45 min | 60 min |
| DNA | 1,000 | − | + | + | + |
| | 100 | − | + | + | + |
| | 10 | − | − | − | + |
| | 0 | − | − | − | − |
| RNA | 10,000 | − | + | + | + |
| | 1,000 | − | + | + | + |
| | 100 | − | − | − | + |
| | 0 | − | − | − | − |

Example 5

RT-LAMP Amplification

The RT-LAMP reaction to detect HIV-1 and/or HIV-2 is carried out in a 25 µl volume (total), unless otherwise stated, containing the following components: 0.2 µM of each F3 and B3 primers, 1.6 µM of each FIP and BIP primers, 0.8 µM of each LoopF and LoopB primers, 0.4M betaine (Sigma-Aldrich, St. Louis, Mo.), 10 mM $MgSO_4$, 1.4 mM dNTPs, 1× ThermoPol reaction buffer (New England Biolabs, Ipswich, Ma.), 8 U Bst DNA polymerase (New England Biolabs), 0.625 U AMV reverse transcriptase (Invitrogen, Carlsbad, Calif.), and 10 µl of extracted nucleic acid or heated plasma/blood. RT-LAMP amplification is carried out using a GeneAmp® PCR System (Applied Biosystems, Foster City, Calif.). The reaction mixture is heated at 60° C. for 60 minutes and then held at 80° C. for 2 minutes to terminate the reaction. Negative controls are included in each run, including a water control to check for cross-contamination.

Example 6

Identification of amplified DNA product is determined by gel electrophoresis on a 1.2% agarose gel, followed by staining with ethidium bromide and visualization on a UV transilluminator. Additionally, the presence of amplified product is confirmed visually following the addition of the fluorescent nucleic acid stain PicoGreen (Invitrogen). A 1:200 dilution of PicoGreen in Tris-EDTA (TE) is added to the reaction mixture and the reaction tubes are evaluated using a UV lamp.

Example 7

RT-LAMP Specificity

Amplification specificity is determined by restriction digest of LAMP products. Based on consensus sequence alignments, the restriction enzymes MnII and BstAPI (New England Biolabs) are used to digest amplified LAMP products produced by the HIV-1 protease and HIV-1 p24 primers, respectively. The restriction digests are incubated for 1 hour at 37° C., using the appropriate buffer specified by the manufacturer. Digested products are analyzed by gel electrophoresis on a 1.2% agarose gel.

Example 8

Sensitivity and Specificity of the HIV RT-LAMP Assay to DNA

DNA is extracted from OM10.1 cells and tested by RT-LAMP using HIV-2, HTLV, and A3.01 DNA as negative controls. The sensitivity of the HIV-1 specific RT-LAMP assay for DNA detection is determined using 10-fold dilutions of extracted DNA from OM10.1 cells with HIV-1 protease or HIV-1 p24 specific primers. The HIV-1 protease and HIV-1 p24 primers sets are also evaluated in reactions using the combined primer sets. Amplified LAMP products and restriction digests are analyzed by agarose gel electrophoresis. FIGS. 1A. 1B and 1C show images of the resulting agarose gels for each primer set and the laddering pattern typical of successful LAMP is observed, indicating the various replicating intermediates of the stem-loop amplification process. The standard ladder shown is a 2,000 bp DNA ladder commercially available from Bio-Rad Laboratories, Hercules, Calif.

The limit of detection for both the HIV-1 protease and HIV-1 p24 primers ranged from 100 to 10 DNA copies/tube, depending on the experiment. Analysis of the agarose gel in FIG. 1A shows a sensitivity of 100 copies/tube for the HIV-1 protease primers and 10 copies/tube for the HIV-1 p24 primers as shown in FIG. 1B.

The HIV-1 protease and HIV-1 p24 primer sets are also tested in combination and the RT-LAMP assay exhibits a comparable sensitivity as when the primers are used individually as shown in FIG. 1C. The level of detection of the HIV RT-LAMP assay for extracted DNA using HIV-1 p24 and/or HIV-1 protease primer sets is determined to be between 10 and 100 DNA copies/tube or $10^3$-$10^4$ copies/ml.

Amplification from HIV-2, HTLV-1 and A3.01 DNA is not observed.

The specificity of the HIV-1 protease and HIV-1 p24 primers is evaluated by digesting the amplified products from DNA or RNA with specific restriction enzymes, MnII and BstAPI, that recognized sites within the amplified target sequence. Following the digestion, the LAMP-specific laddering pattern disappeared, indicating complete digestion of the amplified product as shown in FIG. 1A and in FIG. 1B.)

Similar procedures are used for other HIV-1 specific primers to obtain similar HIV-1 specific results and for HIV-2 specific primers to obtain similar HIV-2 specific results.

Example 9

Sensitivity and Specificity of the HIV RT-LAMP Using RNA

The sensitivity of RT-LAMP for the detection of RNA is also determined, using extracted RNA from an RNA quantification panel consisting of 10-fold dilutions of HIV-1 in seronegative plasma. RNA is extracted from an OptiQuant® HIV-1 RNA Quantification Panel and tested by RT-LAMP using HIV-1 protease primers (A), HIV-1 p24 primers (B), and both primer sets used in combination (C). HIV-2 and HTLV RNA are used as negative controls. Amplified LAMP products and restriction digests are analyzed by agarose gel electrophoresis.

Figure 2:
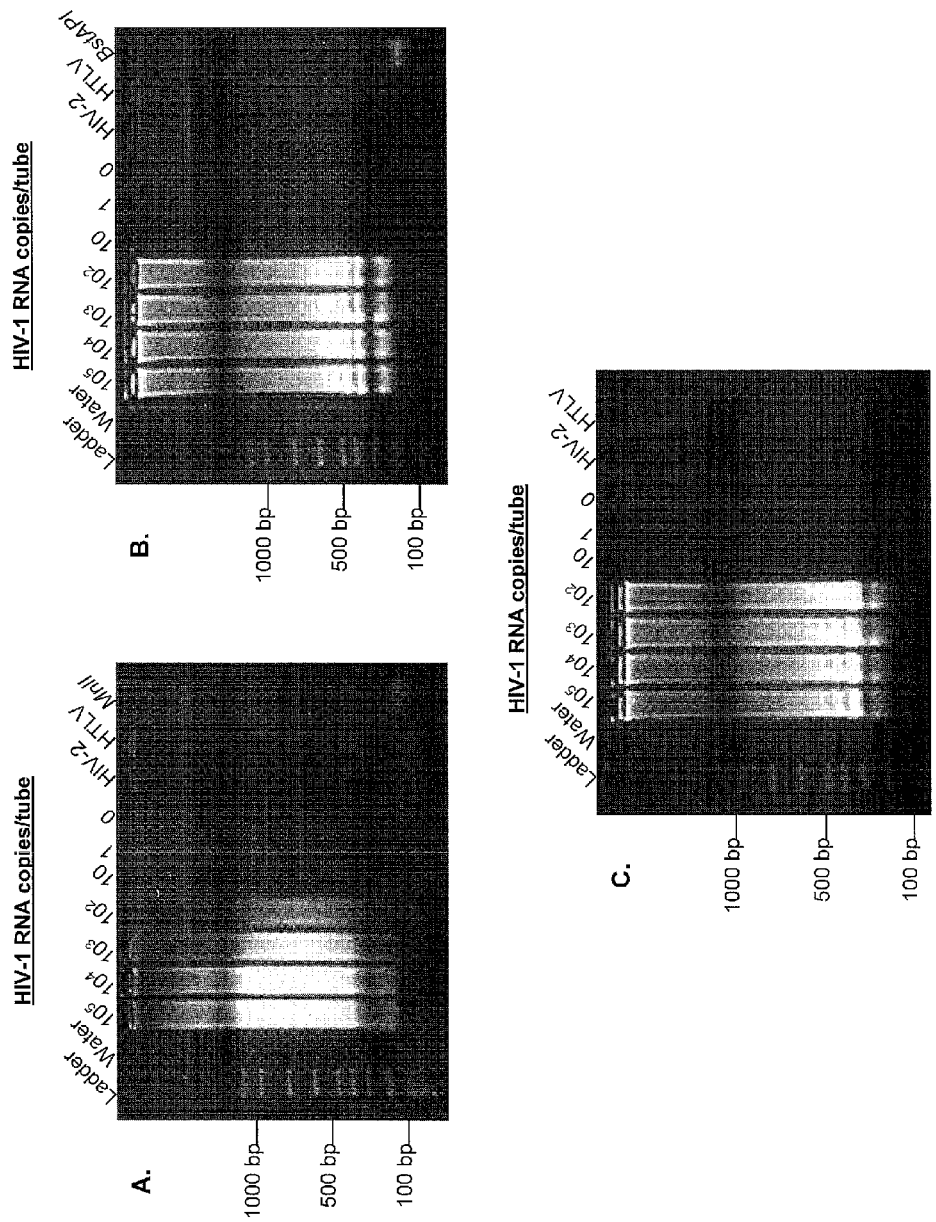
FIG. 2A is an image of an agarose gel stained with ethidium bromide showing reaction products of a method of accelerated RT-LAMP of the present invention using a primer set specific for HIV-1 protease DNA and RNA, and using isolated HIV-1 RNA template.
FIG. 2B is an image of an agarose gel stained with ethidium bromide showing reaction products of a method of accelerated RT-LAMP using a primer set specific for HIV-1 p24 DNA and RNA, and using an isolated HIV-1 RNA template.
FIG. 2C is an image of an agarose gel stained with ethidium bromide showing reaction products of a method of accelerated RT-LAMP using two primer sets in a single reaction, one primer set specific for HIV-1 protease DNA and RNA and one primer set specific for HIV-1 p24 DNA and RNA, and using an isolated HIV-1 RNA template.

FIGS. 2A-C show images of the resulting agarose gels for each primer set and the laddering pattern typical of successful LAMP is observed, indicating the various replicating intermediates of the stem-loop amplification process. The standard ladder shown is a 2,000 bp DNA ladder commercially available from Bio-Rad Laboratories, Hercules, Calif.

The limit of detection for both the HIV-1 protease and HIV-1 p24 primers ranges from 100 to 1000 RNA copies/tube depending on the experiment. A sensitivity of 100 copies of RNA/tube is shown in FIG. 2A for the HIV-1 protease primer set and in FIG. 2B for the HIV-1 p24 primer set. Similar to the results for DNA, the HIV-1 protease and HIV-1 p24 primers exhibit comparable sensitivity for RNA when used in combination as compared to the limit of detection when tested individually as seen in FIG. 2C. Amplification from HIV-2 and HTLV-1 RNA is not observed using HIV-1 specific primers.

The specificity of the HIV-1 protease and HIV-1 p24 primers is evaluated by digesting the amplified products from DNA or RNA with specific restriction enzymes, MnII and BstAPI, that recognized sites within the amplified target sequence. Following the digestion, the LAMP-specific laddering pattern disappeared, indicating complete digestion of the amplified product, shown in FIG. 2A and in FIG. 2B.

The sensitivity of the assay for HIV-1 RNA is determined to range from 100-1000 RNA copies/tube, which equates to a viral load detection limit of $10^4$-$10^5$ viral copies/ml when using a 25 µl final reaction volume.

Similar procedures are used for other HIV-1 specific primers to obtain similar HIV-1 specific results and for HIV-2 specific primers to obtain similar HIV-2 specific results.

Example 10

Detection of Primary HIV-1 Strains in Infected Plasma and Blood Samples

RNA is extracted from HIV seropositive plasma (FIG. 3A) and blood (FIG. 3B) samples with known viral load and tested by RT-LAMP using HIV-1 protease and HIV-1 p24 primers in combination. Plasma samples with viral loads ranging from $5.3 \times 10^5$/ml to $5.6 \times 10^3$/ml, as determined by HIV RNA bDNA (Chiron, Everyville, Calif.), are evaluated to determine the limit of detection. Similarly, whole blood samples with viral loads ranging from $4.8 \times 10^5$/ml to $2 \times 10^3$/ml, as determined by Roche COBAS Amplicor, are also evaluated. HIV seronegative plasma and blood samples are used as negative controls. Results are analyzed by agarose gel electrophoresis and PicoGreen staining and are shown in FIGS. 3A-C.

FIG. 3A shows that HIV-1 RNA is detected in 4 out of the 5 seropositive plasma samples by RT-LAMP, with the lowest detectable sample containing 580 RNA copies/tube. Three out of the 5 HIV positive blood samples are detected, with the last detectable sample containing $1.1 \times 10^3$ RNA copies/tube as shown in FIG. 3B. These results are consistent with the 100-1000 copy/tube sensitivity observed with the RNA quantification panel. Visual identification of amplified LAMP product is also possible through the addition of the fluorescent nucleic acid stain PicoGreen, which yielded results consistent to those obtained by agarose gel electrophoresis.

Similar procedures are used for other HIV-1 specific primers to obtain similar HIV-1 specific results and for HIV-2 specific primers to obtain similar HIV-2 specific results.

Example 11

Increased Sensitivity with Increased Reaction Volume

The sensitivity of detection can be increased by increasing the overall reaction volume. Ten-fold dilutions of extracted RNA are tested in a 25 µl RT-LAMP reaction volume using the reaction mixture as described in Example 5, and compared to reactions in which target RNA and reagents are increased 4-fold for a total reaction volume of 100 microliters. HIV-2 and HTLV RNA are used as negative controls. A 10-fold increase in sensitivity is observed when the reaction volume is increased from 25 µl to 100 µl as shown in Table II.

TABLE II

| | | Test result for RT-LAMP volume | |
|---|---|---|---|
| Target RNA | Copies/ml | 25 µl | 100 µl |
| HIV-1 | 100,000 | + | + |
| | 10,000 | + | + |
| | 1,000 | − | + |
| | 0 | − | − |
| HIV-2 | ND | − | − |
| HTLV | ND | − | − |

Similar procedures are used for other HIV-1 specific primers to obtain similar HIV-1 specific results and for HIV-2 specific primers to obtain similar HIV-2 specific results.

During acute HIV-1 infection, the plasma viral load can vary greatly, ranging from around $10^3$-$10^8$ viral copies/ml (Fiscus et al., 2007; Pilcher et al., 2001). Thus, increasing the reaction volume from 25 µl to 100 µl, allows for the detection of the lower range of viral loads characteristic of acute infection in a subject.

Example 12

Detection of HIV-1 and/or HIV-2 Nucleic Acids in Heat-Treated Plasma and Blood

Detection of HIV-1 and/or HIV-2 in patient samples is performed by adding heat-treated plasma and blood directly into the LAMP reaction.

The optimal temperatures for each sample type is first determined by evaluating temperatures in the range of 90-120° C. Plasma samples are diluted 1:3 (for a final volume of 200 µl) in RNase free water to prevent coagulation and heated at 100° C. for 5 minutes in a heat block. Whole blood samples are diluted 1:5 (for a final volume of 200 µl) in water and heated at 117° C. for 5 minutes.

Figure 3:
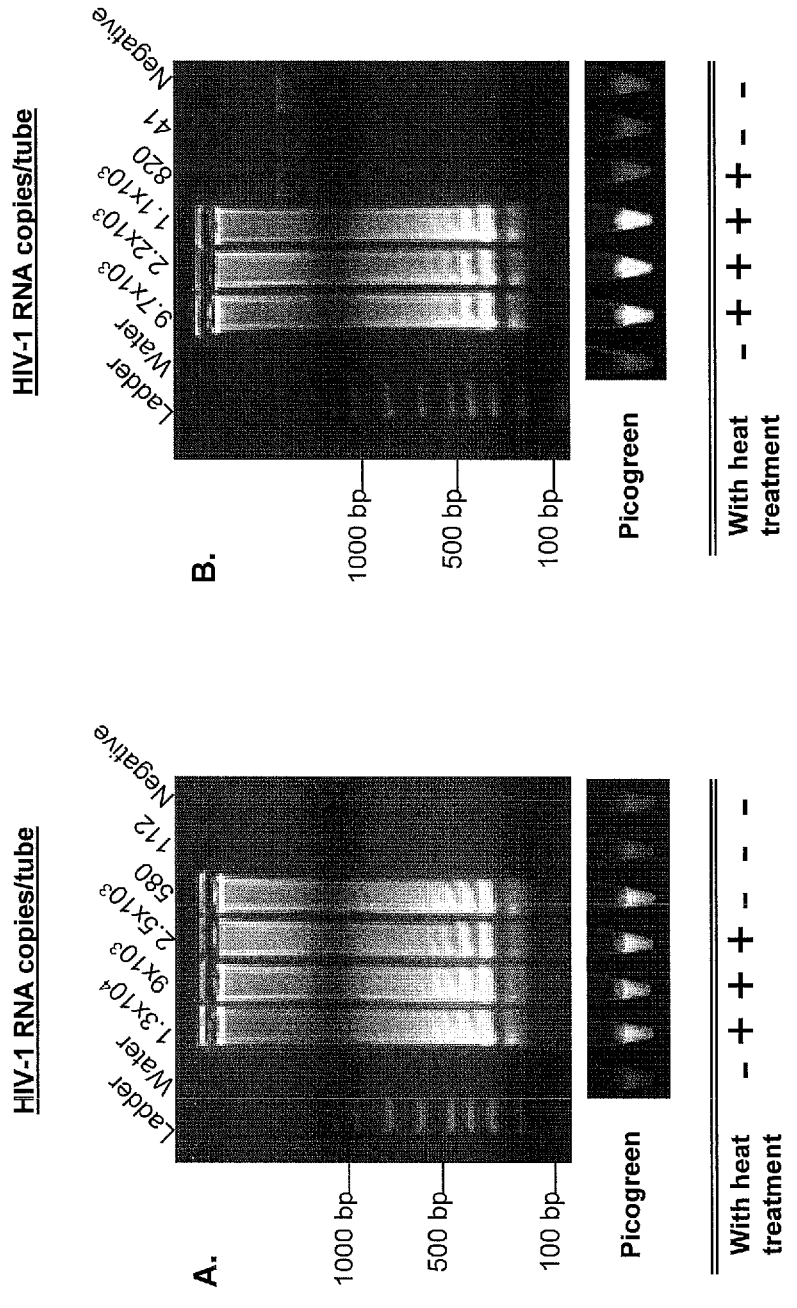
FIG. 3A is an image of an agarose gel stained with ethidium bromide alongside an image of reaction tubes, each showing reaction products of a method of accelerated RT-LAMP of the present invention using a primer set specific for HIV-1 protease DNA and RNA, and using an HIV-1 RNA template isolated from seropositive human plasma wherein the figure also includes an indication of detection of reaction product using heat treated blood or plasma directly in the accelerated RT-LAMP.
FIG. 3B is an image of an agarose gel stained with ethidium bromide showing reaction products of a method of accelerated RT-LAMP using a primer set specific for HIV-1 p24 DNA and RNA, and using an HIV-1 DNA and/or RNA template isolated from HIV positive human blood samples wherein the figure also includes an indication of detection of reaction product using heat treated blood or plasma directly in the accelerated RT-LAMP.

An aliquot of 10 µl of each heated sample is added to a reaction mix containing 0.2 µM of each F3 and B3 primers, 1.6 µM of each FIP and BIP primers, 0.8 µM of each LoopF and LoopB primers, 0.4M betaine (Sigma-Aldrich, St. Louis, Mo.), 10 mM $MgSO_4$, 1.4 mM dNTPs, 1× ThermoPol reaction buffer (New England Biolabs, Ipswich, Ma.), 8 U Bst DNA polymerase (New England Biolabs), and 0.625 U AMV reverse transcriptase (Invitrogen, Carlsbad, Calif.). The samples are obtained from the same donors that are used for nucleic acid isolation, so that a direct comparison could be made between the sample preparation methods. The RT-LAMP assay is able to detect 3 out of the 5 heat-treated plasma samples and 4 out of the 5 blood samples as shown in FIG. 3 where results are indicated as positive (+) or negative (−) below the corresponding extracted RNA gel and Picogreen results. While one less plasma sample is detected following heat treatment as compared to nucleic acid isolation, one more blood sample is detected following heat treatment.

Heat-treatment of HIV-infected blood samples yields a higher sensitivity as compared to RNA isolated from the same samples. Direct heating of whole blood samples, as opposed to nucleic acid isolation, may increase sensitivity of the assay because there is little or no loss of nucleic acid, which can occur with the isolation procedure. Furthermore, eliminating the need for nucleic acid isolation reduces the overall procedure time, in this case to approximately 90 minutes.

Similar procedures are used for other HIV-1 specific primers to obtain similar HIV-1 specific results and for HIV-2 specific primers to obtain similar HIV-2 specific results.

Example 13

Sensitivity of Primer Sets to Extracted Nucleic Acid

TABLE III

| | Copies/tube | p24 | Protease | Envelope | Integrase | p24 Degenerate | p24 + Protease Combined |
|---|---|---|---|---|---|---|---|
| DNA | 1000 | + | + | + | ND | ND | + |
| | 100 | + | + | + | + | + | + |
| | 10 | + | + | + | + | + | + |
| RNA | 1,000 | + | + | + | + | ND | + |
| | 100 | + | + | + | + | ND | + |
| | 50 | − | ND | + | ND | ND | ND |
| | 10 | − | − | − | − | ND | − |

Table III shows detection of extracted nucleic acid using each primer set individually, and using the HIV-1 p24 primer set and the HIV-1 protease primer set together, in reactions having a 25 µl reaction volume. Sensitivity is tested against extracted DNA and RNA at indicated concentrations (Copy #1 tube). ND (No Data) represents reaction conditions for which data is not present in this example.

Similar procedures are used for other HIV-1 specific primers to obtain similar HIV-1 specific results and for HIV-2 specific primers to obtain similar HIV-2 specific results.

Example 14

Sequence Specific Detection Method for Lamp Reaction Products

While agarose gel electrophoresis can distinguish between specific and non-specific banding patterns, it requires an additional hour for detection and may be undesirable in time-sensitive situations. For direct visual detection of amplified products, sequence specific probes are provided by the present invention that will not incorporate into non-specific amplification and can be observed with a UV lamp.

HIV-1 and HIV-2 specific LAMP probes are designed by adding a fluorescent HEX tag to the 5' end of Loop F or Loop B primers. Probe/quencher pairs for the HIV-1 p24, HIV-1 protease, and HIV-1 envelope primer sets are shown in Table IV.

TABLE IV

Probe/Quencher Sequences 5' to 3' p24

| LoopB Probe | HEX-GAGATCCAAGGGGAAGTGA |
|---|---|
| Quencher | TCACTTCCCCTTGGATCTC-BHQ |

Protease

| LoopB Probe | HEX-TATCAAAGTAAGACAGTA |
|---|---|
| Quencher | TACTGTCTTACTTTGATA-BHQ |

Envelope

| LoopF Probe | HEX-CAAAATAGAGTGGTGGTTGCT |
|---|---|
| Quencher | AGCAACCACCACTCTATTTTG-BHQ |

Sequence specific detection is evaluated by testing isolated RNA from a HIV RNA Linearity Panel (BBI Diagnostics, West Bridgewater, Mass.). Quencher probes are added to all samples following amplification, performed as described herein, to quench the fluorescence of any unbound probe. Quencher probes include the complementary sequence of the fluorescent-tagged primers with the addition of Black Hole Quencher (BHQ1) to the 3' end of the probe. The incorporation of a fluorescent probe into the LAMP reaction allowed for immediate visualization of the amplified products in reaction tubes using a UV lamp as shown in FIGS. 4A and 4B. Direct comparison of the signal in the reaction tubes to agarose gel electrophoresis where signal is due to a non-specific intercalator, FIG. 4C, shows that the sequence specific fluorescent probes are not incorporating into non-specific amplifications but are amplifying the signal of the sequence specific products.

Similar procedures are used for other HIV-1 specific primers to obtain similar HIV-1 specific results and for HIV-2 specific primers to obtain similar HIV-2 specific results.

Example 13 p24 and p24-FGE Primers Detect Multiple HIV-1 Clades

P24 primer sets are used to detect HIV-1 P24 in various HIV-1 clades including clades A, B, C, D, E, F, and G. Primer sets used in this example are SEQ ID Nos. 1-6 (p24) or SEQ ID No.s 1-3, 5, 77 and 78 (P24 optimized to detect clades FGE). The RT-LAMP reaction is carried out in a 25 µl volume (total) containing the following components: 0.2 µM of each F3 and B3 primers (SEQ ID Nos. 1 and 2, respectively), 1.6 µM of each FIP and BIP primers (SEQ ID Nos. 3 and 4, respectively) or 1.6 µM of each FIP and BIP-FGE primers (SEQ ID Nos. 3 and 77, respectively), 0.8 µM of each LoopF and LoopB primers (SEQ ID Nos. 5 and 6, respectively) or 0.8 µM of each LoopF and LoopB-FGE primers (SEQ ID Nos. 5 and 78, respectively), 0.4M betaine (Sigma-Aldrich, St. Louis, Mo.), 10 mM MgSO$_4$, 1.4 mM dNTPs, 1× ThermoPol reaction buffer (New England Biolabs, Ipswich, Ma.), 8 U Bst DNA polymerase (New England Biolabs), 0.625 U AMV reverse transcriptase (Invitrogen, Carlsbad, Calif.), and 10 µl of extracted nucleic

TABLE V

| HIV-1 Isolate | Clade | P24 | P24-FGE |
|---|---|---|---|
| 92RW026 | A | + | − |
| 92UG031 | A | + | + |
| 94UG103 | A | + | + |
| 92US657 | B | + | + |
| 92HT593 | B | + | + |
| 93US076 | B | + | + |
| 93MW959 | C | + | − |
| 98CN009 | C | + | + |
| 97ZA003 | C | + | − |
| 92UG001 | D | + | + |
| 92UG024 | D | + | + |
| 94UG114 | D | + | + |
| CMU02 | E | − | + |
| CMU08 | E | − | + |
| CMU10 | E | − | + |
| 93BR029 | F | − | + |
| 93BR020 | F | − | + |
| 93BR019 | F | + | + |
| HIV-1 G3 | G | − | + |
| RU570 | G | + | + |
| RU132 | G | + | + |
| IVCO3671 | G | − | + | acid or heated plasma/blood containing HIV-1 Glade A, B, C, D, E, F, or G. RT-LAMP amplification is carried out using a GeneAmp® PCR System (Applied Biosystems, Foster City, Calif.). The reaction mixture is heated at 60° C. for 60 minutes and then held at 80° C. for 2 minutes to terminate the reaction. Negative controls are included in each run, including a water control to check for cross-contamination.

Table V shows results of these reactions, + indicating detection, − indicating no detection.

Example 14

RT-LAMP is used to detect HIV-2 in this example. Primers used are SEQ ID Nos. 79-84. The RT-LAMP reaction is carried out in a 25 µl volume (total) containing the following components: 0.2 µM of each F3 and B3 primers (SEQ ID Nos. 79 and 80, respectively), 1.6 µM of each FIP and BIP primers (SEQ ID Nos. 81 and 82, respectively), 0.8 µM of each LoopF and LoopB primers (SEQ ID Nos. 83 and 84, respectively), 0.4M betaine (Sigma-Aldrich, St. Louis, Mo.), 10 mM MgSO$_4$, 1.4 mM dNTPs, 1× ThermoPol reaction buffer (New England Biolabs, Ipswich, Ma.), 8 U Bst DNA polymerase (New England Biolabs), 0.625 U AMV reverse transcriptase (Invitrogen, Carlsbad, Calif.), and 10 µl of extracted HIV-2 nucleic acid from strains NIH-Z, SLRHC and GB122. RT-LAMP amplification is carried out using a GeneAmp® PCR System (Applied Biosystems, Foster City, Calif.). The reaction mixture is heated at 60° C. for 60 minutes and then held at 80° C. for 2 minutes to terminate the reaction. Negative controls are included in each run, including a water control to check for cross-contamination.

Figure 5:
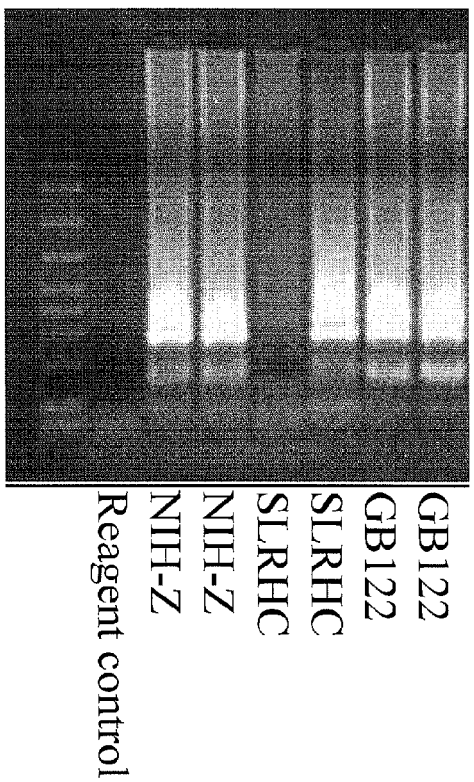
FIG. 5 is an image of an agarose gel stained with ethidium bromide showing reaction products of a method of accelerated RT-LAMP using a primer set specific for HIV-2 pol DNA and RNA.

FIG. 5 is an image of an agarose gel stained with ethidium bromide showing reaction products of accelerated RT-LAMP using a primer set specific for HIV-2 pol DNA and RNA as described in this example.

Example 15

HIV-1 is detected in dried blood spot samples. Dried blood spots are created by spotting 100 microliters of HIV negative blood spiked with BaL and 8E5 cells in various amounts onto a Whatman 903 filter paper. The dried blood spots are air dried for three hours and then stored at −20° C. until use in the present assay. BaL virus stock produces HIV-1 RNA and 8E5 cells produce HIV-1 DNA.

Portions of the dried blood spots are obtained using a hole punch and each punch is placed in a 2 mL tube. 250 microliters of water is added to each tube and vortexed.

The RT-LAMP reaction is carried out in a 25 µl volume (total) containing the following components: 0.2 µM of each F3 and B3 primers, SEQ ID Nos. 1 and 2 respectively, 1.6 µM of each FIP and BIP primers, SEQ ID Nos. 3 and 4, respectively, 0.8 µM of each LoopF and LoopB primers, SEQ ID Nos. 5 and 6, respectively, 0.4M betaine (Sigma-Aldrich, St. Louis, Mo.), 10 mM MgSO$_4$, 1.4 mM dNTPs, 1× ThermoPol reaction buffer (New England Biolabs, Ipswich, Ma.), 8 U Bst DNA polymerase (New England Biolabs), 0.625 U AMV reverse transcriptase (Invitrogen, Carlsbad, Calif.), and 10 µl of supernatant from a tube containing the vortexed dried blood spot punch. RT-LAMP amplification is carried out using a GeneAmp® PCR System (Applied Biosystems, Foster City, Calif.). The reaction mixture is heated at 60° C. for 60 minutes and then held at 80° C. for 2 minutes to terminate the reaction. Negative controls are included in each run, including a water control to check for cross-contamination.

Figure 6:
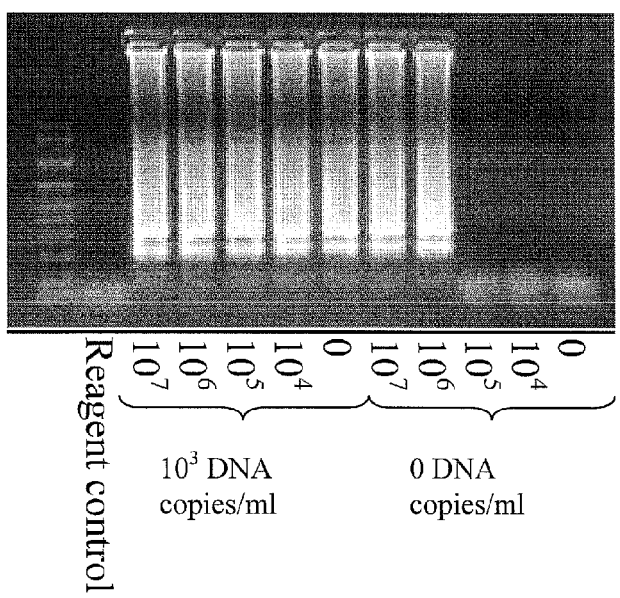
FIG. 6 is an image of an agarose gel stained with ethidium bromide showing detection of HIV-1 nucleic acids in dried blood spot samples using accelerated RT-LAMP according to embodiments of the present invention.

FIG. 6 is an image of an agarose gel stained with ethidium bromide showing detection of HIV-1 nucleic acids in dried blood spot samples using accelerated RT-LAMP according to embodiments of the present invention.

REFERENCES

1989. Interpretation and use of the western blot assay for serodiagnosis of human immunodeficiency virus type 1 infections. MMWR Morb Mortal Wkly Rep 38, 1-7.

Brown, B. K., Darden, J. M., Tovanabutra, S., Oblander, T., Frost, J., Sanders-Buell, E., de Souza, M. S., Birx, D. L., McCutchan, F. E. and Polonis, V. R., 2005. Biologic and genetic characterization of a panel of 60 human immunodeficiency virus type 1 isolates, representing clades A, B, C, D, CRF01_AE, and CRF02_AG, for the development and assessment of candidate vaccines. J Virol 79, 6089-101.

Butera, S. T., Perez, V. L., Wu, B. Y., Nabel, G. J. and Folks, T. M., 1991. Oscillation of the human immunodeficiency virus surface receptor is regulated by the state of viral activation in a CD4+ cell model of chronic infection. J Virol 65, 4645-53.

Buttke, T. M. and Folks, T. M., 1992. Complete replacement of membrane cholesterol with 4,4',14-trimethyl sterols in a human T cell line defective in lanosterol demethylation. J Biol Chem 267, 8819-26.

Daar, E. S., Little, S., Pitt, J., Santangelo, J., Ho, P., Harawa, N., Kerndt, P., Glorgi, J. V., Bai, J., Gaut, P., Richman, D. D., Mandel, S, and Nichols, S., 2001. Diagnosis of primary HIV-1 infection. Los Angeles County Primary HIV Infection Recruitment Network. Ann Intern Med 134, 25-9.

Fiebig, E. W., Wright, D. J., Rawal, B. D., Garrett, P. E., Schumacher, R. T., Peddada, L., Heldebrant, C., Smith, R., Conrad, A., Kleinman, S. H. and Busch, M. P., 2003. Dynamics of HIV viremia and antibody seroconversion in plasma donors: implications for diagnosis and staging of primary HIV infection. Aids 17, 1871-9.

Fiscus, S. A., Pilcher, C. D., Miller, W. C., Powers, K. A., Hoffman, I. F., Price, M., Chilongozi, D. A., Mapanje, C., Krysiak, R., Gama, S., Martinson, F. E. and Cohen, M. S., 2007. Rapid, real-time detection of acute HIV infection in patients in Africa. J Infect Dis 195, 416-24.

Folks, T., Benn, S., Rabson, A., Theodore, T., Hoggan, M. D., Martin, M., Lightfoote, M. and Sell, K., 1985. Characterization of a continuous T-cell line susceptible to the cytopathic effects of the acquired immunodeficiency syndrome (AIDS)-associated retrovirus. Proc Natl Acad Sci USA 82, 4539-43.

Hecht, F. M., Busch, M. P., Rawal, B., Webb, M., Rosenberg, E., Swanson, M., Chesney, M., Anderson, J., Levy, J. and Kahn, J. O., 2002. Use of laboratory tests and clinical symptoms for identification of primary HIV infection. Aids 16, 1119-29.

Hemelaar, J., Gouws, E., Ghys, P. D. and Osmanov, S., 2006. Global and regional distribution of HIV-1 genetic subtypes and recombinants in 2004. Aids 20, W13-23.

Hong, T. C., Mai, Q. L., Cuong, D. V., Parida, M., Minekawa, H., Notomi, T., Hasebe, F. and Morita, K., 2004. Development and evaluation of a novel loop-mediated isothermal amplification method for rapid detection of severe acute respiratory syndrome coronavirus. J Clin Microbiol 42, 1956-61.

Iweala, O. I., 2004. HIV diagnostic tests: an overview. Contraception 70, 141-7.

Ketema, F., Zink, H. L., Kreisel, K. M., Croxton, T. and Constantine, N. T., 2005. A 10-minute, US Food and Drug Administration-approved HIV test. Expert Rev Mol Diagn 5, 135-43.

Kurosaki, Y., Takada, A., Ebihara, H., Grolla, A., Kamo, N., Feldmann, H., Kawaoka, Y. and Yasuda, J., 2007. Rapid and simple detection of Ebola virus by reverse transcription-loop-mediated isothermal amplification. J Virol Methods 141, 78-83.

Lillo, F. B., Grasso, M. A., Lodini, S., Bellotti, M. G. and Colucci, G., 2004. Few modifications of the Cobas Amplicor HIV Monitor 1.5 test allow reliable quantitation of HIV-1 proviral load in peripheral blood mononuclear cells. J Virol Methods 120, 201-5.

Nagamine, K., Hase, T. and Notomi, T., 2002. Accelerated reaction by loop-mediated isothermal amplification using loop primers. Mol Cell Probes 16, 223-9.

Nagamine, K., Watanabe, K., Ohtsuka, K., Hase, T. and Notomi, T., 2001. Loop-mediated isothermal amplification reaction using a nondenatured template. Clin Chem 47, 1742-3.

Notomi, T., Okayama, H., Masubuchi, H., Yonekawa, T., Watanabe, K., Amino, N. and Hase, T., 2000. Loop-mediated isothermal amplification of DNA. Nucleic Acids Res 28, E63.

Patel, P., Klausner, J. D., Bacon, O. M., Liska, S., Taylor, M., Gonzalez, A., Kohn, R. P., Wong, W., Harvey, S., Kerndt, P. R. and Holmberg, S. D., 2006. Detection of acute HIV infections in high-risk patients in California. J Acquir Immune Defic Syndr 42, 75-9.

Pilcher, C. D., Eron, J. J., Jr., Galvin, S., Gay, C. and Cohen, M. S., 2004. Acute HIV revisited: new opportunities for treatment and prevention. J Clin Invest 113, 937-45.

Pilcher, C. D., Shugars, D. C., Fiscus, S. A., Miller, W. C., Menezes, P., Giner, J., Dean, B., Robertson, K., Hart, C. E., Lennox, J. L., Eron, J. J., Jr. and Hicks, C. B., 2001. HIV in body fluids during primary HIV infection: implications for pathogenesis, treatment and public health. Aids 15, 837-45.

Puchhammer-Stockl, E., Schmied, B., Rieger, A., Sarcletti, M., Geit, M., Zangerle, R. and Hofmann, H., 2005. Low proportion of recent human immunodeficiency virus (HIV) infections among newly diagnosed cases of HIV infection as shown by the presence of HIV-specific antibodies of low avidity. J Clin Microbiol 43, 497-8.

Schacker, T., Collier, A. C., Hughes, J., Shea, T. and Corey, L., 1996. Clinical and epidemiologic features of primary HIV infection. Ann Intern Med 125, 257-64.

Soliman, H. and El-Matbouli, M., 2006. Reverse transcription loop-mediated isothermal amplification (RT-LAMP) for rapid detection of viral hemorrhagic septicaemia virus (VHS). Vet Microbiol 114, 205-13.

Weber, B., 2006. Screening of HIV infection: role of molecular and immunological assays. Expert Rev Mol Diagn 6, 399-411.

Yoshida, N., Fujino, M., Ota, Y., Notomi, T. and Nakayama, T., 2007. Simple differentiation method of mumps Hoshino vaccine strain from wild strains by reverse transcription loop-mediated isothermal amplification (RT-LAMP). Vaccine 25, 1281-6.

HXB2 Reference Strain of HIV-1 complete genome:

(SEQ ID No. 413)

```
   1 ggtctctctg gttagaccag atctgagcct gggagctctc tggctaacta gggaacccac
  61 tgcttaagcc tcaataaagc ttgccttgag tgcttcaagt agtgtgtgcc cgtctgttgt
 121 gtgactctgg taactagaga tccctcagac cctttagtc agtgtggaaa atctctagca
 181 gtggcgcccg aacagggacc tgaaagcgaa agggaaacca gaggagctct ctcgacgcag
 241 gactcggctt gctgaagcgc gcacggcaag aggcgagggg cggcgactgg tgagtacgcc
 301 aaaaattttg actagcggag gctagaagga gagagatggg tgcgagagcg tcagtattaa
 361 gcgggggaga attagatcga tgggaaaaaa ttcggttaag gccaggggga agaaaaaat
 421 ataaattaaa acatatagta tgggcaagca gggagctaga acgattcgca gttaatcctg
 481 gcctgttaga acatcagaa ggctgtagac aaatactggg acagctacaa ccatcccttc
 541 agacaggatc agaagaactt agatcattat ataatacagt agcaaccctc tattgtgtgc
 601 atcaaaggat agagataaaa gacaccaagg aagctttaga caagatagag gaagagcaaa
 661 acaaaagtaa gaaaaaagca cagcaagcag cagctgacac aggacacagc aatcaggtca
 721 gccaaaatta ccctatagtg cagaacatcc aggggcaaat ggtacatcag gccatatcac
 781 ctagaacttt aaatgcatgg gtaaaagtag tagaagagaa ggctttcagc ccagaagtga
 841 tacccatgtt ttcagcatta tcagaaggag ccaccccaca agatttaaac accatgctaa
 901 acacagtggg gggacatcaa gcagccatgc aaatgttaaa agagaccatc aatgaggaag
 961 ctgcagaatg ggatagagtg catccagtgc atgcagggcc tattgcacca ggccagatga
1021 gagaaccaag gggaagtgac atagcaggaa ctactagtac ccttcaggaa caaataggat
1081 ggatgacaaa taatccacct atcccagtag gagaaattta taaaagatgg ataatcctgg
1141 gattaaataa aatagtaaga atgtatagcc ctaccagcat tctggacata agacaaggac
1201 caaaggaacc ctttagagac tatgtagacc ggttctataa aactctaaga gccgagcaag
1261 cttcacagga ggtaaaaaat tggatgacag aaaccttgtt ggtccaaaat gcgaacccag
1321 attgtaagac tattttaaaa gcattgggac cagcggctac actagaagaa atgatgacag
1381 catgtcaggg agtaggagga cccggccata aggcaagagt tttggctgaa gcaatgagcc
1441 aagtaacaaa ttcagctacc ataatgatgc agagaggcaa ttttaggaac caaagaaaga
1501 ttgttaagtg tttcaattgt ggcaaagaag gcacacagc cagaaattgc agggccccta
1561 ggaaaaaggg ctgttggaaa tgtggaaagg aaggacacca aatgaaagat tgtactgaga
1621 gacaggctaa ttttttaggg aagatctggc cttcctacaa gggaaggcca gggaattttc
1681 ttcagagcag accagagcca acagccccac cagaagagag cttcaggtct ggggtagaga
1741 caacaactcc ccctcagaag caggagccga tagacaagga actgtatcct ttaacttccc
1801 tcaggtcact ctttggcaac gacccctcgt cacaataaag ataggggggc aactaaagga
1861 agctctatta gatacaggag cagatgatac agtattagaa gaaatgagtt tgccaggaag
1921 atggaaacca aaaatgatag ggggaattgg aggttttatc aaagtaagac agtatgatca
1981 gatactcata gaaatctgtg gacataaagc tataggtaca gtattagtag gacctacacc
```

-continued

```
2041 tgtcaacata attggaagaa atctgttgac tcagattggt tgcactttaa attttcccat 2101 tagccctatt gagactgtac cagtaaaatt aaagccagga atggatggcc caaaagttaa 2161 acaatggcca ttgacagaag aaaaaataaa agcattagta gaaatttgta cagagatgga 2221 aaaggaaggg aaaatttcaa aaattgggcc tgaaaatcca tacaatactc cagtatttgc 2281 cataaagaaa aaagacagta ctaaatggag aaaattagta gatttcagag aacttaataa 2341 gagaactcaa gacttctggg aagttcaatt aggaatacca catcccgcag ggttaaaaaa 2401 gaaaaaatca gtaacagtac tggatgtggg tgatgcatat ttttcagttc ccttagatga 2461 agacttcagg aagtatactg catttaccat acctagtata aacaatgaga caccagggat 2521 tagatatcag tacaatgtgc ttccacaggg atggaaagga tcaccagcaa tattccaaag 2581 tagcatgaca aaaatcttag agccttttag aaaacaaaat ccagacatag ttatctatca 2641 atacatggat gatttgtatg taggatctga cttagaaata gggcagcata gaacaaaaat 2701 agaggagctg agacaacatc tgttgaggtg gggacttacc acaccagaca aaaaacatca 2761 gaaagaacct ccattccttt ggatgggtta tgaactccat cctgataaat ggacagtaca 2821 gcctatagtg ctgccagaaa aagacagctg gactgtcaat gacatacaga agttagtggg 2881 gaaattgaat tgggcaagtc agatttaccc agggattaaa gtaaggcaat tatgtaaact 2941 ccttagagga accaaagcac taacagaagt aataccacta acagaagaag cagagctaga 3001 actggcagaa aacagagaga ttctaaaaga accagtacat ggagtgtatt atgacccatc 3061 aaaagactta atagcagaaa tacagaagca ggggcaaggc caatggacat atcaaattta 3121 tcaagagcca tttaaaaatc tgaaaacagg aaaatatgca agaatgaggg gtgcccacac 3181 taatgatgta aaacaattaa cagaggcagt gcaaaaaata accacagaaa gcatagtaat 3241 atggggaaag actcctaaat ttaaactgcc catacaaaag gaaacatggg aaacatggtg 3301 gacagagtat tggcaagcca cctggattcc tgagtgggag tttgttaata cccctccctt 3361 agtgaaatta tggtaccagt tagagaaaga acccatagta ggagcagaaa ccttctatgt 3421 agatggggca gctaacaggg agactaaatt aggaaaagca ggatatgtta ctaatagagg 3481 aagacaaaaa gttgtcaccc taactgacac aacaaatcag aagactgagt tacaagcaat 3541 ttatctagct ttgcaggatt cgggattaga agtaaacata gtaacagact cacaatatgc 3601 attaggaatc attcaagcac aaccagatca aagtgaatca gagttagtca atcaaataat 3661 agagcagtta ataaaaaagg aaaaggtcta tctggcatgg gtaccagcac acaaaggaat 3721 tggaggaaat gaacaagtag ataaattagt cagtgctgga atcaggaaag tactattttt 3781 agatggaata gataaggccc aagatgaaca tgagaaatat cacagtaatt ggagagcaat 3841 ggctagtgat tttaacctgc cacctgtagt agcaaaagaa atagtagcca gctgtgataa 3901 atgtcagcta aaaggagaag ccatgcatgg acaagtagac tgtagtccag gaatatggca 3961 actagattgt acacatttag aaggaaaagt tatcctggta gcagttcatg tagccagtgg 4021 atatatagaa gcagaagtta ttccagcaga acagggcag gaaacagcat attttctttt 4081 aaaattagca ggaagatggc cagtaaaaac aatacatact gacaatggca gcaatttcac 4141 cggtgctacg gttagggccg cctgttggtg ggcgggaatc aagcaggaat ttggaattcc 4201 ctacaatccc caaagtcaag gagtagtaga atctatgaat aaagaattaa agaaaattat 4261 aggacaggta agagatcagg ctgaacatct taagacagca gtacaaatgg cagtattcat 4321 ccacaatttt aaaagaaaag gggggattgg ggggtacagt gcaggggaaa gaatagtaga 4381 cataatagca acagacatac aaactaaaga attacaaaaa caaattacaa aaattcaaaa
```

-continued

```
4441 ttttcgggtt tattacaggg acagcagaaa tccactttgg aaaggaccag caaagctcct 4501 ctggaaaggt gaaggggcag tagtaataca agataatagt gacataaaag tagtgccaag 4561 aagaaaagca aagatcatta gggattatgg aaaacagatg gcaggtgatg attgtgtggc 4621 aagtagacag gatgaggatt agaacatgga aaagtttagt aaaacaccat atgtatgttt 4681 cagggaaagc tagggatgg ttttatagac atcactatga aagccctcat ccaagaataa 4741 gttcagaagt acacatccca ctagggatg ctagattggt aataacaaca tattggggtc 4801 tgcatacagg agaaagagac tggcatttgg gtcagggagt ctccatagaa tggaggaaaa 4861 agagatatag cacacaagta gaccctgaac tagcagacca actaattcat ctgtattact 4921 ttgactgttt ttcagactct gctataagaa aggccttatt aggacacata gttagcccta 4981 ggtgtgaata tcaagcagga cataacaagg taggatctct acaatacttg gcactagcag 5041 cattaataac accaaaaaag ataaagccac ctttgcctag tgttacgaaa ctgacagagg 5101 atagatggaa caagccccag aagaccaagg gccacagagg gagccacaca atgaatggac 5161 actagagctt ttagaggagc ttaagaatga agctgttaga cattttccta ggatttggct 5221 ccatggctta gggcaacata tctatgaaac ttatggggat acttgggcag gagtggaagc 5281 cataataaga attctgcaac aactgctgtt tatccatttt cagaattggg tgtcgacata 5341 gcagaatagg cgttactcga cagaggagag caagaaatgg agccagtaga tcctagacta 5401 gagccctgga agcatccagg aagtcagcct aaaactgctt gtaccaattg ctattgtaaa 5461 aagtgttgct ttcattgcca gtttgtttc ataacaaaag ccttaggcat ctcctatggc 5521 aggaagaagc ggagacagcg acgaagagct catcagaaca gtcagactca tcaagcttct 5581 ctatcaaagc agtaagtagt acatgtaatg caacctatac caatagtagc aatagtagca 5641 ttagtagtag caataataat agcaatagtt gtgtggtcca tagtaatcat agaatatagg 5701 aaaatattaa gacaaagaaa atagacagg ttaattgata gactaataga aagagcagaa 5761 gacagtggca atgagagtga aggagaaata tcagcacttg tggagatggg ggtggagatg 5821 gggcaccatg ctccttggga tgttgatgat ctgtagtgct acagaaaaat tgtgggtcac 5881 agtctattat ggggtacctg tgtggaagga agcaaccacc actctatttt gtgcatcaga 5941 tgctaaagca tatgatacag aggtacataa tgtttgggcc acacatgcct gtgtacccac 6001 agaccccaac ccacaagaag tagtattggt aaatgtgaca gaaaatttta acatgtggaa 6061 aaatgacatg gtagaacaga tgcatgagga tataatcagt ttatgggatc aaagcctaaa 6121 gccatgtgta aaattaaccc cactctgtgt tagtttaaag tgcactgatt tgaagaatga 6181 tactaatacc aatagtagta gcgggagaat gataatggag aaaggagaga taaaaaactg 6241 ctctttcaat atcagcacaa gcataagagg taaggtgcag aaagaatatg catttttta 6301 taaacttgat ataataccaa tagataatga tactaccagc tataagttga caagttgtaa 6361 cacctcagtc attacacagg cctgtccaaa ggtatccttt gagccaattc ccatacatta 6421 ttgtgccccg gctggttttg cgattctaaa atgtaataat aagacgttca atggaacagg 6481 accatgtaca aatgtcagca cagtacaatg tacacatgga attaggccag tagtatcaac 6541 tcaactgctg ttaaatggca gtctagcaga agaaggta gtaattagat ctgtcaattt 6601 cacggacaat gctaaaacca taatagtaca gctgaacaca tctgtagaaa ttaattgtac 6661 aagacccaac aacaatacaa gaaaagaat ccgtatccag agaggaccag ggagagcatt 6721 tgttacaata ggaaaaatag gaaatatgag acaagcacat tgtaacatta gtagagcaaa 6781 atggaataac actttaaaac agatagctag caaattaaga gaacaatttg gaaataataa 6841 aacaataatc tttaagcaat cctcaggagg ggacccagaa attgtaacgc acagttttaa
```

-continued

```
6901 ttgtggaggg gaattttcct actgtaattc aacacaactg tttaatagta cttggtttaa
6961 tagtacttgg agtactgaag ggtcaaataa cactgaagga agtgacacaa tcaccctccc
7021 atgcagaata aaacaaatta taaacatgtg gcagaaagta ggaaaagcaa tgtatgcccc
7081 tcccatcagt ggacaaatta gatgttcatc aaatattaca gggctgctat taacaagaga
7141 tggtggtaat agcaacaatg agtccgagat cttcagacct ggaggaggag atatgaggga
7201 caattggaga agtgaattat ataaatataa agtagtaaaa attgaaccat taggagtagc
7261 acccaccaag gcaaagagaa gagtggtgca gagagaaaaa agagcagtgg gaataggagc
7321 tttgttcctt gggttcttgg gagcagcagg aagcactatg ggcgcagcct caatgacgct
7381 gacggtacag gccagacaat tattgtctgg tatagtgcag cagcagaaca atttgctgag
7441 ggctattgag gcgcaacagc atctgttgca actcacagtc tggggcatca agcagctcca
7501 ggcaagaatc ctggctgtgg aaagatacct aaaggatcaa cagctcctgg ggatttgggg
7561 ttgctctgga aaactcattt gcaccactgc tgtgccttgg aatgctagtt ggagtaataa
7621 atctctggaa cagatttgga atcacacgac ctggatggag tgggacagag aaattaacaa
7681 ttacacaagc ttaatacact ccttaattga agaatcgcaa aaccagcaag aaaagaatga
7741 acaagaatta ttggaattag ataaatgggc aagtttgtgg aattggttta acataacaaa
7801 ttggctgtgg tatataaaat tattcataat gatagtagga ggcttggtag gtttaagaat
7861 agttttttgct gtactttcta tagtgaatag agttaggcag ggatattcac cattatcgtt
7921 tcagacccac ctcccaaccc cgaggggacc cgacaggccc gaaggaatag aagaagaagg
7981 tggagagaga gacagagaca gatccattcg attagtgaac ggatccttgg cacttatctg
8041 ggacgatctg cggagcctgt gcctcttcag ctaccaccgc ttgagagact tactcttgat
8101 tgtaacgagg attgtggaac ttctgggacg cagggggtgg gaagccctca aatattggtg
8161 gaatctccta cagtattgga gtcaggaact aaagaatagt gctgttagct tgctcaatgc
8221 cacagccata gcagtagctg aggggacaga taggttata gaagtagtac aaggagcttg
8281 tagagctatt cgccacatac ctagaagaat aagacagggc ttggaaagga ttttgctata
8341 agatgggtgg caagtggtca aaaagtagtg tgattggatg gcctactgta agggaaagaa
8401 tgagacgagc tgagccagca gcagataggg tgggagcagc atctcgagac ctggaaaaac
8461 atggagcaat cacaagtagc aatacagcag ctaccaatgc tgcttgtgcc tggctagaag
8521 cacaagagga ggaggaggtg ggttttccag tcacacctca ggtaccttta agaccaatga
8581 cttacaaggc agctgtagat cttagccact ttttaaaaga aaaggggggga ctggaagggc
8641 taattcactc ccaaagaaga caagatatcc ttgatctgtg gatctaccac acacaaggct
8701 acttccctga ttagcagaac tacacaccag ggccagggt cagatatcca ctgacctttg
8761 gatggtgcta caagctagta ccagttgagc cagataagat agaagaggcc aataaaggag
8821 agaacaccag cttgttacac cctgtgagcc tgcatgggat ggatgacccg gagagagaag
8881 tgttagagtg gaggtttgac agccgcctag catttcatca cgtgcccga gagctgcatc
8941 cggagtactt caagaactgc tgacatcgag cttgctacaa gggactttcc gctggggact
9001 ttccagggag gcgtggcctg ggcgggactg gggagtggcg agccctcaga tcctgcatat
9061 aagcagctgc tttttgcctg tactgggtct ctctggttag accagatctg agcctgggag
9121 ctctctggct aactagggaa cccactgctt aagcctcaat aaagcttgcc ttgagtgctt
9181 c
```

MAC239 Reference Strain of HIV-2 complete genome:

(SEQ ID No. 414)

-continued

```
   1 aaaggcgcgg gtcggtacca gacggcgtga ggagcgggag aggaagaggc ctccggttgc
  61 aggtaagtgc aacacaaaaa agaaatagct gtcttttatc caggaagggg taataagata
 121 gagtgggaga tgggcgcgag aaactccgtc ttgtcaggga agaaagcaga tgaattagaa
 181 aaaattaggc tacgacccaa cggaaagaaa aagtacatgt tgaagcatgt agtatgggca
 241 gcaaatgaat tagatagatt tggattagca gaaagcctgt tggagaacaa agaaggatgt
 301 caaaaaatac tttcggtctt agctccatta gtgccaacag gctcagaaaa tttaaaaagc
 361 ctttataata ctgtctgcgt catctggtgc attcacgcag aagagaaagt gaaacacact
 421 gaggaagcaa aacagatagt gcagagacac ctagtggtgg aaacaggaac aacagaaact
 481 atgccaaaaa caagtagacc aacagcacca tctagcggca gaggaggaaa ttacccagta
 541 caacaaatag gtggtaacta tgtccacctg ccattaagcc cgagaacatt aaatgcctgg
 601 gtaaaattga tagaggaaaa gaaatttgga gcagaagtag tgccaggatt tcaggcactg
 661 tcagaaggtt gcacccccta tgacattaat cagatgttaa attgtgtggg agaccatcaa
 721 gcggctatgc agattatcag agatattata acgaggaggc tgcagattg ggacttgcag
 781 caccacaac cagctccaca acaaggacaa cttagggagc cgtcaggatc agatattgca
 841 ggaacaacta gttcagtaga tgaacaaatc cagtggatgt acagacaaca gaaccccata
 901 ccagtaggca catttacag gagatggatc caactggggt tgcaaaaatg tgtcagaatg
 961 tataacccaa caaacattct gatgtaaaa caagggccaa aagagccatt tcagagctat
1021 gtagacaggt tctacaaaag tttaagagca gaacagacag atgcagcagt aaagaattgg
1081 atgactcaaa cactgctgat tcaaaatgct aacccagatt gcaagctagt gctgaagggg
1141 ctgggtgtga atcccaccct agaagaaatg ctgacggctt gtcaaggagt agggggggccg
1201 ggacagaagg ctagattaat ggcagaagcc ctgaaagagg ccctcgcacc agtgccaatc
1261 ccttttgcag cagcccaaca gaggggacca agaaagccaa ttaagtgttg gaattgtggg
1321 aaagagggac actctgcaag gcaatgcaga gccccaagaa gacagggatg ctggaaatgt
1381 ggaaaaatgg accatgttat ggccaaatgc ccagacagac aggcgggttt tttaggcctt
1441 ggtccatggg gaaagaagcc ccgcaatttc cccatcgctc aagtgcatca ggggctgatg
1501 ccaactgctc ccccagagga cccagctgtg gatctgctaa gaactacat gcagttgggc
1561 aagcagcaga gagaaaagca cagagaaagc agagagaagc cttacaagga ggtgacagag
1621 gatttgctgc acctcaattc tctctttgga ggagaccagt agtcactgct catattgaag
1681 gacagcctgt agaagtatta ctggatacag gggctgatga ttctattgta acaggaatag
1741 agttaggtcc acattatacc ccaaaaatag taggaggaat aggaggtttt attaatacta
1801 aagaatacaa aaatgtagaa atagaagttt taggcaaaag gattaaaggg acaatcatga
1861 caggggacac cccgattaac attttttggta gaaatttgct aacagctctg gggatgtctc
1921 taaatttcc catagctaaa gtagagcctg taaaagtygc cttaaagcca ggaaaggatg
1981 gaccaaaatt gaagcagtgg ccattatcaa agaaaagat agttgcatta agagaaatct
2041 gtgaaaagat ggaaaaggat ggtcagttgg aggaagctcc cccgaccaat ccatacaaca
2101 cccccacatt tgctataaag aaaaaggata agaacaaatg gagaatgctg atagatttta
2161 gggaactaaa tagggtcact caggacttta cggaagtcca attaggaata ccacaccctg
2221 caggactagc aaaaaggaaa agaattacag tactggatat aggtgatgca tatttctcca
2281 tacctctaga tgaagaattt aggcagtaca ctgcctttac tttaccatca gtaaataatg
2341 cagagccagg aaaacgatac atttataagg ttctgcctca gggatggaag gggtcaccag
2401 ccatcttcca atacactatg agacatgtgc tagaacccct caggaacgca aatccagatg
```

-continued

```
2461  tgaccttagt ccagtatatg gatgacatct taatagctag tgacagcaca gacctggaac
2521  atcacagggt agttttacag ttaaaggaac tcttgaatag catagggttt tctaccccag
2581  aagagaaatt ccaaaaagat cccccatttc aatggatggg gtacgaattg tggccaacaa
2641  aatggaagtt gcaaaagata gagttgccac aaagagagac ctggacagtg aatgatatac
2701  agaagttagt aggagtatta aattgggcag ctcaaattta tccaggtata aaaaccaaac
2761  atctctgtag gttaattaga ggaaaaatga ctctaacaga ggaagttcag tggactgaga
2821  tggcagaagc agaatatgag gaaaataaaa taattctcag tcaggaacaa gaaggatgtt
2881  attaccaaga aggcaagcca ttagaagcca cggtaataaa gagtcaggac aatcagtggt
2941  cttataaaat tcaccaagaa gacaaaatac tgaaagtagg aaaatttgca agataaaga
3001  atacacatac caatggagtg agactattag cacatgtaat acagaaaata ggaaaggaag
3061  caatagtgat ctggggacag gtcccaaaat tccacttacc agttgagaag gatgtatggg
3121  aacagtggtg gacagactat tggcaggtaa cctggatacc ggaatgggat tttatctcaa
3181  caccaccgct agtaagatta gtcttcaatc tagtgaagga ccctatagag ggagaagaaa
3241  cctattatac agatggatca tgtaataaac agtcaaaaga agggaaagca ggatatatca
3301  cagataggg caaagacaaa gtaaaagtgt tagaacagac tactaatcaa caagcagaat
3361  tggaagcatt tctcatggca ttgacagact cagggccaaa ggcaaatatt atagtagatt
3421  cacaatatgt tatgggaata taacaggat gccctacaga atcagagagc aggctagtta
3481  atcaaataat agaagaaatg attaaaaagt cagaaattta tgtagcatgg gtaccagcac
3541  acaaaggtat aggaggaaac caagaaatag accacctagt tagtcaaggg attagacaag
3601  ttctcttctt ggaaaagata gagccagcac aagaagaaca tgataaatac catagtaatg
3661  taaaagaatt ggtattcaaa tttggattac ccagaatagt ggccagacag atagtagaca
3721  cctgtgataa atgtcatcag aaaggagagg ctatacatgg gcagryaaat tcagatctag
3781  ggacttggca aatggattgt acccatctag agggaaaaat aatcatagtt gcagtacatg
3841  tagctagtgg attcatagaa gcagaggtaa ttccacaaga cacaggaaga cagacagcac
3901  tatttctgtt aaaattggca ggcagatggc ctattacaca tctacacaca gataatggtg
3961  ctaactttgc ttcgcaagaa gtaaagatgg ttgcatggtg ggcagggata gagcacacct
4021  ttggggtacc atacaatcca cagagtcagg gagtagtgga agcaatgaat caccacctga
4081  aaaatcaaat agatagaatc agggaacaag caaattcagt agaaaccata gtattaatgg
4141  cagttcattg catgaatttt aaaagaaggg gaggaatagg ggatatgact ccagcagaaa
4201  gattaattaa catgatcact acagaacaag agatacaatt tcaacaatca aaaaactcaa
4261  aatttaaaaa ttttcgggtc tattacagag aaggcagaga tcaactgtgg aagggacccg
4321  gtgagctatt gtggaaaggg gaaggagcag tcatcttaaa ggtagggaca gacattaagg
4381  tagtacccag aagaaaggct aaaattatca aagattatgg aggaggaaaa gaggtggata
4441  gcagttccca catggaggat accggagagg ctagagaggt ggcatagcct cataaaatat
4501  ctgaaatata aaactaaaga tctacaaaag gtttgctatg tgccccattt taaggtcgga
4561  tgggcatggt ggacctgcag cagagtaatc ttcccactac aggaaggaag ccatttagaa
4621  gtacaagggt attggcattt gacaccagaa aaagggtggc tcagtactta tgcagtgagg
4681  ataacctggt actcaaagaa cttttggaca gatgtaacac caaactatgc agacatttta
4741  ctgcatagca cttatttccc ttgctttaca gcgggagaag tgagaagggc catcagggga
4801  gaacaactgc tgtcttgctg caggttcccg agagctcata agtaccaggt accaagccta
```

```
4861 cagtacttag cactgaaagt agtaagcgat gtcagatccc agggagagaa tcccacctgg 4921 aaacagtgga agagacaa taggagaggc cttcgaatgg ctaaacagaa cagtagagga 4981 gataaacaga gaggcggtaa accacctacc aagggagcta attttccagg tttggcaaag 5041 gtcttgggaa tactgcatg atgaacaagg gatgtcacca agctatgtaa aatacagata 5101 cttgtgttta atacaaaagg ctttatttat gcattgcaag aaaggctgta gatgtctagg 5161 ggaaggacat ggggcagggg gatggagacc aggacctcct cctcctcccc ctccaggact 5221 agcataaatg gaagaaagac ctccagaaaa tgaaggacca caaagggaac catgggatga 5281 atgggtagtg gaggttctgg aagaactgaa agaagaagct ttaaaacatt ttgatcctcg 5341 cttgctaact gcacttggta atcatatcta taatagacat ggagacaccc ttgagggagc 5401 aggagaactc attagaatcc tccaacgagc gctcttcatg catttcagag gcggatgcat 5461 ccactccaga atcggccaac ctgggggagg aaatcctctc tcagctatac cgccctctag 5521 aagcatgcta taacacatgc tattgtaaaa agtgttgcta ccattgccag ttttgttttc 5581 ttaaaaaagg cttgggggata tgttatgagc aatcacgaaa gagaagaaga actccgaaaa 5641 aggctaaggc taatacatct tctgcatcaa acaagtaagt atgggatgtc ttgggaatca 5701 gctgcttatc gccatcttgc ttttaagtgt ctatgggatc tattgtactc tatatgtcac 5761 agtcttttat ggtgtaccag cttggaggaa tgcgacaatt cccctctttt gtgcaaccaa 5821 gaatagggat acttggggaa caactcagtg cctaccagat aatggtgatt attcagaaat 5881 ggcccttaat gttacagaaa gctttgatgc ctggaataat acagtcacag aacaggcaat 5941 agaggatgta tggcaactct ttgagacctc aataaggcct tgtgtaaaat tatccccatt 6001 atgcattact atgagatgca ataaagtga gacagataga tggggattga caaaatcaat 6061 aacaacaaca gcatcaacaa catcaacgac agcatcagca aaagtagaca tggtcaatga 6121 gactagttct tgtatagccc aggataattg cacaggcttg gaacaagagc aaatgataag 6181 ctgtaaattc aacatgacag ggttaraaag agacaagaaa aaagagtaca atgaaacttg 6241 gtactctgca gatttggtat gtgaacaagg gaataacact ggtaatgaaa gtagatgtta 6301 catgaaccac tgtaacactt ctgttatcca agagtcttgt gacaaacatt attgggatgc 6361 tattagattt aggtattgtg cacctccagg ttatgctttg cttagatgta atgacacaaa 6421 ttattcaggc tttatgccta atgttctaa ggtggtggtc tcttcatgca aaggatgat 6481 ggagacacag acttctactt ggtttggctt taatggaact agagcagaaa atagaactta 6541 tatttactgg catggtaggg ataataggac tataattagt ttaaataagt attataatct 6601 aacaatgaaa tgtagaagac caggaaataa gacagttta ccagtcacca ttatgtctgg 6661 attggttttc cactcacaac caatcaatga taggccaaag caggcatggt gttggtttgg 6721 aggaaaatgg aagaatgcaa taaaagaggt gaagcagacc attgtcaaac atcccaggta 6781 tactggaact aacaatactg ataaatcaa tttgacggct cctagaggag gagatccgga 6841 agttaccttc atgtggacaa attgcagagg agagttcctc tactgtaaaa tgaattgatt 6901 tctaaattgg gtagaagata ggaatacagc taaccagaag ccaaaggaac agcataaaag 6961 gaattacgtg ccatgtcata ttagacaaat aatcaacact tggcataaag taggcaaaaa 7021 tgtttatttg cctccaagag agggagacct cacgtgtaac tccacagtga ccagtctcat 7081 agcaaacata gattggattg atgaaaacca aactaatatc accatgagtg cagaggtggc 7141 agaactgtat cgattggaat tgggagatta taattagta gagatcactc caattggctt 7201 ggcccccaca ratgtgaaga ggtacactac tggtggcacc tcaagaaaata aaagagggt 7261 cttttgtgcta gggttcttgg gttttctcgc aacggcaggt tctgcaatgg gcgcggcgtc
```

```
7321 gttgacgctg accgctcagt cccgaacttt attggctggg atagtgcagc aacagcaaca 7381 gctgttggac gtggtcaaga gacaacaaga attgttgcga ctgaccgtct ggggaacaaa 7441 gaacctccag actagggtca ctgccatcga gaagtdctta aaggaccagg cgcagctgaa 7501 tgcttgggga tgtgcgttta gacaagtctg ccacactact gtaccatggc caaatgcaag 7561 tctaacacca aagtggaaca atgagacttg gcaagagtgg gagcgaaagg ttgacttctt 7621 ggargaaaat ataacagccc tcctagagga ggcacaaatt caacaagaga agaacatgta 7681 tgaattacaa aagttgaata gctgggatgt gtttgacaat tggtttgacc ttgcttcttg 7741 gataaagtat atacaatatg gagtttatat agttgtagga gtaatactgt taagaatagt 7801 gatctatata gtacaaatgc tagctaagtt aaggcagggg tataggccag tgttctcttc 7861 cccaccctct tatttccagc agacccatat ccaacaggac ccggcactgc caaccagaga 7921 aggcaaagaa ggagacggtg gagaaggcgg tggcaacagc tcctggcctt ggcagataga 7981 atatattcat ttcctgatcc gccaactgat acgcctcttg acttggctat tcagcaactg 8041 cagaaccttg ctatygagag tataccagat cctccaacca atactccaga ggctctctgc 8101 gaccctacag aggattcgag aagtcctcag gactgaactg gcctacctac aatatgggtg 8161 gagctatttc catgaggcgg tccaggccgt ctggagatct gcgacagaga ctcttgcggg 8221 cgcgtgggga gacttatggg agactcttag gagaggtgga agatggatac tcgcaatccc 8281 caggaggatt agacaagggc ttgagctcac tctcttgtga gggacagaaa tacaatcagg 8341 gacagtatat gaatactcca tggagaaacc cagctgaaga gagagaaaaa ttagcataca 8401 gaaaacaaaa tatggatgat atagatgagg aagatgatga cttggtaggg gtatcagtga 8461 ggccaaaagg tccctaaga acaatgagtt acaaattggc aatagacatg tctcattta 8521 taaagaaaa gggggactg gaaggattt attacagtgc aagaagacat agaatcttag 8581 acatatactt agaaaaggaa gaaggcatca taccagattg gcaggattac accttaggac 9641 caggaattag atwcccaaag acatttggct ggctatggaa attagtccct gtaaatgtat 8701 cagatgaggc acaggaggat gagragcatt rtttaatgca tccagctcaa acttcccagt 8761 gggatgaccc ttggggagag gttctagcat ggaagtttga tccaactctg gcctacactt 8821 atgaggcata tgttagatac ccagaagagt ttggaagcaa gtcaggcctg tcagaggaag 8881 aggttagaag aaggctaacc gcaagaggcc ttcttaacat ggctgacaag aaggaaactc 8941 gctgaaacag cagggacttt ccacaagggg atgttacggg gaggtactgg ggaggagccg 9001 gtcgggaacg cccactttct tgatatat
```

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method for detection of HIV nucleic acids in a sample, comprising:

providing a reaction mixture comprising at least one LAMP assay primer set specific for HIV-1 or HIV-2 nucleic acids, magnesium, dNTPs, a reaction buffer, a DNA polymerase and heat-treated plasma or blood to be tested for presence of HIV-1 and/or HIV-2 nucleic acids;

incubating the reaction mixture under DNA polymerase reactions conditions to produce a reaction product comprising amplified HIV nucleic acids; and detecting the reaction product.

2. The method of claim 1, wherein the LAMP primer set is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets.

3. The method of claim 1, wherein the LAMP primer set comprises at least one primer in the LAMP assay primer set which is substantially identical to a primer selected from the group consisting of SEQ ID No. 1-30; 47-58; and 77-84.

4. The method of claim 1, wherein the LAMP primer set comprises an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence.

5. The method of claim 4, wherein the primer set further comprises a LoopF primer selected from HIV-1 P24 LoopF primers of SEQ ID Nos. 155-170 or a substantially identical nucleic acid sequence and a LoopB primer selected from HIV-1 P24 LoopB primers of SEQ ID Nos. 171-174 or a substantially identical nucleic acid sequence.

6. The method of claim 1, wherein the LAMP primer set comprises an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence.

7. The method of claim 6, wherein the LAMP primer set further comprises a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence.

8. The method of claim 1, wherein the LAMP primer set comprises an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence.

9. The method of claim 6, wherein the LAMP primer set further comprises a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

10. The method of claim 1, further comprising a reverse transcriptase.

11. A method for detection of HIV nucleic acid in a sample, comprising:
providing a reaction mixture comprising a LAMP primer set specific for HIV-1 or HIV-2 nucleic acid, wherein the LAMP primer set comprises an F3 primer, a B3 primer, an FIP primer, a BIP primer, a LoopF primer and a LoopB primer, magnesium, dNTPs, a reaction buffer, a DNA polymerase and a sample to be tested for presence of HIV-1 and/or HIV-2 nucleic acid, wherein at least the LoopF primer and/or the LoopB primer of the primer set is a detectably labeled primer;
incubating the reaction mixture under DNA polymerase reactions conditions to produce a reaction product mixture comprising a detectably labeled reaction product;
adding an oligonucleotide bonded to a quencher of the detectable label to the reaction product mixture, the reaction product mixture comprising detectably labeled primers unincorporated into the detectably labeled reaction product, the oligonucleotide complementary to the detectably labeled primers, thereby quenching a detectable signal from the detectably labeled primers unincorporated into the detectably labeled reaction product; and
detecting the detectable label of the detectably labeled reaction product.

12. The method of claim 11, wherein the LAMP primer set is selected from the group consisting of: SEQ ID Nos. 1-4; 1-6; 7-10; 7-12; 13-16; 13-18; 19-22; 19-24; 25-28; 25-30; 47-50; 47-52; 53-56; 53-58; 79-82; 79-84; 1-3 and 77; 1-3, 5, 77 and 78; and a combination of any two or more of these primer sets.

13. The method of claim 11, wherein the LAMP primer set comprises at least one primer that is substantially identical to a primer selected from the group consisting of SEQ ID No. 1-30, 47-58, 77-84 and 91-412.

14. The method of claim 11, wherein the LAMP primer set comprises an F3 primer selected from HIV-1 P24 F3 primers of SEQ ID Nos. 91-106 or a substantially identical nucleic acid sequence, a B3 primer selected from HIV-1 P24 B3 primers of SEQ ID Nos. 107-122 or a substantially identical nucleic acid sequence, a FIP primer selected from HIV-1 P24 FIP primers of SEQ ID Nos. 123-138 or substantially identical nucleic acid sequence, and a BIP primer selected from HIV-1 P24 BIP primers of SEQ ID Nos. 139-154 or a substantially identical nucleic acid sequence.

15. The method of claim 14, wherein the primer set further comprises a LoopF primer selected from HIV-1 P24 LoopF primers of SEQ ID Nos. 155-170 or a substantially identical nucleic acid sequence and a LoopB primer selected from HIV-1 P24 LoopB primers of SEQ ID Nos. 171-174 or a substantially identical nucleic acid sequence.

16. The method of claim 11, wherein the LAMP primer set comprises an F3 primer selected from HIV-1 Protease F3 primers of SEQ ID Nos. 175-190 or a substantially identical nucleic acid sequence, a B3 primer selected from HIV-1 Protease B3 primers of SEQ ID Nos. 191-202 or a substantially identical nucleic acid sequence, a FIP primer selected from HIV-1 Protease FIP primers of SEQ ID Nos. 203-218 or substantially identical nucleic acid sequence, and a BIP primer selected from HIV-1 Protease BIP primers of SEQ ID Nos. 219-250 or a substantially identical nucleic acid sequence.

17. The method of claim 16, wherein the LAMP primer set further comprises a LoopF primer selected from HIV-1 Protease LoopF primers of SEQ ID Nos. 251-254 or a substantially identical nucleic acid sequence and a LoopB primer selected from HIV-1 Protease LoopB primers of SEQ ID Nos. 255-262 or a substantially identical nucleic acid sequence.

18. The method of claim 11, wherein the LAMP primer set comprises an F3 primer selected from HIV-1 Envelope F3 primers of SEQ ID Nos. 263-280 or a substantially identical nucleic acid sequence, a B3 primer selected from HIV-1 Envelope B3 primers of SEQ ID Nos. 281-292 or a substantially identical nucleic acid sequence, a FIP primer selected from HIV-1 Envelope FIP primers of SEQ ID Nos. 293-296 or substantially identical nucleic acid sequence, and a BIP primer selected from HIV-1 Envelope BIP primers of SEQ ID Nos. 297-360 or a substantially identical nucleic acid sequence.

19. The method of claim 18, wherein the LAMP primer set further comprises a LoopF primer selected from HIV-1 Envelope LoopF primers of SEQ ID Nos. 361-408 or a substantially identical nucleic acid sequence and a LoopB primer selected from HIV-1 Envelope LoopB primers of SEQ ID Nos. 409-412 or a substantially identical nucleic acid sequence.

20. The method of claim 11, further comprising a reverse transcriptase.

* * * * *